United States Patent [19]

Taylor

[11] Patent Number: 5,175,314
[45] Date of Patent: Dec. 29, 1992

[54] HERBICIDAL OXATRICYCLIC ETHERS

[75] Inventor: Wendy S. Taylor, Wilmington, Del.

[73] Assignee: E. I. Du Pont de Nemours and Company, Wilmington, Del.

[21] Appl. No.: 818,013

[22] Filed: Jan. 8, 1992

[51] Int. Cl.$^5$ .................. C07D 307/00; A01N 43/12
[52] U.S. Cl. ................................ 549/459; 549/23; 549/51; 549/60; 549/407; 549/414; 549/472; 546/151; 546/269; 548/482; 548/491; 71/88; 71/90; 71/92; 71/94; 71/95; 71/96
[58] Field of Search ............. 549/459, 23, 51, 60, 549/407, 414, 472; 546/151, 269; 548/482, 491; 71/88, 90, 92, 94, 95, 96

[56] References Cited

U.S. PATENT DOCUMENTS

| | | | |
|---|---|---|---|
| 3,676,465 | 7/1972 | Isard et al. | 549/459 |
| 4,486,219 | 12/1984 | Powell | 71/88 |
| 4,486,220 | 12/1984 | Payne | 549/459 |
| 4,670,041 | 6/1987 | Payne et al. | 71/92 |
| 4,828,603 | 5/1989 | Patel et al. | 71/88 |

Primary Examiner—Marianne M. Cintins
Assistant Examiner—John D. Peabody, III

[57] ABSTRACT

This invention relates to certain herbicidal oxatricyclic ethers, agriculturally suitable compositions thereof and a method for their use as broad spectrum preemergent or postemergent herbicides.

6 Claims, No Drawings

HERBICIDAL OXATRICYCLIC ETHERS

BACKGROUND OF THE INVENTION

This invention relates to certain herbicidal ethers, agriculturally suitable compositions thereof, and a method for their use as broad spectrum preemergent or postemergent herbicides.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

U.S. Pat. No. 4,670,041 discloses herbicidal compounds of the formula:

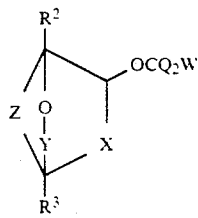

wherein, inter alia:
Y is $(-CR^5R^6-)_n$ in which n is 0, 1 or 2; and
$R^5$ and $R^6$ (in part) form an alkylene group containing 4 or 5 carbon atoms.

U.S. Pat. No. 4,828,603 discloses herbicidal compounds of the formula:

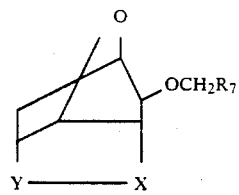

wherein, inter alia:
X is O, S, NR or $CH_2$; and
Y is (in part) $CH_2$.

SUMMARY OF THE INVENTION

Now new compounds effective for controlling the growth of undesired vegetation have been discovered. Accordingly, this invention is directed to compounds of Formulas I through VI including stereoisomers thereof, suitable compositions comprising said compounds and the use of said compounds or compositions as broad spectrum preemergent and postemergent herbicides

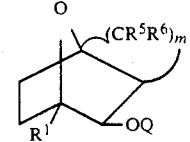 I

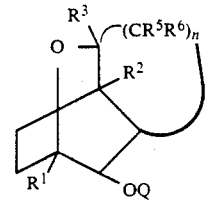 II

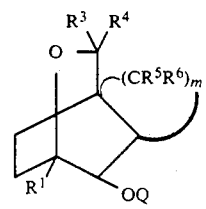 III

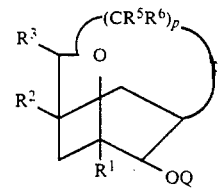 IV

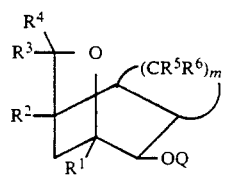 V

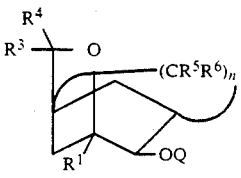 VI wherein
n is 2, 3 or 4;
m is 1, 2, 3 or 4;
p is 1 or 2;
$R^1$ is straight chain $C_1-C_3$ alkyl;
$R^2$ is H, $C_1-C_4$ alkyl, $C_2-C_4$ alkenyl or $C_2-C_4$ alkynyl;
$R^3$ and $R^4$ are independently H, $C_1-C_4$ alkyl, $C_2-C_4$ alkenyl, $C_2-C_4$ alkynyl or $C_1-C_3$ alkyl substituted with $OCH_3$ or $OCH_2CH_3$;
$R^5$ and $R^6$ are independently H, $OCH_3$ or $C_1-C_2$ alkyl;
Q is $CH_2W$ or

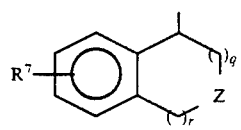

q and r are independently 0, 1 or 2;

$R^7$ is H, halogen, $C_1$-$C_3$ alkyl, $OR^8$, $SR^8$ or CN;
$R^8$ is $C_1$-$C_3$ alkyl or $C_1$-$C_3$ haloalkyl;
Z is $CH_2$, $NR^9$, O, S or may be CH and taken to form a double bond with an adjacent carbon;
$R^9$ is H or $C_1$-$C_3$ alkyl;
W is phenyl optionally substituted with 1-3 substituents selected from halogen, $C_1$-$C_3$ alkyl, $C_1$-$C_3$ alkoxy, OH, CN, $C_1$-$C_3$ haloalkyl, $C_1$-$C_3$ haloalkoxy, $C_1$-$C_3$ alkylthio, $C_2$-$C_4$ alkenyl and $C_2$-$C_4$ alkynyl; or W is a 5-, 6- or 7-membered heterocyclic ring containing 1-3 heteroatoms selected from 1-2 nitrogens, 1-2 oxygens and 1-2 sulfurs, each ring optionally substituted with 1-2 substituents selected from halogen, $CH_3$ and $OCH_3$;
provided that
1) the sum of q and r is 0-2; and
2) if the sum of q and r is O then Z is $CH_2$.

A representative exemplification of the aforementioned heterocycles includes but is not limited to pyrrole, furan, thiophene, tetrahydropyran, tetrahydrofuran, isoxazole, oxazole, pyrazole, imidazole, thiazole, pyridine and pyrazine;

In the above definitions, the term "alkyl", used either alone or in compound words such as "haloalkyl" or "alkylthio", includes straight chain or branched alkyl, e.g. methyl, ethyl, n-propyl, isopropyl or the different butyl isomers.

"Alkoxy", "alkenyl" and "alkynyl" includes straight chain or branched isomers, e.g. ethoxy, n-propyloxy, isopropyloxy, 1-propenyl, 2-propenyl and 3-propenyl.

"Halogen", either alone or in compound words such as "haloalkyl", means fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$.

The compounds of the invention which are preferred for either their biological activity and/or ease of synthesis are:
1. Compound of Formulas I through VI wherein:
$R^5$ and $R^6$ are independently H or $C_1$-$C_2$ alkyl;
Q is $CH_2W$ or

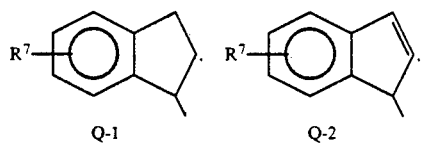

Q-1, Q-2

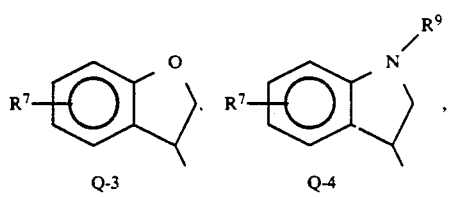

Q-3, Q-4

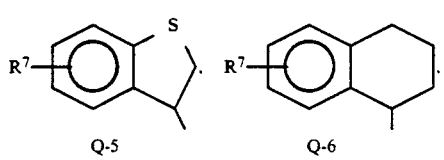

Q-5, Q-6

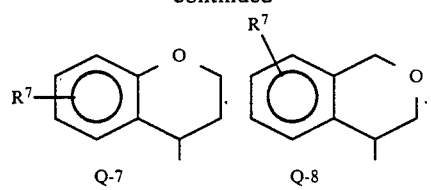

Q-7, Q-8

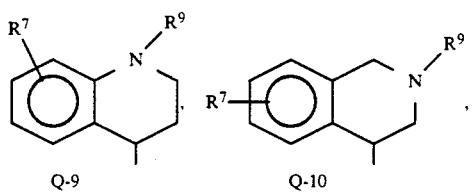

Q-9, Q-10

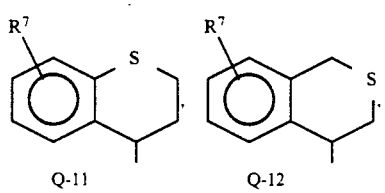

Q-11, Q-12

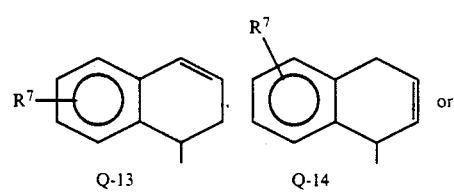

Q-13, Q-14 or

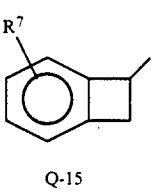

Q-15

W is phenyl optionally substituted with 1-2 substituents selected from F, Cl, Br, $CH_3$ and $OCH_3$; or W is tetrahydropyran, tetrahydrofuran, thiophene, isoxazole, pyridine or pyrazine, each ring optionally substituted with 1-2 substituents selected from F, Cl, Br, $CH_3$ and $OCH_3$.

2. Compounds of Preferred 1 wherein: $R^2$ is H, $C_1$-$C_3$ alkyl, $C_2$-$C_3$ alkenyl or $C_2$-$C_3$ alkynyl.

3. Compounds of Preferred 2 wherein:
$R^3$ and $R^4$ are independently H, $C_1$-$C_3$ alkyl, $C_3$-$C_4$ alkenyl or $C_3$-$C_4$ alkynyl.

4. Compounds of Preferred 3 wherein the compounds are of Formulas I, III and V.

5. Compounds of Preferred 4 wherein:
Q is $CH_2W$, Q-1, Q-3, Q-4, Q-6, Q-7, Q-8 or Q-15;
$R^5$ and $R^6$ are independently H;
W is phenyl optionally substituted with 1-2 substituents selected from F, Cl, Br and $CH_3$; tetrahydrofuran; thiophene optionally substituted with Cl or Br; or pyridine.

6. Compounds of Preferred 5 wherein:
m is 1;
$R^1$ is $CH_3$ or $CH_2CH_3$;
$R^2$ is H, $CH_3$, $CH_2CH_3$ or allyl;
$R^3$ and $R^4$ are H;
Q is $CH_2W$.

Compounds of the invention which are specifically preferred for their biological activity and/or ease of synthesis are the compounds of Preferred 6 which are:

(1α,2α,4α,5β,6α)-(+/−)-5-[(2-chloro-6-fluorophenyl)methoxy]-6-methyl-7-oxatricyclo[4.2.1.0$^{2,4}$]nonane;

(1α,2α,4α,5β,6α)-(+/−-5-[(2-chlorophenyl)methoxy]-6-methyl-7-oxatricyclo[4.2.1.0$^{2,4}$]nonane; and (1α,2α,4α,5β,6α)-(+/−)-5-[(2-fluorophenyl)methoxy]-6-methyl-7-oxatricyclo[4.2.1.0$^{2,4}$]nonane.

Compounds of Formulas I–VI that have the QO group syn with respect to the oxygen-containing bridge are usually more herbicidally active than the anti form. The present invention contemplates all the herbicidally active forms resulting from synthesis and for deliberately created mixtures.

The compositions of the invention suitable for controlling the growth of undesired vegetation comprise an effective amount of any of the compounds disclosed herein and at least one of the following: surfactant, solid diluent or liquid diluent.

Methods for controlling the growth of undesired vegetation are similarly considered to be within the scope of the invention. These methods comprise applying to the locus to be protected an effective amount of any of the compounds disclosed herein. Of particular importance is the method wherein the locus to be protected is rice, corn, soybeans or cereals.

DETAILED DESCRIPTION OF THE INVENTION

The compounds I–VI of the invention are prepared by treating the appropriately substituted oxatricycloalkanols Ia–VIa (which are compounds of Formula I–VI wherein Q is H) with a compound of the formula QX in which X is a halogen atom or a mesyloxy or a tosyloxy group or the like. This reaction is carried out, as shown in Scheme 1, in the presence of a strong base, such as an alkali metal hydride, in an inert solvent, such as ethers, aromatic hydrocarbons, dimethylformamide and the like. Suitable temperatures for the reaction are preferably from 20° C. to 100° C. The product ethers are recovered and isolated by conventional techniques.

Scheme 1

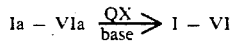

The alkylating agents QX are prepared in the conventional manners known to those skilled in the art from the alcohols QOH.

The alcohols, QOH, are generally known in the art and are most conveniently prepared through metal hydride (e.g., sodium borohydride) reduction of the corresponding carbonyl compounds or the corresponding ketones which can be derived from Friedel-Crafts type cyclization of derivatives of phenylalkylcarboxylic acid, phenoxyalkylcarboxylic acids, benzyloxyalkylcarboxylic acids, phenylthioalkylcarboxylic acids, and benzylthioalkylcarboxylic acids. Details may be found in a) T. Laird in *Comprehensive Organic Chemistry*, D. Barton, W. D. Ollis ed., Vol. 1, pp. 1165–1168, Pergamon Press, New York (1979); b) M. H. Palmer and N. M. Scollick, *J. Chem. Soc. C.*, (1968), 2833; c) C. E. Dolgliesck and Mann, *J. Chem. Soc.*, (1945), 893; d) C. D. Hurd and S. Hayao, *J. Am. Chem. Soc.*, (1954), 76, 4299 and 5056; and e) R. Lesser, *Chem. Ber.* (1923), 56, 1642.

Alternatively, the compounds of Formulas I–VI may be prepared by the coupling procedure described in Scheme 2, which is used in cases where the standard Williamson ether synthesis proves problematic. This procedure uses a Lewis acidic metal oxide wherein the metal can remove the halide ion by forming an insoluble precipitate. For example, silver (I) oxide can be used and the silver halide is the co-product. Alternative metal oxides that may be used are HgO, CaO, MgO. N,N-Dimethylformamide and ethereal solvents, such as diethyl ether, tetrahydrofuran, dioxane, or 1,2-dimethoxyethane are the preferred solvents. Other solvents likely to provide good yields include dipolar aprotic solvents like dimethyl sulfoxide, acetone, and N,N'-dimethylpropyleneurea.

Scheme 2

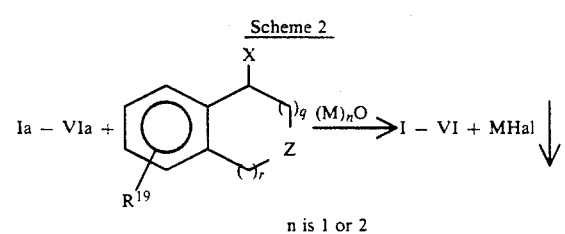

n is 1 or 2

The oxatricycloalkanols Ia–VIa can be obtained generally by one or more of the following routes: directly by a) epoxidation-cyclization of unsaturated cyclic alcohols, with or without isolation of the epoxyalcohol intermediates; indirectly by b) Diels-Alder reactions of furans with dienophiles; or by c) Diels-Alder reactions of other dienes with dienophiles.

Non-limiting illustrations of the preparation of representative compounds follow.

Some of the compounds of Formula I can be prepared through the sequence shown in Scheme 3. Cyclohexene 1 can be prepared by methods known in the art or by modifications thereof (for example see Millward, *J. Chem. Soc.* 26 (1960)). Treatment of (1) with (2) yields the cyclohexenol (3). Treatment of (3) with peroxide and acid, as taught in U.S. Pat. No. 4,486,219 yields alcohol (4). Reaction of (4) with a reducing agent, such as lithium aluminum hydride, followed by treatment with a base, such as triethylamine, and toluenesulfonyl chloride at ambient temperature to 100° C. produces the corresponding monotosylate. Oxidation of the alcohol yields ketone (5). Treatment of (5) with a strong base, such as lithium diisopropylamide, followed by reduction of the ketone with a reducing agent, such as sodium borohydride, produces Ia.

Scheme 3

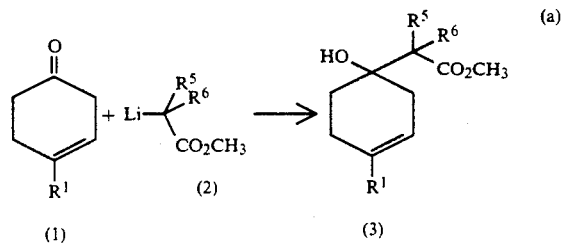

-continued
Scheme 3

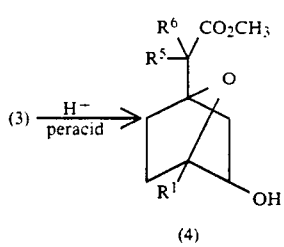

(3) $\xrightarrow[\text{peracid}]{H^-}$ (4)

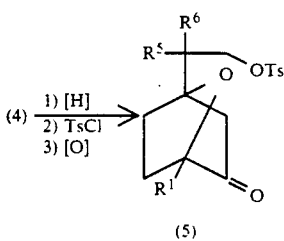

(4) $\xrightarrow[\substack{1)\ [H] \\ 2)\ TsCl \\ 3)\ [O]}]{}$ (5)

(5) $\xrightarrow[\substack{1)\ \text{base} \\ 2)\ [H]}]{}$ Ia  (d)

Alternatively, compounds of Formula I can be prepared through the sequence shown in Scheme 4. Cyclohexenone (1) can be converted to hydroxy ester (6) by treatment with hydrogen cyanide, following by hydrochloric acid in methanol using the procedure of Hook, Mander and Urech, *J. Org. Chem.*, 49, 3250 (1984) or modifications thereof. Treatment of alcohol (6) with peracid and acid as described in Scheme 3 yields the bicyclic alcohol (7). Treatment of the ester with a reducing agent, such as lithium aluminum hydride or a Grignard reagent (e.g., $R^5M$), followed by tosylation and oxidation of the alcohol yields bicyclic ketone (8). Treatment of (8) with strong base, such as lithium diisopropylamide, followed by reduction of the ketone yields alcohol Ia.

Scheme 4

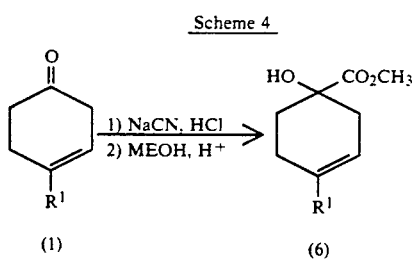

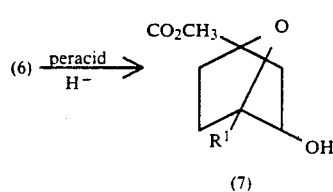

-continued
Scheme 4

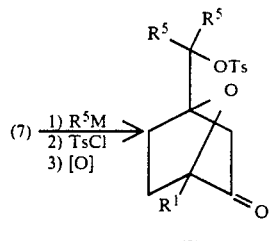

(7) $\xrightarrow[\substack{1)\ R^5M \\ 2)\ TsCl \\ 3)\ [O]}]{}$ (8)

(8) $\xrightarrow[\substack{1)\ \text{base} \\ 2)\ [H]}]{}$ Ia  (d)

Compounds of Structure IIa can be prepared through the sequence shown in Scheme 5, or by modifications thereof. Compound (9) can be prepared by methods known in the art (for example see Veselovsky, Gybin, Lozanova, Moiseenkov, Smit and Caple, *Tet. Lett.*, 175 (1988)). Alcohol IIa can be prepared from (9) using the sequence of reactions described in Scheme 3 or by modifications thereof.

Alternatively, compounds of Structure IIa can be prepared through the sequence shown in Scheme 6. Compound IIa can be prepared from (9) using the sequence of reactions described in Scheme 4 or by modifications thereof.

Compounds of Structure IIIa can be prepared by the sequence shown in Scheme 7. Diels-Alder reaction of (16) and (17) yields cyclohexene (18) (where X=halogen, tosylate or the like and m=1-4). Addition of a Grignard reagent (e.g., $R^3M$) or a reducing agent followed by treatment with peracid and acid as described in Scheme 4 gives alcohol (19). Oxidation of the alcohol to the ketone, followed by treatment with a strong base, such as lithium diisopropyl amide and subsequent reduction of the ketone yields IIIa.

Scheme 5

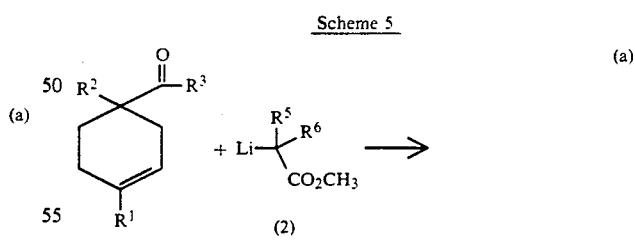

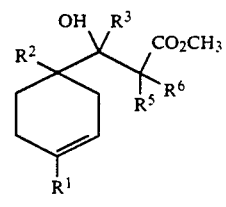

Scheme 5

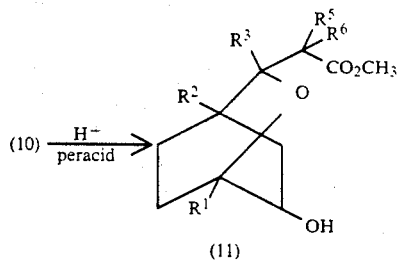

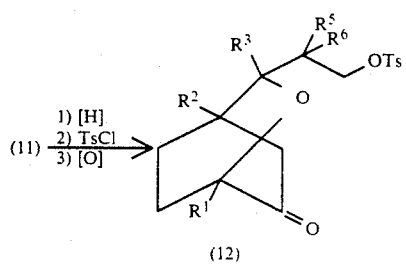

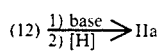

Scheme 6

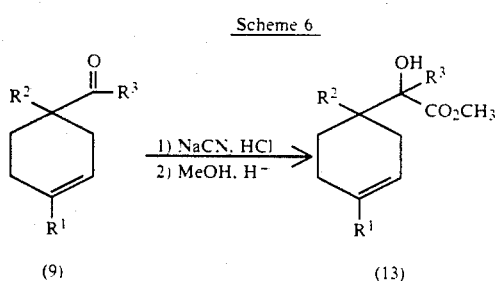

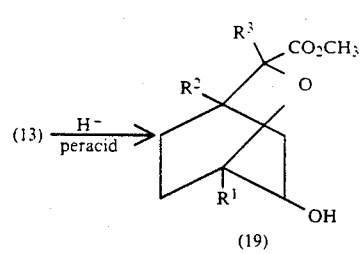

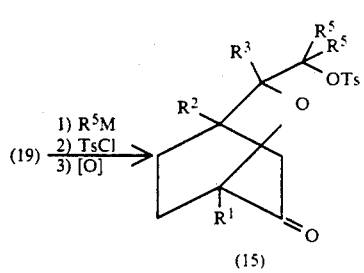

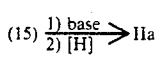

Scheme 7

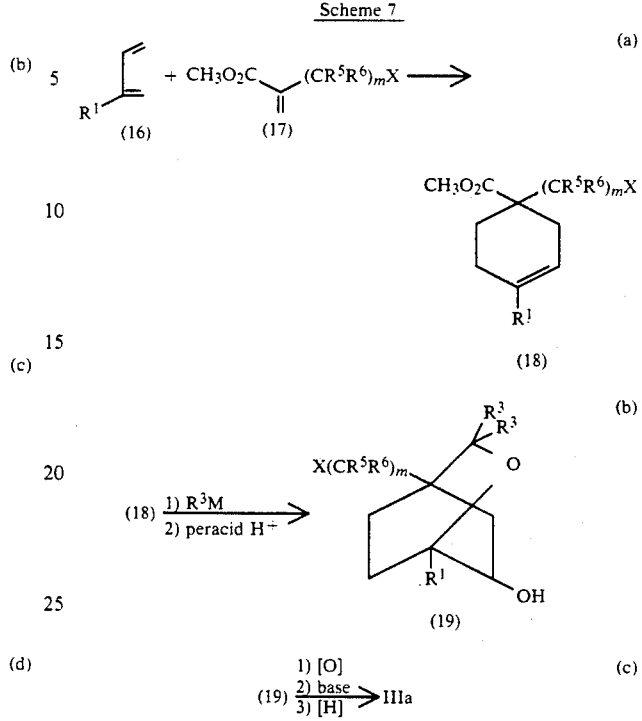

Compounds of Structure IVa can be prepared using the sequence shown in Scheme 8. Compound (20) can be prepared by methods known in the art (for example see Buchi and Powell, J. Amer. Chem. Soc., 3126 (1970)). Conversion of (20) to IVa can be accomplished using the sequence of reactions described in Scheme 3 or by modifications thereof.

Compounds of Structure IVa can also be prepared using the sequence shown in Scheme 9 and described in Scheme 4.

Compounds of Structure Va can be prepared using the sequence shown in Scheme 10. Diels-Alder reaction of (25) and (26) yields cyclohexene (27), where X=halogen, tosylate or the like. Alcohol Va can be prepared from (27) using reactions like those described in Scheme 7 or by modifications thereof.

Alternatively, compounds of Structure Va can be prepared using the sequence shown in Scheme 11. Diels-Alder adduct (29) can be reduced with a reducing agent such as lithium aluminum hydride or reacted with a Grignard reagent (e.g., $R^3M$). The resulting alcohol can be treated with peracid under acidic conditions to generate the bicyclic dialcohol. Tosylation of the primary alcohol and oxidation of the secondary alcohol yields (30). Treatment with a strong base, such as lithium diisopropyl amide, and subsequent reduction of the ketone yields Va.

Compounds of Structure VIa can be prepared using the sequence shown in Scheme 12. Ketone (31) can be prepared by methods known in the art (for example see Buchi and Powell, J. Amer. Chem. Soc., 92, 3126 (1970)). Alkylation of (31) with a suitable electrophile (X=halogen, tosylate or the like) yields (32). Alcohol VIa can be prepared from (32) using the sequence of reactions described in Scheme 7 or by modifications thereof.

Scheme 8
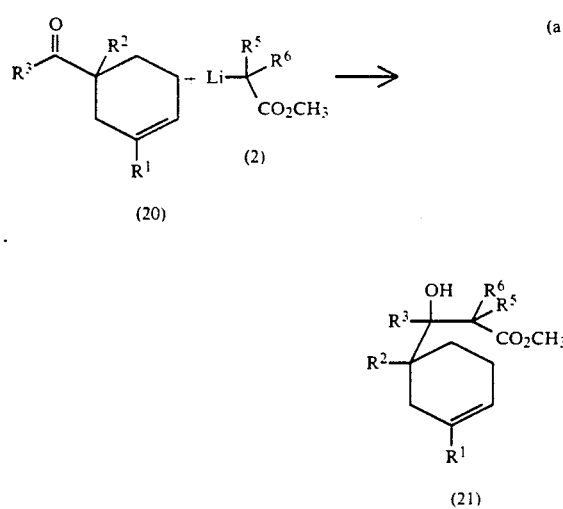
Scheme 9
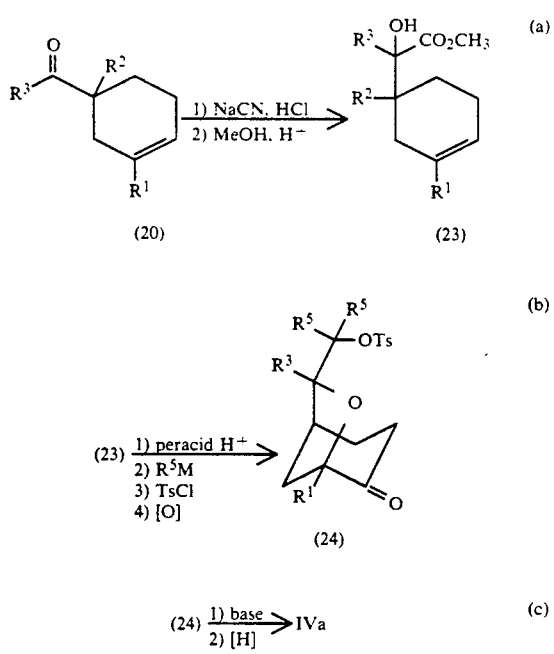
Scheme 10
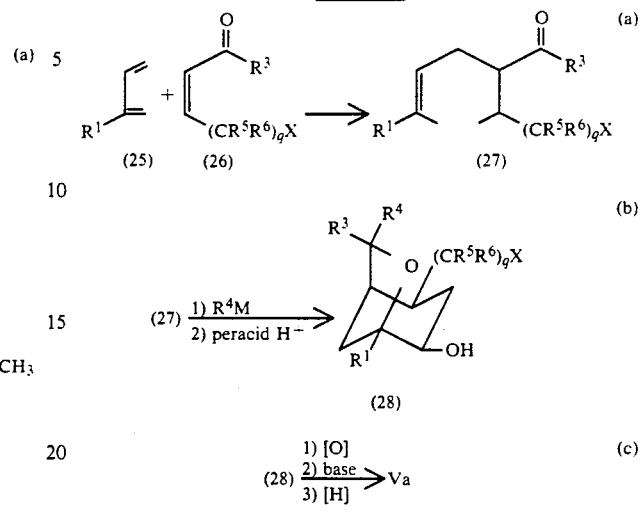
Scheme 11
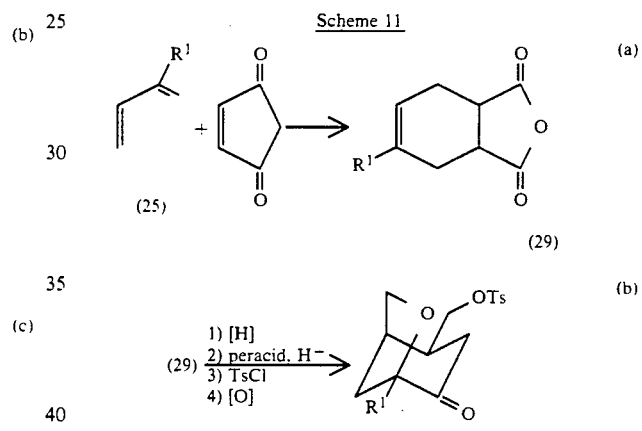
Scheme 12
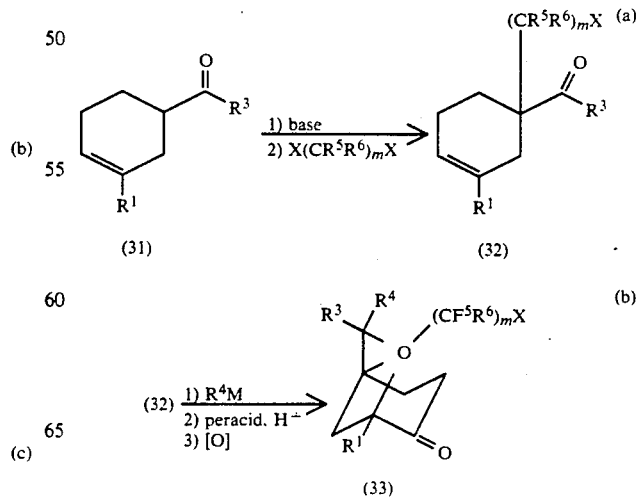

-continued

Scheme 12

(33) →(1) base, 2) [H]→ VIa    (c)

The following examples further illustrate the invention:

EXAMPLE 1

(1α,2α,4α,5β,6α)-(+/−)-5-((2,6,-difluorophenyl)methoxy)-6-methyl-7-oxatricyclo[4.2.1.$^{2,4}$]nonane

Step A: (±)-4-Methyl-4-cyclohexene-1,2-dicarboxylic anhydride

To 50 ml (0.50 mol) of isoprene was added 25 g (0.26 mol) of maleic anhydride portionwise with cooling. The reaction mixture was stirred at ambient temperature for four hours. The excess isoprene was removed under vacuum to give 40.5 g of a white solid, m.p. 63°–65° C.

NMR (CDC$l_3$): δ 5.70 (br s,1H , 3.45 (m,2H), 2.50 (m,4H), 1.81 (s,3H).

IR (KBr): 2900, 1840, 1770, 1445, 1235, 965, 920, 800 cm$^{-1}$.

Step B: (±)-Cis-4-methyl-4-cyclohexene-1,2-dimethanol

To 300 ml of tetrahydrofuran at 0° C. was added 16.0 g (0.42 mol) lithium aluminum hydride portionwise keeping the reaction temperature between 0° C. and 5° C. A solution of 33.0 g (0.20 mol) of 4-methyl-4-cyclohexene-2,3-dicarboxylic anhydride in 100 ml of tetrahydrofuran was added dropwise over 2 hours keeping the temperature between 0° C. and 10° C. The reaction mixture was warmed to ambient temperature and stirred for 2 hours. The reaction was cooled to 0° C. and 35 ml of ethyl acetate was added dropwise, followed by dropwise addition of 35 ml isopropanol and 35 ml water. The reaction mixture was filtered through celite using acetone, dried with MgSO$_4$, filtered, and concentrated to 33.0 g of oil. Flash chromatography in 3:1 hexanes-ethylacetate, followed by 1:1 hexanes-ethylacetate and finally ethylacetate alone yielded 18.2 g of oil.

NMR (CDCl$_3$): δ 5.35 (br s,1H), 3.68 (m,2H), 3.60 (m,2H), 3.10 (br s,2H) ,2.05 (br s,6H), 1.64 (s,3H).

IR (neat): 3500–3100, 1730w, 1440, 1010 cm$^{-1}$.

MS (CI): 157 (M+1), 139,121.

Step C: 2-endo,4-exo-(±)-4-hydroxy55-methyl-6-oxabicyclo[3.2.1]octane-2-methanol To a suspension of 39.0 g (0.124 mol) of 55% m-chloroperbenzoic acid in 400 ml of methylene-chloride at 0° C. was added 19.4 g (0.124 mol) of (±)-cis-4-methyl-1,4-cyclohexene-1,2-dimethanol in 100 ml of methylene chloride over 15 minutes keeping the temperature less than 8° C. The reaction mixture was warmed to ambient temperature and stirred for 24 hours. The reaction was cooled to 0° C. and 30 ml of a saturated aqueous solution of Na$_2$S$_2$O$_3$ was added dropwise keeping the temperature less than 8° C. The reaction mixture was dried with MgSO$_4$, filtered, and concentrated under reduced pressure. Flash chromatography in 3:1 hexanes-ethylacetate, 1:1 hexanes-ethylacetate, then ethylacetate alone yielded 6.1 g oily solid.

NMR (CDCl$_3$): δ 3.80 (br d,2H), 3.60 (br d,1H), 3.45 (d,2H), 2.70 (br s,2H), 2.42 (br s,1H), 2.0 (m), 1.5 (m), 1.33 (s,3H).

IR (neat): 3400–3200, 2900, 1450, 1380, 1060, 1000, 820 cm$^{-1}$.

MS (CI): 173 (M+1), 213,155.

Step D: 2-endo,4-exo-(+/−)-[4-hydroxy-5-methyl-6-oxabicyclo[3.2.1]-octan-2-yl)methyl 4-methylbenzenesulfonate To 14.9 g (0.086 mol) of 2-endo-4-exo-(±)-4-hydroxy-5-methyl-6-oxabicyclo[3.2.1]octane-2-methanol in 25 ml of pyridine at 0° C. was added 18.06 g (0.095 mol) of p-toluene-sulfonylchloride portionwise keeping the temperature less than 5° C. The reaction was stirred at 0° C. for 10 minutes, then 0.97 g (0.008 mol) 4-dimethylaminopyridine was added. The reaction was warmed to ambient temperature and stirred for 6 hours. An additional 9.00 g of p-toluenesulfonyl chloride and 1.00 g of 4-dimethylamino pyridine were added and the reaction mixture was stirred for 72 hours. To the reaction was added 20 ml water. The mixture was extracted twice with ether and then twice with methylene chloride. The combined organic layers were dried, filtered, and concentrated under reduced pressure. Flash chromatography using 3:1 hexanes-ethylacetate, then 1:1 hexanes-ethylacetate yielded 21.03 g of white solid, m.p. 87°–89° C.

NMR (CDCl$_3$): δ 7.75 d(2H), 7.38 d(2H), 3.83 d(2H), 3.6 m(3H), 2.46 s(3H), 2.38 m(1H), 2.21 m(1H), 1.5 m, 1.30 s(3H).

IR (neat): 3440 br, 2950, 2900, 1609, 1459, 1360, 1190, 1180, 1070, 1050, 960, 830, 820, 680 cm$^{-1}$.

MS (CI): 327 (m+1), 344, 309.

Step E: 2-endo-(+/−)-5-methyl-2-[[[(4-methylphenyl)sulfonyl]oxy]-methyl]-6-oxabicyclo[3.2.1]-octan-4-one To 64.5 ml (0.13 mol) of 2M oxalyl chloride in methylene chloride at −78° C. was added dropwise 13.7 ml (0.19 mol) dimethyl sulfoxide in 20 ml methylene chloride. The reaction was stirred for 10 minutes, then 21.03 g (0.06 mol) of 2-endo,4-exo(+/−)-[4-hydroxy-5-methyl-6-oxabicyclo[3.2.1]-octan-2-yl]methyl 4-methyl benzenesulfonate in 50 ml methylene chloride was added dropwise to the reaction mixture. The reaction was stirred at −78° C. for 45 minutes, then 40.5 ml (0.29 mol) of triethylamine in 40 ml of methylene chloride was added dropwise. The reaction mixture was warmed to ambient temperature and stirred for 20 hours. To the reaction was added 50 ml water. The reaction was extracted with methylene chloride. The organic layer was washed with water, dried over MgSO$_4$, filtered, and concentrated under reduced pressure. Flash chromatography in 3:1 hexanes-ethylacetate, followed by 1:1 hexanes-ethylacetate yielded 19.49 g of white solid, m.p. 104°–106° C.

NMR (CDCl$_3$): δ 7.80 d(2H), 7.37 d(2H), 3.95 m(4H), 2.62 m(1H), 2.47 s(3H), 2.4–2.0 m, 1.80 d(1H), 1.32 s(3H).

IR (neat): 2950 br, 1730, 1605, 1365, 1190, 1102, 970, 950, 840, 810, 670, 560, 525 cm$^{-1}$.

MS (CI): 342 (M+NH$_4^+$).

Step F: 1α,2α,4α,6α)-6-methyl-7-oxatricyclo[4.2.1.0$^{2,4}$]nonan-5one

To 2.38 ml (0.017 mol) diisopropylamine in 10 ml tetrahydrofuran at −78° C. was added dropwise 6.17 ml (0.015 mol) 2.5M butyllithium in hexanes. The reaction mixture was warmed in −20° C. and then cooled back to −78° C. To this solution was added dropwise 5.0 g (0.015 mol) 2-endo-(+/−)-5-methyl-2-[[[(4-methylphenyl)sulfonyl]oxy]-methyl]-6-oxabicyclo[3.2.1]-octan-4-one in 10 ml tetrahydrofuran. The reaction mixture was allowed to warm to ambient temperature and stirred for four hours. The reaction was cooled to 0° C. and 50 ml of isopropanol was added. Ether was added and organic layer was washed with water, dried over MgSO$_4$, filtered, and concentrated to an oil. Flash chromatography in 20:1 hexanes:ethylacetate, followed by 6:1 hexanes:ethylacetate yielded 1.32 g of oil.

$^1$H NMR (CDCl$_3$): δ 3.78 (dd,1H), 3.71 (d,1H), 2.8 (dd,1H), 2.0 (m,3H), 1.60 (ddd,1H), 1.44 (dd,1H), 1.11 ddd(1H), 1.32 s 3H.

$^{13}$C NMR (CDCl$_3$): δ 18.47 (CH$_3$), 15.14 (CH$_2$), 46.59 (CH$_2$), 71.76 (CH$_2$), 21.15 (CH), 25.14 (CH), 34.24 (CH), 84.58 (C), 206.91 (C=O).

IR (neat): 3000–2860, 1695 (s), 1440, 1335, 1260, 1150, 1105, 1010, 972, 810 cm$^{-1}$.

GCMS: 152 (M.$^+$).

Step G:
(1α,2α,4α,5β,6α)-6-methyl-7-oxatricyclo[4.2.1.0$^{2,4}$]-non-5-ol

To 1.21 g (0 0080 mol) of (1α,2α,4α,6α)-6-methyl-7-oxatricyclo[4.2.1.0$^{2,4}$]nonan-5-one in 10 ml tetrahydrofuran at −78° C. was added 8.76 ml (0.0088 mol) of 1M Super Hydride ®. The reaction mixture was warmed to ambient temperature, then cooled to −78° C. An additional 4.0 ml (0.004 mol) of 1M Super Hydride ® was added. The reaction mixture was warmed to 0° C. and quenched with 20 ml of water. The reaction mixture was extracted twice with ether and twice with methylene chloride. The combined organic layers were dried over MgSO$_4$, filtered and concentrated. Flash chromatography in 6:1 hexanes:ethylacetate, followed by 3:1 hexanes:ethylacetate yielded 1 16 g oil.

NMR (CDCl$_3$): δ 4.4 (brs,1H), 3.78 (dd,1H), 3.60 (dd,1H), 3.48 (d,1H), 2.60 (m,1H), 2.00 (d,1H), 1.6 (m,2H), 1.33 (s,3H), 1.20 (m,1H), 0.9 (m,1H), 0.55 (m,1H).

IR (neat): 3400 (br), 3000–2860, 1350, 1230, 1060, 1010, 962, 795 cm$^{-1}$.

GCMS: 154 (M.$^+$).

Step H:
(1α,2α,4α,5β,6α)-(+/−)-5-((2,6-difluorophenyl)methoxy))-6-methyl-7-oxatricyclo-[4.2.1.0$^{4,2}$]-nonane To 0.06 g (0.0016 mol) hexane-washed 60% sodium hydride was added 20 ml tetrahydrofuran at 0° C. To this suspension was added 0.20 g (0.0013 mol) (1α,2α,-4α,5β,6α)-6-methyl-7-oxatricyclo[4.2.1.0$^{2,4}$]-non-5-ol in tetrahydrofuran. After 10 minutes, 0.32 g (0.0016 mol) 2-fluorobenzylbromide was added. The reaction mixture was stirred for 24 hours at ambient temperature, then 20 ml water was added. The reaction mixture was extracted twice with ether and twice with methylene chloride. The combined organic layers were dried over MgSO$_4$, filtered, and concentrated. Flash chromatography in 6:1 hexanes:ethylacetate yielded 0.22 g of oil.

$^1$H NMR (CDCl$_3$): δ 7.22 (m,1H), 6.85 (dd,2H), 4.89 (d,1H), 4.67 (d,1H), 3.59 (dd,1H), 3.50 (d,2H), 2.59 (m,1H), 1.61 (dq,1H), 1.50 (d,2H), 1.23 (s,3H), 1.16 (m,1H), 0.89 (q,1H), 0.59 (dt,1H).

$^{13}$CNMR (CDCl$_3$): δ 23.06 (CH$_3$), 7.21 (CH$_2$), 41.93 (CH$_2$), 56.92 (CH$_2$), 70.78 (CH$_2$), 11.02 (CH), 22.22 (CH), 34.05 (CH), 79.40 (CH), 111.1 (CH), 129 7 (CH), 81.09 (C), 161.05 (C), 163,57 (C).

MS(DCI/NH$_3$): 282 (M+H$^+$), 299 (M+NH$_4$$^-$), 137.

EXAMPLE 2

(1α,2α,5α,6α)-(+/−)-5-((2-chloro-6-fluorophenyl)-methoxy))-6-methyl-7-oxatricyclo[4.2.1.0$^{2,4}$]-nonane To 0.1 g (2.1 mmol) of hexane-washed 60% sodium hydride in tetrahydrofuran was added 0.3 g (2.0 mmol) of (1α,2α,5α,5β,6α)-6-methyl-7-oxatricyclo[4.2.1.0$^{2,4}$]-nonan-5-ol. After 10 minutes, 0.26 ml (2.1 mmol) of 2-chloro-6-fluorobenzyl bromide was added. The reaction mixture was heated 70° C. When the reaction was complete water was added and the reaction mixture was extracted twice with ether. The combined organic extracts were dried over MgSO$_4$, filtered, and concentrated. Flash chromatography in 20:1 hexanes:ethylacetate yielded 0.26 g solid, m.p. 69°–71° C.

$^1$H NMR (CDCl$_3$): δ 7.2 (m,2H), 6.99 (m,1H), 4.95 (d,1H), 4.72 (d,1H), 3.6 (dd,1H), 3.5 (d,2H), 2.60 (m,1H),1.6 (m,1H), 1.49 (dd,2H),1.25 (s,3H), 1.20 (m,1H), 0.90 (m, 1H), 0.60 (m, 1H).

$^{13}$CNMR (CDCl$_3$): δ 23.1 (CH$_3$), 7.2 (CH$_2$), 42.9 (CH$_2$), 60.0 (CH$_2$), 70.7 (CH$_2$), 11.0 (CH), 22.1 (CH), 34 (CH), 79.4 (CH), 113.8 (CH), 125.2 (CH), 129.7 (CH), 81.0 (C), 124.1 (C), 129.4 (C), 136.8 (C), 162 (C).

MS(DCI/NH$_3$): 297 (MH$^+$), 299 (MH$^-$), 314 (MNH$_4$$^-$), 316 (MNH$_4$$^+$).

EXAMPLE 3

(1α,2α,5β,6α)-(+/−)-5-((2-chloro-6-fluorophenyl)methoxy)-6-ethyl-7-oxatricyclo[4.2.1.0$^{2,4}$]nonane Step A: (±)-4-Ethyl-4-cyclohexene-1,2-dicarboxylic anhydride Maleic anhydride (19.6 g, 0.2 mol) and 20 g (0.24 mol) 2-ethyl-1,3-butadiene were stirred at ambient temperature for 24 hours. The excess 2-ethyl-1,3-butadiene was removed in vacuo to yield 36 g of white solid, m.p. 65°–67° C.

IR (KBr): 2980–2860, 1835, 1770, 1235, 980, 930 cm$^{-1}$.

Step B:
2-endo,4-exo-(+/−)-4-hydroxy-5-ethyl-6-oxabicyclo-[3.2.1]octane-2-methanol To 16 g (0.42 mol) lithium aluminum hydride in 200 ml tetrahydrofuran at 0° C., was added 33.0 g (0.2 mol) (+/−)-4-ethyl-4-cyclohexene-1,2-dicarboxylic anhydride dropwise over 45 minutes keeping the temperature less than 5° C. The reaction was warmed to ambient temperature and stirred for 24 hours. The reaction was quenched at 0° C. by sequential addition of ethyl acetate, isopropanol, and water. The mixture was filtered through celite with acetone, dried over MgSO$_4$, filtered, and concentrated under reduced pressure. The resulting oil was dissolved in methylene chloride and cooled to 0° C. A solution of 33.6 g (0.11 mol) m-chloroperbenzoic acid was added keeping the temperature less than 5° C. The reaction was warmed to ambient temperature and stirred for 72 hours. A solution of saturated sodium thiosulfate was added, the mixture was dried over MgSO$_4$, filtered, and concentrated under reduced pressure. Flash chromatography in 3:1 hexanes-ethylacetate, followed by 1:1 hexanes-ethylacetate, followed by ethylacetate yielded 11.60 g of product.

NMR (CDCl$_3$): δ 3.8 m(4H), 3.48 d(2H), 2.42 br t(1H), 2.2-1.5 m, 0.94 t(3H).

Step C:
2-endo,4-exo(+/−)-[4-hydroxy-5-ethyl-6-oxabicyclo-[3.2.1]octan-2-yl]methyl 4-methylenebenzene sulfonate To 11.06 g (0.06 mol) of 2-endo,4-exo-(+/−)-4-hydroxy-5-ethyl-6-oxabicyclo[3.2.1]octane-2-methanol in pyridine at 0° C. was added 13.6 9 (0.07 mol) p-toluene-sulfonyl chloride portionwise. The reaction was stirred for 10 minutes, then a catalytic amount of dimethylaminopyridine was added. The reaction was stirred for 24 hours. Ether was added, and the reaction was washed sequentially with water, 10% HCl, and water, then dried over MgSO$_4$, filtered, and concentrated under reduced pressure. Flash chromatography in 3:1 hexanes-ethylacetate, then 1:1 hexane-ethylacetate yielded 10.5 g of product.

NMR (CDCl$_3$): δ 7.76 d(2H), 7.33 d(2H), 3.83 d(2H), 3.63 m(3H), 2.3 m(2H), 2.45 s(3H), 1.98 d(1H), 1.7-1.4 m, 0.91 t(3H).

Step D:
(2-endo-5-ethyl-2-[[[(4-methylphenyl)sulfonyl]oxy]methyl]-6-oxabicyclo[3.2.1]octan-4-one Swern oxidation (using the conditions described in Example 1, Step E), with 5.87 g (0.017 mol) of 2-endo,4-exo-(+/−)-[4-hydroxy-5-ethyl-6-oxabicyclo[3.2.1]octan-2-yl]methyl 4-methylbenzene sulfonate, 17.4 ml (0.035 mol) of 2M oxalylchloride in methylene chloride, 3.7 ml (0.052 mol) dimethylsulfoxide, and 10.9 ml (0.078 mol) triethylamine yielded 7.17 g.

NMR (CDCl$_3$): δ 7.78 (d,2H), 7.37 (d,2H), 3.92 (m,4H), 2.62 (m,1H), 2.47 (s,3H), 2.3 (m,3H), 2.20 (dd,1H), 1.7 (m,2H), 1.61 (d,1H), 0.91 (t,3H).

Step E:
(1α,2α,4α,5β,6α)-6-ethyl-7-oxatricyclo[4.2.1.0$^{2,4}$]-non-5-ol

Treatment with lithium diisopropylamine (using the conditions described in Example 1, Step F) with 6.0 g (0.018 mol) of (2-endo)-5-ethyl-2-[[[(4-methylphenyl)-sulfonyl]oxy]-methyl]-6-oxabicyclo[3.2.1]octan-4-one, 2.74 ml (0.02 mol) diisopropylamine, and 7.1 ml (0.018 mol) 2.5 M butyllithium in hexanes gave 1.65 g of the tricyclic ketone.

NMR (CDCl$_3$): δ 3.74 (s,2H), 2.8 (d,1H), 2.0 (m,3H), 1.78 (q,1H), 1.60 (m,1H), 1.42 (q,1H), 1.10 (m,1H), 0.90 (t,3H).

Treatment of the above compound with Super Hydride ® (13.6 ml, 0.014 mol) as described in Example 1, Step G gave 1.73 g oil.

NMR (CDCl$_3$): δ 3.83 (dd,1H), 3.55 (dd,1H), 3.54 (d,1H), 2.6Q (m,1H), 1.92 (d,1H), 1.8-1.5 (m,3H), 1.40 (d,1H), 1.22 (m,1H), 0.96 (m,1H), 0.86 (t,3H), 0.61 (q,1H).

Step F:
(1α,2α,5β,6α)-(+/−)-5-((2-chloro-6-fluorophenyl)methoxy))-6-ethyl-7-oxatricyclo[4.2.1.0$^{4,2}$]-nonane (1α,2α,5β,6α)-6-ethyl-7-oxatricyclo[4.2.1.0$^{2,4}$]-nonan-5-ol (0.2 g, 0.0011 mol) was treated with 0.05 g (0.0013 mol) 60% sodium hydride and 0.16 ml (0.0013 mol) 2-chloro-6-fluorobenzylbromide using the conditions described in Example 2 to give 0.22 g white solid, m.p. 73°-75° C.

NMR (CDCl$_3$): δ 7.18 (m,2H), 6.98 (m,1H), 4.91 (d,1H), 4.81 (d,1H), 3.59 (d,1H), 3.53 (m,2H), 2.59 (m,1H), 1.7-1.4 (m,4H), 1.3 (d,1H), 1.21 (m,1H), 0.91 (m,1H), 0.65 (t,3H), 0.64 (m,1H).

IR (KBr): 2950, 2850, 1600, 1572, 1450, 1072, 980, 770 cm$^{-1}$.

MS: 281 (M$^+$-Et), 143.

Utilizing the above disclosure the following compounds can be prepared:

TABLE 1

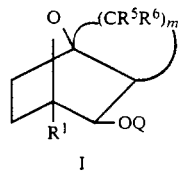

I

| m | Q | m | Q |
|---|---|---|---|
| | R$^1$=CH$_3$, R$^5$=R$^6$=H | | |
| 1 | CH$_2$(C$_6$H$_5$) | 2 | CH$_2$(C$_6$H$_5$) |
| 1 | CH$_2$(2-FC$_6$H$_4$) | 2 | CH$_2$(2-FC$_6$H$_4$) |
| 1 | CH$_2$(2,6-F$_2$C$_6$H$_3$) | 2 | CH$_2$(2,6-F$_2$C$_6$H$_3$) |
| 1 | CH$_2$(2-ClC$_6$H$_4$) | 2 | CH$_2$(2-ClC$_6$H$_4$) |
| 1 | CH$_2$(2,6-Cl$_2$C$_6$H$_3$) | 2 | CH$_2$(2,6-Cl$_2$C$_6$H$_3$) |
| 1 | CH$_2$(2-Cl,6-FC$_6$H$_3$) | 2 | CH$_2$(2-Cl,6-FC$_6$H$_3$) |
| 1 | CH$_2$(2-BrC$_6$H$_4$) | 2 | CH$_2$(2-BrC$_6$H$_4$) |
| 1 | CH$_2$(2,6-Br$_2$C$_6$H$_3$) | 2 | CH$_2$(2,6-Br$_2$C$_6$H$_3$) |
| 1 | CH$_2$(2-(CH$_3$)C$_6$H$_4$) | 2 | CH$_2$(2-(CH$_3$)C$_6$H$_4$) |
| 1 | CH$_2$(2-pyridyl) | 2 | CH$_2$(2-pyridyl) |
| 1 | CH$_2$(2-thienyl) | 2 | CH$_2$(2-thienyl) |
| 1 | CH$_2$—(2-furanyl) | 2 | CH$_2$—(2-furanyl) |
| 1 | CH$_2$(2-tetrahydrofuranyl) | 2 | CH$_2$(2-tetrahydrofuranyl) |
| 1 | CH$_2$(2-tetrahydropyranyl) | 2 | CH$_2$(2-tetrahydropyranyl) |
| 1 | Q-1 | 2 | Q-1 |
| 1 | Q-3 | 2 | Q-3 |
| 1 | Q-4 | 2 | Q-4 |
| 1 | Q-6 | 2 | Q-6 |
| 1 | Q-7 | 2 | Q-7 |
| 1 | Q-8 | 2 | Q-8 |
| 1 | Q-15 | 2 | Q-15 |

TABLE 1-continued

| | | | |
|---|---|---|---|
| 1 | $CH_2(2-(OCH_3)C_6H_4)$ | 2 | $CH_2(2-(OCH_3)C_6H_4)$ |
| 1 | $CH_2(2,4-F_2C_6H_3)$ | 2 | $CH_2(2,4-F_2C_6H_3)$ |
| 1 | $CH_2(2-(CN)C_6H_4)$ | 2 | $CH_2(2-(CN)C_6H_4)$ |
| 1 | $CH_2(2-(CF_3)C_6H_4)$ | 2 | $CH_2(2-(CF_3)C_6H_4)$ |
| 1 | $CH_2(2-(CH=CH_2)C_6H_4)$ | 2 | $CH_2(2-(CH=CH_2)C_6H_4)$ |
| 3 | $CH_2(C_6H_5)$ | 4 | $CH_2(C_6H_5)$ |
| 3 | $CH_2(2-FC_6H_4)$ | 4 | $CH_2(2-FC_6H_4)$ |
| 3 | $CH_2(2,6-F_2C_6H_3)$ | 4 | $CH_2(2,6-F_2C_6H_3)$ |
| 3 | $CH_2(2-ClC_6H_4)$ | 4 | $CH_2(2-ClC_6H_4)$ |
| 3 | $CH_2(2,6-Cl_2C_6H_3)$ | 4 | $CH_2(2,6-Cl_2C_6H_3)$ |
| 3 | $CH_2(2-Cl,6-FC_6H_3)$ | 4 | $CH_2(2-Cl,6-FC_6H_3)$ |
| 3 | $CH_2(2-BrC_6H_4)$ | 4 | $CH_2(2-BrC_6H_4)$ |
| 3 | $CH_2(2,6-Br_2C_6H_3)$ | 4 | $CH_2(2,6-Br_2C_6H_3)$ |
| 3 | $CH_2(2-(CH_3)C_6H_4)$ | 4 | $CH_2(2-(CH_3)C_6H_4)$ |
| 3 | $CH_2(2-pyridyl)$ | 4 | $CH_2(2-pyridyl)$ |
| 3 | $CH_2(2-thienyl)$ | 4 | $CH_2(2-thienyl)$ |
| 3 | $CH_2(2-furanyl)$ | 4 | $CH_2(2-furanyl)$ |
| 3 | $CH_2(2-tetrahydrofuranyl)$ | 4 | $CH_2(2-tetrahydrofuranyl)$ |
| 3 | $CH_2(2-tetrahydropyranyl)$ | 4 | $CH_2(2-tetrahydropyranyl)$ |
| 3 | Q-1 | 4 | Q-1 |
| 3 | Q-3 | 4 | Q-3 |
| 3 | Q-4 | 4 | Q-4 |
| 3 | Q-6 | 4 | Q-6 |
| 3 | Q-7 | 4 | Q-7 |
| 3 | Q-8 | 4 | Q-8 |
| 3 | Q-15 | 4 | Q-15 |
| 3 | $CH_2(2-(OCH_3)C_6H_4)$ | 4 | $CH_2(2-(OCH_3)C_6H_4)$ |
| 3 | $CH_2(2,4-F_2C_6H_3)$ | 4 | $CH_2(2,4-F_2C_6H_3)$ |
| 3 | $CH_2(2-(CN)C_6H_4)$ | 4 | $CH_2(2-(CN)C_6H_4)$ |
| 3 | $CH_2(2-(CF_3)C_6H_4)$ | 4 | $CH_2(2-(CF_3)C_6H_4)$ |
| 3 | $CH_2(2-CH=CH_2)C_6H_4$ | 4 | $CH_2(2-CH=CH_2)C_6H_4$ |

$R^1=CH_3, R^5=R^6=CH_3$

| | | | |
|---|---|---|---|
| 1 | $CH_2(C_6H_5)$ | 3 | $CH_2(C_6H_5)$ |
| 1 | $CH_2(2-FC_6H_4)$ | 3 | $CH_2(2-FC_6H_4)$ |
| 1 | $CH_2(2,6-F_2C_6H_3)$ | 3 | $CH_2(2,6-F_2C_6H_3)$ |
| 1 | $CH_2(2-ClC_6H_4)$ | 3 | $CH_2(2-ClC_6H_4)$ |
| 1 | $CH_2(2,6-Cl_2C_6H_3)$ | 3 | $CH_2(2,6-Cl_2C_6H_3)$ |
| 1 | $CH_2(2-Cl,6-FC_6H_3)$ | 3 | $CH_2(2-Cl,6-FC_6H_3)$ |
| 1 | $CH_2(2-Cl,6-FC_6H_3)$ | 3 | $CH_2(2-Cl,6-FC_6H_3)$ |
| 1 | $CH_2(2-BrC_6H_4)$ | 3 | $CH_2(2-BrC_6H_4)$ |
| 1 | $CH_2(2-(CH_3)C_6H_4)$ | 3 | $CH_2(2-(CH_3)C_6H_4)$ |
| 1 | $CH_2(2-tetrahydrofuranyl)$ | 3 | $CH_2(2-tetrahydrofuranyl)$ |
| 1 | $CH_2(2-tetrahydropyranyl)$ | 3 | $CH_2(2-tetrahydrofuranyl)$ |
| 1 | $CH_2(2,4-F_2C_6H_3)$ | 3 | $CH_2(w,4-F_2C_6H_3)$ |
| 1 | $CH_2(2-(CH=CH_2)C_6H_4)$ | 3 | $CH_2(2-(CH=CH_2)C_6H_4)$ |
| 1 | Q-1 | 1 | Q-1 |
| 2 | $CH_2(C_6H_5)$ | 4 | $CH_2(C_6H_5)$ |
| 2 | $CH_2(2-FC_3H_4)$ | 4 | $CH_2(2-FC_3H_4)$ |
| 2 | $CH_2(2,6-F_2C_6H_3)$ | 4 | $CH_2(2,6-F_2C_6H_3)$ |
| 2 | $CH_2(2-ClC_6H_4)$ | 4 | $CH_2(2-ClC_6H_4)$ |
| 2 | $CH_2(2,6-Cl_2C_6H_3)$ | 4 | $CH_2(2,6-Cl_2C_6H_3)$ |
| 2 | $CH_2(2-Cl,6-F-C_6H_3)$ | 4 | $CH_2(2-Cl,6-F-C_6H_3)$ |
| 2 | $CH_2(2-BrC_6H_4)$ | 4 | $CH_2(2-BrC_6H_4)$ |
| 2 | $CH_2(2-(CH_3)C_6H_4)$ | 4 | $CH_2(2-(CH_3)C_6H_4)$ |
| 2 | $CH_2(2-tetrahydrofuranyl)$ | 4 | $CH_2(2-tetrahydrofuranyl)$ |
| 2 | $CH_2(2-tetrahydropyranyl)$ | 4 | $CH_2(2-tetrahydropyranyl)$ |
| 2 | $CH_2(2,4-F_2C_6H_3)$ | 4 | $CH_2(2,4-F_2C_6H_3)$ |
| 2 | $CH_2(2-(CH=CH_2)C_6H_4)$ | 4 | $CH_2(2-(CH=CH_2)C_6H_4)$ |
| 2 | Q-1 | 4 | Q-1 |

$R^1=CH_3, R^5=OCH_3, R^6=H$

| | | | |
|---|---|---|---|
| 1 | $CH_2(C_6H_5)$ | 3 | $CH_2(C_6H_5)$ |
| 1 | $CH_2(2-FC_6H_4)$ | 3 | $CH_2(2-FC_6H_4)$ |
| 1 | $CH_2(2,6-F_2C_6H_3)$ | 3 | $CH_2(2,6-F_2C_6H_3)$ |
| 1 | $CH_2(2-ClC_6H_4)$ | 3 | $CH_2(2-ClC_6H_4)$ |
| 1 | $CH_2(2,6-Cl_2C_6H_3)$ | 3 | $CH_2(2,6-Cl_2C_6H_3)$ |
| 1 | $CH_2(2-Cl,6-FC_6H_3)$ | 3 | $CH_2(2-Cl,6-FC_6H_3)$ |
| 1 | $CH_2(2-BrC_6H_4)$ | 3 | $CH_2(2-BrC_6H_4)$ |
| 1 | $CH_2(2-(CH_3)C_6H_4)$ | 3 | $CH_2(2-(CH_3)C_6H_4)$ |
| 1 | $CH_2(2-tetrahydrofuranyl)$ | 3 | $CH_2(2-tetrahydrofuranyl)$ |
| 1 | $CH_2(2-tetrahydropyranyl)$ | 3 | $CH_2(2-tetrahydropyranyl)$ |
| 1 | $CH_2(2,4-F_2C_6H_3)$ | 3 | $CH_2(2,4-F_2C_6H_3)$ |
| 1 | $CH_2(2-(CH=CH_2)C_6H_4)$ | 3 | $CH_2(2-(CH=CH_2)C_6H_4)$ |
| 1 | Q-1 | 1 | Q-1 |
| 2 | $CH_2(C_6H_5)$ | 4 | $CH_2(C_6H_5)$ |

TABLE 1-continued

| | | | |
|---|---|---|---|
| 2 | $CH_2(2-FC_3H_4)$ | 4 | $CH_2(2-FC_3H_4)$ |
| 2 | $CH_2(2,6-F_2C_6H_3)$ | 4 | $CH_2(2,6-F_2C_6H_3)$ |
| 2 | $CH_2(2-ClC_6H_4)$ | 4 | $CH_2(2-ClC_6H_4)$ |
| 2 | $CH_2(2,6-Cl_2C_6H_3)$ | 4 | $CH_2(2,6-Cl_2C_6H_3)$ |
| 2 | $CH_2(2-Cl,6-F-C_6H_3)$ | 4 | $CH_2(2-Cl,6-F-C_6H_3)$ |
| 2 | $CH_2(2-BrC_6H_4)$ | 4 | $CH_2(2-BrC_6H_4)$ |
| 2 | $CH_2(2-(CH_3)C_6H_4)$ | 4 | $CH_2(2-(CH_3)C_6H_4)$ |
| 2 | $CH_2(2$-tetrahydrofuranyl) | 4 | $CH_2(2$-tetrahydrofuranyl) |
| 2 | $CH_2(2$-tetrahydropyranyl) | 4 | $CH_2(2$-tetrahydropyranyl) |
| 2 | $CH_2(2,4-F_2C_6H_3)$ | 4 | $CH_2(2,4-F_2C_6H_3)$ |
| 2 | $CH_2(2-(CH=CH_2)C_6H_4)$ | 4 | $CH_2(2-(CH=CH_2)C_6H_4)$ |
| 2 | Q-1 | 4 | Q-1 |

$R^1=CH_3, R^5=OCH_3, R^6=CH_3$

| | | | |
|---|---|---|---|
| 1 | $CH_2(C_6H_5)$ | 3 | $CH_2(C_6H_5)$ |
| 1 | $CH_2(2-FC_6H_4)$ | 3 | $CH_2(2-FC_6H_4)$ |
| 1 | $CH_2(2,6-F_2C_6H_3)$ | 3 | $CH_2(2,6-F_2C_6H_3)$ |
| 1 | $CH_2(2-ClC_6H_4)$ | 3 | $CH_2(2-ClC_6H_4)$ |
| 1 | $CH_2(2,6-Cl_2C_6H_3)$ | 3 | $CH_2(2,6-Cl_2C_6H_3)$ |
| 1 | $CH_2(2-Cl,6-FC_6H_3)$ | 3 | $CH_2(2-Cl,6-FC_6H_3)$ |
| 1 | $CH_2(2-BrC_6H_4)$ | 3 | $CH_2(2-BrC_6H_4)$ |
| 1 | $CH_2(2-(CH_3)C_6H_4)$ | 3 | $CH_2(2-(CH_3)C_6H_4)$ |
| 1 | $CH_2(2$-tetrahydrofuranyl) | 3 | $CH_2(2$-tetrahydrofuranyl) |
| 1 | $CH_2(2$-tetrahydropyranyl) | 3 | $CH_2(2$-tetrahydropyranyl) |
| 1 | $CH_2(2,4-F_2C_6H_3)$ | 3 | $CH_2(2,4-F_2C_6H_3)$ |
| 1 | $CH_2(2-(CH=CH_2)C_6H_4)$ | 3 | $CH_2(2-(CH=CH_2)C_6H_4)$ |
| 1 | Q-1 | 1 | Q-1 |
| 2 | $CH_2(C_6H_5)$ | 4 | $CH_2(C_6H_5)$ |
| 2 | $CH_2(2-FC_3H_4)$ | 4 | $CH_2(2-FC_3H_4)$ |
| 2 | $CH_2(2,6-F_2C_6H_3)$ | 4 | $CH_2(2,6-F_2C_6H_3)$ |
| 2 | $CH_2(2-ClC_6H_4)$ | 4 | $CH_2(2-ClC_6H_4)$ |
| 2 | $CH_2(2,6-Cl_2C_6H_3)$ | 4 | $CH_2(2,6-Cl_2C_6H_3)$ |
| 2 | $CH_2(2-Cl,6-F-C_6H_3)$ | 4 | $CH_2(2-Cl,6-F-C_6H_3)$ |
| 2 | $CH_2(2-BrC_6H_4)$ | 4 | $CH_2(2-BrC_6H_4)$ |
| 2 | $CH_2(2-(CH_3)C_6H_4)$ | 4 | $CH_2(2-(CH_3)C_6H_4)$ |
| 2 | $CH_2(2$-tetrahydrofuranyl) | 4 | $CH_2(2$-tetrahydrofuranyl) |
| 2 | $CH_2(2$-tetrahydropyranyl) | 4 | $CH_2(2$-tetrahydropyranyl) |
| 2 | $CH_2(2,4-F_2C_6H_3)$ | 4 | $CH_2(2,4-F_2C_6H_3)$ |
| 2 | $CH_2(2-(CH=CH_2)C_6H_4)$ | 4 | $CH_2(2-(CH=CH_2)C_6H_4)$ |
| 2 | Q-1 | 4 | Q-1 |

$R^1=CH_2CH_3, R^5=R^6=H$

| | | | |
|---|---|---|---|
| 1 | $CH_2(C_6H_5)$ | 3 | $CH_2(C_6H_5)$ |
| 1 | $CH_2(2-FC_6H_4)$ | 3 | $CH_2(2-FC_6H_4)$ |
| 1 | $CH_2(2,6-F_2C_6H_3)$ | 3 | $CH_2(2,6-F_2C_6H_3)$ |
| 1 | $CH_2(2-ClC_6H_4)$ | 3 | $CH_2(2-ClC_6H_4)$ |
| 1 | $CH_2(2,6-Cl_2C_6H_3)$ | 3 | $CH_2(2,6-Cl_2C_6H_3)$ |
| 1 | $CH_2(2-Cl,6-FC_6H_3)$ | 3 | $CH_2(2-Cl,6-FC_6H_3)$ |
| 1 | $CH_2(2-BrC_6H_4)$ | 3 | $CH_2(2-BrC_6H_4)$ |
| 1 | $CH_2(2-(CH_3)C_6H_4)$ | 3 | $CH_2(2-(CH_3)C_6H_4)$ |
| 1 | $CH_2(2$-tetrahydrofuranyl) | 3 | $CH_2(2$-tetrahydrofuranyl) |
| 1 | $CH_2(2$-tetrahydropyranyl) | 3 | $CH_2(2$-tetrahydrofuranyl) |
| 1 | $CH_2(2,4-F_2C_6H_3)$ | 3 | $CH_2(2,4-F_2C_6H_3)$ |
| 1 | $CH_2(2-(CH=CH_2)C_6H_4)$ | 3 | $CH_2(2-(CH=CH_2)C_6H_4)$ |
| 1 | Q-1 | 1 | Q-1 |
| 2 | $CH_2(C_6H_5)$ | 4 | $CH_2(C_6H_5)$ |
| 2 | $CH_2(2-FC_3H_4)$ | 4 | $CH_2(2-FC_3H_4)$ |
| 2 | $CH_2(2,6-F_2C_6H_3)$ | 4 | $CH_2(2,6-F_2C_6H_3)$ |
| 2 | $CH_2(2-ClC_6H_4)$ | 4 | $CH_2(2-ClC_6H_4)$ |
| 2 | $CH_2(2,6-Cl_2C_6H_3)$ | 4 | $CH_2(2,6-Cl_2C_6H_3)$ |
| 2 | $CH_2(2-Cl,6-F-C_6H_3)$ | 4 | $CH_2(2-Cl,6-F-C_6H_3)$ |
| 2 | $CH_2(2-BrC_6H_4)$ | 4 | $CH_2(2-BrC_6H_4)$ |
| 2 | $CH_2(2-(CH_3)C_6H_4)$ | 4 | $CH_2(2-(CH_3)C_6H_4)$ |
| 2 | $CH_2(2$-tetrahydrofuranyl) | 4 | $CH_2(2$-tetrahydrofuranyl) |
| 2 | $CH_2(2$-tetrahydropyranyl) | 4 | $CH_2(2$-tetrahydropyranyl) |
| 2 | $CH_2(2,4-F_2C_6H_3)$ | 4 | $CH_2(2,4-F_2C_6H_3)$ |
| 2 | $CH_2(2-(CH=CH_2)C_6H_4)$ | 4 | $CH_2(2-(CH=CH_2)C_6H_4)$ |
| 2 | Q-1 | 4 | Q-1 |

TABLE 1-continued

TABLE 2

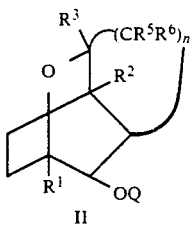

II

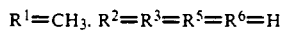
$R^1=CH_3, R^2=R^3=R^5=R^6=H$

| n | Q | n | Q |
|---|---|---|---|
| 2 | CH$_2$(C$_6$H$_5$) | 3 | CH$_2$(C$_6$H$_5$) |
| 2 | CH$_2$(2-FC$_6$H$_4$) | 3 | CH$_2$(2-FC$_6$H$_4$) |
| 2 | CH$_2$(2,6-F$_2$C$_6$H$_3$) | 3 | CH$_2$(2,6-F$_2$C$_6$H$_3$) |
| 2 | CH$_2$(2-ClC$_6$H$_4$) | 3 | CH$_2$(2-ClC$_6$H$_4$) |
| 2 | CH$_2$(2,6-Cl$_2$C$_6$H$_3$) | 3 | CH$_2$(2,6-Cl$_2$C$_6$H$_3$) |
| 2 | CH$_2$(2-Cl,6-FC$_6$H$_3$) | 3 | CH$_2$(2-Cl,6-FC$_6$H$_3$) |
| 2 | CH$_2$(2-BrC$_6$H$_4$) | 3 | CH$_2$(2-BrC$_6$H$_4$) |
| 2 | CH$_2$(2,6-Br$_2$C$_6$H$_3$) | 3 | CH$_2$(2,6-Br$_2$C$_6$H$_3$) |
| 2 | CH$_2$(2-(CH$_3$)C$_6$H$_4$) | 3 | CH$_2$(2-(CH$_3$)C$_6$H$_4$) |
| 2 | CH$_2$(2-pyridyl) | 3 | CH$_2$(2-pyridyl) |
| 2 | CH$_2$(2-thienyl) | 3 | CH$_2$(2-thienyl) |
| 2 | CH$_2$-(2-furanyl) | 3 | CH$_2$-(2-furanyl) |
| 2 | CH$_2$(2-tetrahydrofuranyl) | 3 | CH$_2$(2-tetrahydrofuranyl) |
| 2 | CH$_2$(2-tetrahydropyranyl) | 3 | CH$_2$(2-tetrahydropyranyl) |
| 2 | Q-1 | 3 | Q-1 |
| 2 | Q-3 | 3 | Q-3 |
| 2 | Q-4 | 3 | Q-4 |
| 2 | Q-6 | 3 | Q-6 |
| 2 | Q-7 | 3 | Q-7 |
| 2 | Q-8 | 3 | Q-8 |
| 2 | Q-15 | 3 | Q-15 |

$R^1=CH_3, R^2=R^3=R^5=R^6=H$

| n | Q | n | Q |
|---|---|---|---|
| 2 | CH$_2$(2-(OCH$_3$)C$_6$H$_4$) | 3 | CH$_2$(2-(OCH$_3$)C$_6$H$_4$) |
| 2 | CH$_2$(2,4-F$_2$C$_6$H$_3$) | 3 | CH$_2$(2,4-F$_2$C$_6$H$_3$) |
| 2 | CH$_2$(2-(CN)C$_6$H$_4$) | 3 | CH$_2$(2-(CN)C$_6$H$_4$) |
| 2 | CH$_2$(2-(CF$_3$)C$_6$H$_4$) | 3 | CH$_2$(2-(CF$_3$)C$_6$H$_4$) |
| 2 | CH$_2$(2-(CH=CH$_2$)C$_6$H$_4$) | 3 | CH$_2$(2-(CH=CH$_2$)C$_6$H$_4$) |
| 4 | CH$_2$(C$_6$H$_5$) | 2 | CH$_2$(C$_6$H$_5$) |
| 4 | CH$_2$(2-FC$_6$H$_4$) | 2 | CH$_2$(2-FC$_6$H$_4$) |
| 4 | CH$_2$(2,6-F$_2$C$_6$H$_3$) | 2 | CH$_2$(2,6-F$_2$C$_6$H$_3$) |
| 4 | CH$_2$(2-ClC$_6$H$_4$) | 2 | CH$_2$(2-ClC$_6$H$_4$) |
| 4 | CH$_2$(2,6-Cl$_2$C$_6$H$_3$) | 2 | CH$_2$(2,6-Cl$_2$C$_6$H$_3$) |
| 4 | CH$_2$(2-Cl,6-FC$_6$H$_3$) | 2 | CH$_2$(2-Cl,6-FC$_6$H$_3$) |
| 4 | CH$_2$(2-BrC$_6$H$_4$) | 2 | CH$_2$(2-BrC$_6$H$_4$) |
| 4 | CH$_2$(2,6-Br$_2$C$_6$H$_3$) | 2 | CH$_2$(2,6-Br$_2$C$_6$H$_3$) |
| 4 | CH$_2$(2-(CH$_3$)C$_6$H$_4$) | 2 | CH$_2$(2-(CH$_3$)C$_6$H$_4$) |
| 4 | CH$_2$(2-pyridyl) | 2 | CH$_2$(2-pyridyl) |
| 4 | CH$_2$(2-thienyl) | 2 | CH$_2$(2-thienyl) |
| 4 | CH$_2$(2-furanyl) | 2 | CH$_2$(2-furanyl) |
| 4 | CH$_2$(2-tetrahydrofuranyl) | 2 | CH$_2$(2-tetrahydrofuranyl) |
| 4 | CH$_2$(2-tetrahydropyranyl) | 2 | CH$_2$(2-tetrahydropyranyl) |
| 4 | Q-1 | 2 | Q-1 |
| 4 | Q-3 | 2 | Q-3 |
| 4 | Q-4 | 2 | Q-4 |
| 4 | Q-6 | 2 | Q-6 |
| 4 | Q-7 | 2 | Q-7 |
| 4 | Q-8 | 2 | Q-8 |

| $R^1=CH_3, R^2=R^3=R^5=R^6=H$ | | $R^1=R^2=CH_3, R^3=R^5=R^6=H$ | |
|---|---|---|---|
| n | Q | n | Q |
| 4 | Q-15 | 2 | Q-15 |
| 4 | CH$_2$(2-(OCH$_3$)C$_6$H$_4$) | 2 | CH$_2$(2-(OCH$_3$)C$_6$H$_4$) |
| 4 | CH$_2$(2,4-F$_2$C$_6$H$_3$) | 2 | CH$_2$(2,4-F$_2$C$_6$H$_3$) |

TABLE 2-continued

| m | Q | m | Q |
|---|---|---|---|
| 4 | CH$_2$(2-(CN)C$_6$H$_4$) | 2 | CH$_2$(2-(CN)C$_6$H$_4$) |
| 4 | CH$_2$(2-(CF$_3$)C$_6$H$_4$) | 2 | CH$_2$(2-(CF$_3$)C$_6$H$_4$) |
| 4 | CH$_2$(2-CH=CH$_2$)C$_6$H$_4$ | 2 | CH$_2$(2-CH=CH$_2$)C$_6$H$_4$ |
| 3 | CH$_2$(C$_6$H$_5$) | 4 | CH$_2$(C$_6$H$_5$) |
| 3 | CH$_2$(2-FC$_6$H$_4$) | 4 | CH$_2$(2-FC$_6$H$_4$) |
| 3 | CH$_2$(2,6-F$_2$C$_6$H$_3$) | 4 | CH$_2$(2,6-F$_2$C$_6$H$_3$) |
| 3 | CH$_2$(2-ClC$_6$H$_4$) | 4 | CH$_2$(2-ClC$_6$H$_4$) |
| 3 | CH$_2$(2,6-Cl$_2$C$_6$H$_3$) | 4 | CH$_2$(2,6-Cl$_2$C$_6$H$_3$) |
| 3 | CH$_2$(2-Cl,6-FC$_6$H$_3$) | 4 | CH$_2$(2-Cl,6-FC$_6$H$_3$) |
| 3 | CH$_2$(2-BrC$_6$H$_4$) | 4 | CH$_2$(2-BrC$_6$H$_4$) |
| 3 | CH$_2$(2,6-Br$_2$C$_6$H$_3$) | 4 | CH$_2$(2,6-Br$_2$C$_6$H$_3$) |
| 3 | CH$_2$(2-(CH$_3$)C$_6$H$_4$) | 4 | CH$_2$(2-(CH$_3$)C$_6$H$_4$) |
| 3 | CH$_2$(2-pyridyl) | 4 | CH$_2$(2-pyridyl) |
| 3 | CH$_2$(2-thienyl) | 4 | CH$_2$(2-thienyl) |
| 3 | CH$_2$(2-furanyl) | 4 | CH$_2$(2-furanyl) |
| 3 | CH$_2$(2-tetrahydrofuranyl) | 4 | CH$_2$(2-tetrahydrofuranyl) |
| 3 | CH$_2$(2-tetrahydropyranyl) | 4 | CH$_2$(2-tetrahydropyranyl) |
| 3 | Q-1 | 4 | Q-1 |
| 3 | Q-3 | 4 | Q-3 |
| 3 | Q-4 | 4 | Q-4 |
| 3 | Q-6 | 4 | Q-6 |
| 3 | Q-7 | 4 | Q-7 |
| 3 | Q-8 | 4 | Q-8 |
| 3 | Q-15 | 4 | Q-15 |

$R^1$=CH$_3$, $R^2$=$R^3$=$R^5$=$R^6$=H

| m | Q | m | Q |
|---|---|---|---|
| 3 | CH$_2$(2-(OCH$_3$)C$_6$H$_4$) | 4 | CH$_2$(2-(OCH$_3$)C$_6$H$_4$) |
| 3 | CH$_2$(2,4-F$_2$C$_6$H$_3$) | 4 | CH$_2$(2,4-F$_2$C$_6$H$_3$) |
| 3 | CH$_2$(2-(CN)C$_6$H$_4$) | 4 | CH$_2$(2-(CN)C$_6$H$_4$) |
| 3 | CH$_2$(2-(CF$_3$)C$_6$H$_4$) | 4 | CH$_2$(2-(CF$_3$)C$_6$H$_4$) |
| 3 | CH$_2$(2-(CH=CH$_2$)C$_6$H$_4$) | 4 | CH$_2$(2-(CH=CH$_2$)C$_6$H$_4$) |

$R^1$=$R^3$=CH$_3$, $R^2$=$R^5$=$R^6$=H

| n | Q | n | Q |
|---|---|---|---|
| 2 | CH$_2$(C$_6$H$_5$) | 4 | CH$_2$(C$_6$H$_5$) |
| 2 | CH$_2$(2-FC$_6$H$_4$) | 4 | CH$_2$(2-FC$_6$H$_4$) |
| 2 | CH$_2$(2,6-F$_2$C$_6$H$_3$) | 4 | CH$_2$(2,6-F$_2$C$_6$H$_3$) |
| 2 | CH$_2$(2-ClC$_6$H$_4$) | 4 | CH$_2$(2-ClC$_6$H$_4$) |
| 2 | CH$_2$(2,6-Cl$_2$C$_6$H$_3$) | 4 | CH$_2$(2,6-Cl$_2$C$_6$H$_3$) |
| 2 | CH$_2$(2-Cl,6-FC$_6$H$_3$) | 4 | CH$_2$(2-Cl,6-FC$_6$H$_3$) |
| 2 | CH$_2$(2-BrC$_6$H$_4$) | 4 | CH$_2$(2-BrC$_6$H$_4$) |
| 2 | CH$_2$(2-(CH$_3$)C$_6$H$_4$) | 4 | CH$_2$(2-(CH$_3$)C$_6$H$_4$) |
| 2 | CH$_2$(2-tetrahydrofuranyl) | 4 | CH$_2$(2-tetrahydrofuranyl) |
| 2 | CH$_2$(2-tetrahydropyranyl) | 4 | CH$_2$(2-tetrahydropyranyl) |
| 2 | CH$_2$(2,4-F$_2$C$_6$H$_3$) | 4 | CH$_2$(2,4-F$_2$C$_6$H$_3$) |
| 2 | CH$_2$(2-(CH=CH$_2$)C$_6$H$_4$) | 4 | CH$_2$(2-(CH=CH$_2$)C$_6$H$_4$) |
| 2 | Q-1 | 4 | Q-1 |
| 3 | CH$_2$(C$_6$H$_5$) | 3 | CH$_2$(2-BrC$_6$H$_4$) |
| 3 | CH$_2$(2-FC$_6$H$_4$) | 3 | CH$_2$(2-(CH$_3$)C$_6$H$_4$) |
| 3 | CH$_2$(2,6-F$_2$C$_6$H$_3$) | 3 | CH$_2$(2-tetrahydrofuranyl) |
| 3 | CH$_2$(2-ClC$_6$H$_4$) | 3 | CH$_2$(2-tetrahydropyranyl) |
| 3 | CH$_2$(2,6-Cl$_2$C$_6$H$_3$) | 3 | CH$_2$(2,4-F$_2$C$_6$H$_3$) |
| 3 | CH$_2$(2-Cl,6-FC$_6$H$_3$) | 3 | CH$_2$(2-(CH=CH$_2$)C$_6$H$_4$) |

$R^1$=$R^5$=CH$_3$, $R^2$=$R^3$=$R^6$=H

| n | Q | n | Q |
|---|---|---|---|
| 2 | CH$_2$(C$_6$H$_5$) | 4 | CH$_2$(C$_6$H$_5$) |
| 2 | CH$_2$(2-FC$_6$H$_4$) | 4 | CH$_2$(2-FC$_6$H$_4$) |
| 2 | CH$_2$(2,6-F$_2$C$_6$H$_3$) | 4 | CH$_2$(2,6-F$_2$C$_6$H$_3$) |
| 2 | CH$_2$(2-ClC$_6$H$_4$) | 4 | CH$_2$(2-ClC$_6$H$_4$) |
| 2 | CH$_2$(2,6-Cl$_2$C$_6$H$_3$) | 4 | CH$_2$(2,6-Cl$_2$C$_6$H$_3$) |
| 2 | CH$_2$(2-Cl,6-FC$_6$H$_3$) | 4 | CH$_2$(2-Cl,6-FC$_6$H$_3$) |
| 2 | CH$_2$(2-BrC$_6$H$_4$) | 4 | CH$_2$(2-BrC$_6$H$_4$) |
| 2 | CH$_2$(2-(CH$_3$)C$_6$H$_4$) | 4 | CH$_2$(2-(CH$_3$)C$_6$H$_4$) |
| 2 | CH$_2$(2-tetrahydrofuranyl) | 4 | CH$_2$(2-tetrahydrofuranyl) |
| 2 | CH$_2$(2-tetrahydropyranyl) | 4 | CH$_2$(2-tetrahydropyranyl) |
| 2 | CH$_2$(2,4-F$_2$C$_6$H$_3$) | 4 | CH$_2$(2,4-F$_2$C$_6$H$_3$) |
| 2 | CH$_2$(2-(CH=CH$_2$)C$_6$H$_4$) | 4 | CH$_2$(2-(CH=CH$_2$)C$_6$H$_4$) |
| 2 | Q-1 | 4 | Q-1 |
| 3 | CH$_2$(C$_6$H$_5$) | 3 | CH$_2$(2-BrC$_6$H$_4$) |

TABLE 2-continued

| n | Q | n | Q |
|---|---|---|---|
| 3 | $CH_2(2-FC_6H_4)$ | 3 | $CH_2(2-(CH_3)C_6H_4)$ |
| 3 | $CH_2(2,6-F_2C_6H_3)$ | 3 | $CH_2(2-tetrahydrofuranyl)$ |
| 3 | $CH_2(2-ClC_6H_4)$ | 3 | $CH_2(2-tetrahydropyranyl)$ |
| 3 | $CH_2(2,6-Cl_2C_6H_3)$ | 3 | $CH_2(2,4-F_2C_6H_3)$ |
| 3 | $CH_2(2-Cl,6-FC_6H_3)$ | 3 | $CH_2(2-(CH=CH_2)C_6H_4)$ |

$R^5=R^1=CH_3, R^2=R^3=H, R^6=OCH_3$

| n | Q | n | Q |
|---|---|---|---|
| 2 | $CH_2(C_6H_5)$ | 4 | $CH_2(C_6H_5)$ |
| 2 | $CH_2(2-FC_6H_4)$ | 4 | $CH_2(2-FC_6H_4)$ |
| 2 | $CH_2(2,6-F_2C_6H_3)$ | 4 | $CH_2(2,6-F_2C_6H_3)$ |
| 2 | $CH_2(2-ClC_6H_4)$ | 4 | $CH_2(2-ClC_6H_4)$ |
| 2 | $CH_2(2,6-Cl_2C_6H_3)$ | 4 | $CH_2(2,6-Cl_2C_6H_3)$ |
| 2 | $CH_2(2-Cl,6-FC_6H_3)$ | 4 | $CH_2(2-Cl,6-FC_6H_3)$ |
| 2 | $CH_2(2-BrC_6H_4)$ | 4 | $CH_2(2-BrC_6H_4)$ |
| 2 | $CH_2(2-(CH_3)C_6H_4)$ | 4 | $CH_2(2-(CH_3)C_6H_4)$ |
| 2 | $CH_2(2-tetrahydrofuranyl)$ | 4 | $CH_2(2-tetrahydrofuranyl)$ |
| 2 | $CH_2(2-tetrahydropyranyl)$ | 4 | $CH_2(2-tetrahydropyranyl)$ |
| 2 | $CH_2(2,4-F_2C_6H_3)$ | 4 | $CH_2(2,4-F_2C_6H_3)$ |
| 2 | $CH_2(2-(CH=CH_2)C_6H_4)$ | 4 | $CH_2(2-(CH=CH_2)C_6H_4)$ |
| 2 | Q-1 | 4 | Q-1 |
| 3 | $CH_2(C_6H_5)$ | 3 | $CH_2(2-BrC_6H_4)$ |
| 3 | $CH_2(2-FC_6H_4)$ | 3 | $CH_2(2-(CH_3)C_6H_4)$ |
| 3 | $CH_2(2,6-F_2C_6H_3)$ | 3 | $CH_2(2-tetrahydrofuranyl)$ |
| 3 | $CH_2(2-ClC_6H_4)$ | 3 | $CH_2(2-tetrahydropyranyl)$ |
| 3 | $CH_2(2,6-Cl_2C_6H_3)$ | 3 | $CH_2(2,4-F_2C_6H_3)$ |
| 3 | $CH_2(2-Cl,6-FC_6H_3)$ | 3 | $CH_2(2-(CH=CH_2)C_6H_4)$ |

$R^1=CH_3, R^2=R^3=R^6=H, R^5=OCH_3$

| n | Q | n | Q |
|---|---|---|---|
| 2 | $CH_2(C_6H_5)$ | 4 | $CH_2(C_6H_5)$ |
| 2 | $CH_2(2-FC_6H_4)$ | 4 | $CH_2(2-FC_6H_4)$ |
| 2 | $CH_2(2,6-F_2C_6H_3)$ | 4 | $CH_2(2,6-F_2C_6H_3)$ |
| 2 | $CH_2(2-ClC_6H_4)$ | 4 | $CH_2(2-ClC_6H_4)$ |
| 2 | $CH_2(2,6-Cl_2C_6H_3)$ | 4 | $CH_2(2,6-Cl_2C_6H_3)$ |
| 2 | $CH_2(2-Cl,6-FC_6H_3)$ | 4 | $CH_2(2-Cl,6-FC_6H_3)$ |
| 2 | $CH_2(2-BrC_6H_4)$ | 4 | $CH_2(2-BrC_6H_4)$ |
| 2 | $CH_2(2-(CH_3)C_6H_4)$ | 4 | $CH_2(2-(CH_3)C_6H_4)$ |
| 2 | $CH_2(2-tetrahydrofuranyl)$ | 4 | $CH_2(2-tetrahydrofuranyl)$ |
| 2 | $CH_2(2-tetrahydropyranyl)$ | 4 | $CH_2(2-tetrahydropyranyl)$ |
| 2 | $CH_2(2,4-F_2C_6H_3)$ | 4 | $CH_2(2,4-F_2C_6H_3)$ |
| 2 | $CH_2(2-(CH=CH_2)C_6H_4)$ | 4 | $CH_2(2-(CH=CH_2)C_6H_4)$ |
| 2 | Q-1 | 4 | Q-1 |
| 3 | $CH_2(C_6H_5)$ | 3 | $CH_2(2-BrC_6H_4)$ |
| 3 | $CH_2(2-FC_6H_4)$ | 3 | $CH_2(2-(CH_3)C_6H_4)$ |
| 3 | $CH_2(2,6-F_2C_6H_3)$ | 3 | $CH_2(2-tetrahydrofuranyl)$ |
| 3 | $CH_2(2-ClC_6H_4)$ | 3 | $CH_2(2-tetrahydropyranyl)$ |
| 3 | $CH_2(2,6-Cl_2C_6H_3)$ | 3 | $CH_2(2,4-F_2C_6H_3)$ |
| 3 | $CH_2(2-Cl,6-FC_6H_3)$ | 3 | $CH_2(2-(CH=CH_2)C_6H_4)$ |

TABLE 3

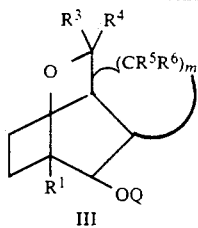

III

| m | Q | m | Q |
|---|---|---|---|
| | | $R^1=CH_3, R^3=R^4=R^5=R^6=H$ | |
| 1 | CH$_2$(C$_6$H$_5$) | 2 | CH$_2$(C$_6$H$_5$) |
| 1 | CH$_2$(2-FC$_6$H$_4$) | 2 | CH$_2$(2-FC$_6$H$_4$) |
| 1 | CH$_2$(2,6-F$_2$C$_6$H$_3$) | 2 | CH$_2$(2,6-F$_2$C$_6$H$_3$) |
| 1 | CH$_2$(2-ClC$_6$H$_4$) | 2 | CH$_2$(2-ClC$_6$H$_4$) |
| 1 | CH$_2$(2,6-Cl$_2$C$_6$H$_3$) | 2 | CH$_2$(2,6-Cl$_2$C$_6$H$_3$) |
| 1 | CH$_2$(2-Cl,6-FC$_6$H$_3$) | 2 | CH$_2$(2-Cl,6-FC$_6$H$_3$) |
| 1 | CH$_2$(2-BrC$_6$H$_4$) | 2 | CH$_2$(2-BrC$_6$H$_4$) |
| 1 | CH$_2$(2,6-Br$_2$C$_6$H$_3$) | 2 | CH$_2$(2,6-Br$_2$C$_6$H$_3$) |
| 1 | CH$_2$(2-(CH$_3$)C$_6$H$_4$) | 2 | CH$_2$(2-(CH$_3$)C$_6$H$_4$) |
| 1 | CH$_2$(2-pyridyl) | 2 | CH$_2$(2-pyridyl) |
| 1 | CH$_2$(2-thienyl) | 2 | CH$_2$(2-thienyl) |
| 1 | CH$_2$(2-furanyl) | 2 | CH$_2$(2-furanyl) |
| 1 | CH$_2$(2-tetrahydrofuranyl) | 2 | CH$_2$(2-tetrahydrofuranyl) |
| 1 | CH$_2$(2-tetrahydropyranyl) | 2 | CH$_2$(2-tetrahydropyranyl) |
| 1 | Q-1 | 2 | Q-1 |
| 1 | Q-3 | 2 | Q-3 |
| 1 | Q-4 | 2 | Q-4 |
| 1 | Q-6 | 2 | Q-6 |
| 1 | Q-7 | 2 | Q-7 |
| 1 | Q-8 | 2 | Q-8 |
| 1 | Q-15 | 2 | Q-15 |
| 1 | CH$_2$(2-(OCH$_3$)C$_6$H$_4$) | 1 | CH$_2$(2-(OCH$_3$)C$_6$H$_4$) |
| 1 | CH$_2$(2,4-F$_2$C$_6$H$_3$) | 1 | CH$_2$(2,4-F$_2$C$_6$H$_3$) |
| 1 | CH$_2$(2-(CN)C$_6$H$_4$) | 1 | CH$_2$(2-(CN)C$_6$H$_4$) |
| 1 | CH$_2$(2-(CF$_3$)C$_6$H$_4$) | 1 | CH$_2$(2-(CF$_3$)C$_6$H$_4$) |
| 1 | CH$_2$(2-(CH=CH$_2$)C$_6$H$_4$) | 1 | CH$_2$(2-(CH=CH$_2$)C$_6$H$_4$) |
| 3 | CH$_2$(C$_6$H$_5$) | 4 | CH$_2$(C$_6$H$_5$) |
| 3 | CH$_2$(2-FC$_6$H$_4$) | 4 | CH$_2$(2-FC$_6$H$_4$) |
| 3 | CH$_2$(2,6-F$_2$C$_6$H$_3$) | 4 | CH$_2$(2,6-F$_2$C$_6$H$_3$) |
| 3 | CH$_2$(2-ClC$_6$H$_4$) | 4 | CH$_2$(2-ClC$_6$H$_4$) |
| 3 | CH$_2$(2,6-Cl$_2$C$_6$H$_3$) | 4 | CH$_2$(2,6-Cl$_2$C$_6$H$_3$) |
| 3 | CH$_2$(2-Cl,6-FC$_6$H$_3$) | 4 | CH$_2$(2-Cl,6-FC$_6$H$_3$) |
| 3 | CH$_2$(2-BrC$_6$H$_4$) | 4 | CH$_2$(2-BrC$_6$H$_4$) |
| 3 | CH$_2$(2,6-Br$_2$C$_6$H$_3$) | 4 | CH$_2$(2,6-Br$_2$C$_6$H$_3$) |
| 3 | CH$_2$(2-(CH$_3$)C$_6$H$_4$) | 4 | CH$_2$(2-(CH$_3$)C$_6$H$_4$) |
| 3 | CH$_2$(2-pyridyl) | 4 | CH$_2$(2-pyridyl) |
| 3 | CH$_2$(2-thienyl) | 4 | CH$_2$(2-thienyl) |
| 3 | CH$_2$(2-furanyl) | 4 | CH$_2$(2-furanyl) |
| 3 | CH$_2$(2-tetrahydrofuranyl) | 4 | CH$_2$(2-tetrahydrofuranyl) |
| 3 | CH$_2$(2-tetrahydropyranyl) | 4 | CH$_2$(2-tetrahydropyranyl) |
| 3 | Q-1 | 4 | Q-1 |
| 3 | Q-3 | 4 | Q-3 |
| 3 | Q-4 | 4 | Q-4 |
| 3 | Q-6 | 4 | Q-6 |
| 3 | Q-7 | 4 | Q-7 |
| 3 | Q-8 | 4 | Q-8 |
| 3 | Q-15 | 4 | Q-15 |
| 3 | CH$_2$(2-(OCH$_3$)C$_6$H$_4$) | 4 | CH$_2$(2-(OCH$_3$)C$_6$H$_4$) |
| 3 | CH$_2$(2,4-F$_2$C$_6$H$_3$) | 4 | CH$_2$(2,4-F$_2$C$_6$H$_3$) |
| 3 | CH$_2$(2-(CN)C$_6$H$_4$) | 4 | CH$_2$(2-(CN)C$_6$H$_4$) |
| 3 | CH$_2$(2-(CF$_3$)C$_6$H$_4$) | 4 | CH$_2$(2-(CF$_3$)C$_6$H$_4$) |
| 3 | CH$_2$(2-(CH=CH$_2$)C$_6$H$_4$ | 4 | CH$_2$(2-(CH=CH$_2$)C$_6$H$_4$) |
| | | $R^1=CH_3=R^3=R^4, R^5=R^6=H$ | |
| 1 | CH$_2$(C$_6$H$_5$) | 2 | CH$_2$(C$_6$H$_5$) |
| 1 | CH$_2$(2-FC$_6$H$_4$) | 2 | CH$_2$(2-FC$_6$H$_4$) |
| 1 | CH$_2$(2,6-F$_2$C$_6$H$_3$) | 2 | CH$_2$(2,6-F$_2$C$_6$H$_3$) |
| 1 | CH$_2$(2-ClC$_6$H$_4$) | 2 | CH$_2$(2-ClC$_6$H$_4$) |
| 1 | CH$_2$(2,6-Cl$_2$C$_6$H$_3$) | 2 | CH$_2$(2,6-Cl$_2$C$_6$H$_3$) |
| 1 | CH$_2$(2-Cl,6-FC$_6$H$_3$) | 2 | CH$_2$(2-Cl,6-FC$_6$H$_3$) |
| 1 | CH$_2$(2-BrC$_6$H$_4$) | 2 | CH$_2$(2-BrC$_6$H$_4$) |
| 1 | CH$_2$(2,6-Br$_2$C$_6$H$_3$) | 2 | CH$_2$(2,6-Br$_2$C$_6$H$_3$) |
| 1 | CH$_2$(2-(CH$_3$)C$_6$H$_4$) | 2 | CH$_2$(2-(CH$_3$)C$_6$H$_4$) |
| 1 | CH$_2$(2-pyridyl) | 2 | CH$_2$(2-pyridyl) |
| 1 | CH$_2$(2-thienyl) | 2 | CH$_2$(2-thienyl) |

TABLE 3-continued

| | | | |
|---|---|---|---|
| 1 | CH$_2$(2-furanyl) | 2 | CH$_2$(2-furanyl) |
| 1 | CH$_2$(2-tetrahydrofuranyl) | 2 | CH$_2$(2-tetrahydrofuranyl) |
| 1 | CH$_2$(2-tetrahydropyranyl) | 2 | CH$_2$(2-tetrahydropyranyl) |
| 1 | Q-1 | 2 | Q-1 |
| 1 | Q-3 | 2 | Q-3 |
| 1 | Q-4 | 2 | Q-4 |
| 1 | Q-6 | 2 | Q-6 |
| 1 | Q-7 | 2 | Q-7 |
| 1 | Q-8 | 2 | Q-8 |
| 1 | Q-15 | 2 | Q-15 |
| 1 | CH$_2$(2-(OCH$_3$)C$_6$H$_4$) | 2 | CH$_2$(2-(OCH$_3$)C$_6$H$_4$) |
| 1 | CH$_2$(2,4-F$_2$C$_6$H$_3$) | 2 | CH$_2$(2,4-F$_2$C$_6$H$_3$) |
| 1 | CH$_2$(2-(CN)C$_6$H$_4$) | 2 | CH$_2$(2-(CN)C$_6$H$_4$) |
| 1 | CH$_2$(2-(CF$_3$)C$_6$H$_4$) | 2 | CH$_2$(2-(CF$_3$)C$_6$H$_4$) |
| 1 | CH$_2$(2-(CH=CH$_2$)C$_6$H$_4$) | 2 | CH$_2$(2-(CH=CH$_2$)C$_6$H$_4$) |
| 3 | CH$_2$(C$_6$H$_5$) | 4 | CH$_2$(C$_6$H$_5$) |
| 3 | CH$_2$(2-FC$_6$H$_4$) | 4 | CH$_2$(2-FC$_6$H$_4$) |
| 3 | CH$_2$(2,6-F$_2$C$_6$H$_3$) | 4 | CH$_2$(2,6-F$_2$C$_6$H$_3$) |
| 3 | CH$_2$(2-ClC$_6$H$_4$) | 4 | CH$_2$(2-ClC$_6$H$_4$) |
| 3 | CH$_2$(2-Cl,6-FC$_6$H$_3$) | 4 | CH$_2$(2-Cl,6-FC$_6$H$_3$) |
| 3 | CH$_2$(2-BrC$_6$H$_4$) | 4 | CH$_2$(2-BrC$_6$H$_4$) |
| 3 | CH$_2$(2,6-Br$_2$C$_6$H$_3$) | 4 | CH$_2$(2,6-Br$_2$C$_6$H$_3$) |
| 3 | CH$_2$(2-(CH$_3$)C$_6$H$_4$) | 4 | CH$_2$(2-(CH$_3$)C$_6$H$_4$) |
| 3 | CH$_2$(2-pyridyl) | 4 | CH$_2$(2-pyridyl) |
| 3 | CH$_2$(2-thienyl) | 4 | CH$_2$(2-thienyl) |
| 3 | CH$_2$(2-furanyl) | 4 | CH$_2$(2-furanyl) |
| 3 | CH$_2$(2-tetrahydrofuranyl) | 4 | CH$_2$(2-tetrahydrofuranyl) |
| 3 | CH$_2$(2-tetrahydropyranyl) | 4 | CH$_2$(2-tetrahydropyranyl) |
| 3 | Q-1 | 4 | Q-1 |
| 3 | Q-3 | 4 | Q-3 |
| 3 | Q-4 | 4 | Q-4 |
| 3 | Q-6 | 4 | Q-6 |
| 3 | Q-7 | 4 | Q-7 |
| 3 | Q-8 | 4 | Q-8 |
| 3 | Q-15 | 4 | Q-15 |
| 3 | CH$_2$(2-(OCH$_3$)C$_6$H$_4$) | 4 | CH$_2$(2-(OCH$_3$)C$_6$H$_4$) |
| 3 | CH$_2$(2,4-F$_2$C$_6$H$_3$) | 4 | CH$_2$(2,4-F$_2$C$_6$H$_3$) |
| 3 | CH$_2$(2-(CN)C$_6$H$_4$) | 4 | CH$_2$(2-(CN)C$_6$H$_4$) |
| 3 | CH$_2$(2-(CF$_3$)C$_6$H$_4$) | 4 | CH$_2$(2-(CF$_3$)C$_6$H$_4$) |
| 3 | CH$_2$(2-(CH=CH$_2$)C$_6$H$_4$) | 4 | CH$_2$(2-(CH=CH$_2$)C$_6$H$_4$) |

$R^1=CH_3, R^3=R^4=CH_2CH_3, R^5=R^6=H$

| | | | |
|---|---|---|---|
| 1 | CH$_2$(C$_6$H$_5$) | 2 | CH$_2$(C$_6$H$_5$) |
| 1 | CH$_2$(2-FC$_6$H$_4$) | 2 | CH$_2$(2-FC$_6$H$_4$) |
| 1 | CH$_2$(2,6-F$_2$C$_6$H$_3$) | 2 | CH$_2$(2,6-F$_2$C$_6$H$_3$) |
| 1 | CH$_2$(2-ClC$_6$H$_4$) | 2 | CH$_2$(2-ClC$_6$H$_4$) |
| 1 | CH$_2$(2,6-Cl$_2$C$_6$H$_3$) | 2 | CH$_2$(2,6-Cl$_2$C$_6$H$_3$) |
| 1 | CH$_2$(2-Cl,6-FC$_6$H$_3$) | 2 | CH$_2$(2-Cl,6-FC$_6$H$_3$) |
| 1 | CH$_2$(2-BrC$_6$H$_4$) | 2 | CH$_2$(2-BrC$_6$H$_4$) |
| 1 | CH$_2$(2,6-Br$_2$C$_6$H$_3$) | 2 | CH$_2$(2,6-Br$_2$C$_6$H$_3$) |
| 1 | CH$_2$(2-(CH$_3$)C$_6$H$_4$) | 2 | CH$_2$(2-(CH$_3$)C$_6$H$_4$) |
| 1 | CH$_2$(2-pyridyl) | 2 | CH$_2$(2-pyridyl) |
| 1 | CH$_2$(2-thienyl) | 2 | CH$_2$(2-thienyl) |
| 1 | CH$_2$(2-furanyl) | 2 | CH$_2$(2-furanyl) |
| 1 | CH$_2$(2-tetrahydrofuranyl) | 2 | CH$_2$(2-tetrahydrofuranyl) |
| 1 | CH$_2$(2-tetrahydropyranyl) | 2 | CH$_2$(2-tetrahydropyranyl) |
| 1 | Q-1 | 2 | Q-1 |
| 1 | Q-3 | 2 | Q-3 |
| 1 | Q-4 | 2 | Q-4 |
| 1 | Q-6 | 2 | Q-6 |
| 1 | Q-7 | 2 | Q-7 |
| 1 | Q-8 | 2 | Q-8 |
| 1 | Q-15 | 2 | Q-15 |
| 1 | CH$_2$(2-(OCH$_3$)C$_6$H$_4$) | 2 | CH$_2$(2-(OCH$_3$)C$_6$H$_4$) |
| 1 | CH$_2$(2,4-F$_2$C$_6$H$_3$) | 2 | CH$_2$(2,4-F$_2$C$_6$H$_3$) |
| 1 | CH$_2$(2-(CN)C$_6$H$_4$) | 2 | CH$_2$(2-(CN)C$_6$H$_4$) |
| 1 | CH$_2$(2-(CF$_3$)C$_6$H$_4$) | 2 | CH$_2$(2-(CF$_3$)C$_6$H$_4$) |
| 1 | CH$_2$(2-(CH=CH$_2$)C$_6$H$_4$) | 2 | CH$_2$(2-(CH=CH$_2$)C$_6$H$_4$) |
| 3 | CH$_2$(C$_6$H$_5$) | 4 | CH$_2$(C$_6$H$_5$) |
| 3 | CH$_2$(2-FC$_6$H$_4$) | 4 | CH$_2$(2-FC$_6$H$_4$) |
| 3 | CH$_2$(2,6-F$_2$C$_6$H$_3$) | 4 | CH$_2$(2,6-F$_2$C$_6$H$_3$) |
| 3 | CH$_2$(2-ClC$_6$H$_4$) | 4 | CH$_2$(2-ClC$_6$H$_4$) |
| 3 | CH$_2$(2,6-Cl$_2$C$_6$H$_3$) | 4 | CH$_2$(2,6-Cl$_2$C$_6$H$_3$) |
| 3 | CH$_2$(2-Cl,6-FC$_6$H$_3$) | 4 | CH$_2$(2-Cl,6-FC$_6$H$_3$) |
| 3 | CH$_2$(2-BrC$_6$H$_4$) | 4 | CH$_2$(2-BrC$_6$H$_4$) |
| 3 | CH$_2$(2,6-Br$_2$C$_6$H$_3$) | 4 | CH$_2$(2,6-Br$_2$C$_6$H$_3$) |
| 3 | CH$_2$(2-(CH$_3$)C$_6$H$_4$) | 4 | CH$_2$(2-(CH$_3$)C$_6$H$_4$) |
| 3 | CH$_2$(2-pyridyl) | 4 | CH$_2$(2-pyridyl) |
| 3 | CH$_2$(2-thienyl) | 4 | CH$_2$(2-thienyl) |

TABLE 3-continued

| | | | |
|---|---|---|---|
| 3 | CH$_2$(2-furanyl) | 4 | CH$_2$(2-furanyl) |
| 3 | CH$_2$(2-tetrahydrofuranyl) | 4 | CH$_2$(2-tetrahydrofuranyl) |
| 3 | CH$_2$(2-tetrahydropyranyl) | 4 | CH$_2$(2-tetrahydropyranyl) |
| 3 | Q-1 | 4 | Q-1 |
| 3 | Q-3 | 4 | Q-3 |
| 3 | Q-4 | 4 | Q-4 |
| 3 | Q-6 | 4 | Q-6 |
| 3 | Q-7 | 4 | Q-7 |
| 3 | Q-8 | 4 | Q-8 |
| 3 | Q-15 | 4 | Q-15 |
| 3 | CH$_2$(2-(OCH$_3$)C$_6$H$_4$) | 4 | CH$_2$(2-(OCH$_3$)C$_6$H$_4$) |
| 3 | CH$_2$(2,4-F$_2$C$_6$H$_3$) | 4 | CH$_2$(2,4-F$_2$C$_6$H$_3$) |
| 3 | CH$_2$(2-(CN)C$_6$H$_4$) | 4 | CH$_2$(2-(CN)C$_6$H$_4$) |
| 3 | CH$_2$(2-(CF$_3$(C$_6$H$_4$)) | 4 | CH$_2$(2-(CF$_3$(C$_6$H$_4$)) |
| 3 | CH$_2$(2-(CH=CH$_2$)C$_6$H$_4$ | 4 | CH$_2$(2-(CH=CH$_2$)C$_6$H$_4$ |

$R^1 = R^5 = CH_3, R^3 = R^4 = R^6 = H$

| | | | |
|---|---|---|---|
| 1 | CH$_2$(C$_6$H$_5$) | 3 | CH$_2$(C$_6$H$_5$) |
| 1 | CH$_2$(2-FC$_6$H$_4$) | 3 | CH$_2$(2-FC$_6$H$_4$) |
| 1 | CH$_2$(2,6-F$_2$C$_6$H$_3$) | 3 | CH$_2$(2,6-F$_2$C$_6$H$_3$) |
| 1 | CH$_2$(2-ClC$_6$H$_4$) | 3 | CH$_2$(2-ClC$_6$H$_4$) |
| 1 | CH$_2$(2,6-Cl$_2$C$_6$H$_3$) | 3 | CH$_2$(2,6-Cl$_2$C$_6$H$_3$) |
| 1 | CH$_2$(2-Cl,6-FC$_6$H$_3$) | 3 | CH$_2$(2-Cl,6-FC$_6$H$_3$) |
| 1 | CH$_2$(2-BrC$_6$H$_4$) | 3 | CH$_2$(2-BrC$_6$H$_4$) |
| 1 | CH$_2$(2-(CH$_3$)C$_6$H$_4$) | 3 | CH$_2$(2-(CH$_3$)C$_6$H$_4$) |
| 1 | CH$_2$(2-tetrahydrofuranyl) | 3 | CH$_2$(2-tetrahydrofuranyl) |
| 1 | CH$_2$(2-tetrahydropyranyl) | 3 | CH$_2$(2-tetrahydropyranyl) |
| 1 | CH$_2$(2,4-F$_2$C$_6$H$_3$) | 3 | CH$_2$(2,4-F$_2$C$_6$H$_3$) |
| 1 | CH$_2$(2-(CH=CH$_2$)C$_6$H$_4$) | 3 | CH$_2$(2-(CH=CH$_2$)C$_6$H$_4$) |
| 1 | Q-1 | 3 | Q-1 |
| 2 | CH$_2$(C$_6$H$_5$) | 4 | CH$_2$(C$_6$H$_5$) |
| 2 | CH$_2$(2-FC$_6$H$_4$) | 4 | CH$_2$(2-FC$_6$H$_4$) |
| 2 | CH$_2$(2,6-F$_2$C$_6$H$_3$) | 4 | CH$_2$(2,6-F$_2$C$_6$H$_3$) |
| 2 | CH$_2$(2-ClC$_6$H$_4$) | 4 | CH$_2$(2-ClC$_6$H$_4$) |
| 2 | CH$_2$(2,6-Cl$_2$C$_6$H$_3$) | 4 | CH$_2$(2,6-Cl$_2$C$_6$H$_3$) |
| 2 | CH$_2$(2-Cl,6-FC$_6$H$_3$) | 4 | CH$_2$(2-Cl,6-FC$_6$H$_3$) |
| 2 | CH$_2$(2-BrC$_6$H$_4$) | 4 | CH$_2$(2-BrC$_6$H$_4$) |
| 2 | CH$_2$(2-(CH$_3$)C$_6$H$_4$) | 4 | CH$_2$(2-(CH$_3$)C$_6$H$_4$) |
| 2 | CH$_2$(2-tetrahydrofuranyl) | 4 | CH$_2$(2-tetrahydrofuranyl) |
| 2 | CH$_2$(2-tetrahydropyranyl) | 4 | CH$_2$(2-tetrahydropyranyl) |
| 2 | CH$_2$(2,4-F$_2$C$_6$H$_3$) | 4 | CH$_2$(2,4-F$_2$C$_6$H$_3$) |
| 2 | CH$_2$(2-(CH=CH$_2$)C$_6$H$_4$) | 4 | CH$_2$(2-(CH=CH$_2$)C$_6$H$_4$) |

$R^1 = R^5 = CH_3, R^3 = R^4 = H, R^6 = OCH_3$

| | | | |
|---|---|---|---|
| 1 | CH$_2$(C$_6$H$_5$) | 3 | CH$_2$(C$_6$H$_5$) |
| 1 | CH$_2$(2-FC$_6$H$_4$) | 3 | CH$_2$(2-FC$_6$H$_4$) |
| 1 | CH$_2$(2,6-F$_2$C$_6$H$_3$) | 3 | CH$_2$(2,6-F$_2$C$_6$H$_3$) |
| 1 | CH$_2$(2-ClC$_6$H$_4$) | 3 | CH$_2$(2-ClC$_6$H$_4$) |
| 1 | CH$_2$(2,6-Cl$_2$C$_6$H$_3$) | 3 | CH$_2$(2,6-Cl$_2$C$_6$H$_3$) |
| 1 | CH$_2$(2-Cl,6-FC$_6$H$_3$) | 3 | CH$_2$(2-Cl,6-FC$_6$H$_3$) |
| 1 | CH$_2$(2-BrC$_6$H$_4$) | 3 | CH$_2$(2-BrC$_6$H$_4$) |
| 1 | CH$_2$(2-(CH$_3$)C$_6$H$_4$) | 3 | CH$_2$(2-(CH$_3$)C$_6$H$_4$) |
| 1 | CH$_2$(2-tetrahydrofuranyl) | 3 | CH$_2$(2-tetrahydrofuranyl) |
| 1 | CH$_2$(2-tetrahydropyranyl) | 3 | CH$_2$(2-tetrahydropyranyl) |
| 1 | CH$_2$(2,4-F$_2$C$_6$H$_3$) | 3 | CH$_2$(2,4-F$_2$C$_6$H$_3$) |
| 1 | CH$_2$(2-(CH=CH$_2$)C$_6$H$_4$) | 3 | CH$_2$(2-(CH=CH$_2$)C$_6$H$_4$) |
| 1 | Q-1 | 3 | Q-1 |
| 2 | CH$_2$(C$_6$H$_5$) | 4 | CH$_2$(C$_6$H$_5$) |
| 2 | CH$_2$(2-FC$_6$H$_4$) | 4 | CH$_2$(2-FC$_6$H$_4$) |
| 2 | CH$_2$(2,6-F$_2$C$_6$H$_3$) | 4 | CH$_2$(2,6-F$_2$C$_6$H$_3$) |
| 2 | CH$_2$(2-ClC$_6$H$_4$) | 4 | CH$_2$(2-ClC$_6$H$_4$) |
| 2 | CH$_2$(2,6-Cl$_2$C$_6$H$_3$) | 4 | CH$_2$(2,6-Cl$_2$C$_6$H$_3$) |
| 2 | CH$_2$(2-Cl,6-FC$_6$H$_3$) | 4 | CH$_2$(2-Cl,6-FC$_6$H$_3$) |
| 2 | CH$_2$(2-BrC$_6$H$_4$) | 4 | CH$_2$(2-BrC$_6$H$_4$) |
| 2 | CH$_2$(2-(CH$_3$)C$_6$H$_4$) | 4 | CH$_2$(2-(CH$_3$)C$_6$H$_4$) |
| 2 | CH$_2$(2-tetrahydrofuranyl) | 4 | CH$_2$(2-tetrahydrofuranyl) |
| 2 | CH$_2$(2-tetrahydropyranyl) | 4 | CH$_2$(2-tetrahydropyranyl) |
| 2 | CH$_2$(2,4-F$_2$C$_6$H$_3$) | 4 | CH$_2$(2,4-F$_2$C$_6$H$_3$) |
| 2 | CH$_2$(2-(CH=CH$_2$)C$_6$H$_4$) | 4 | CH$_2$(2-(CH=CH$_2$)C$_6$H$_4$) |

$R^1 = R^4 = CH_3, R^3 = R^5 = R^6 = H$

| | | | |
|---|---|---|---|
| 1 | CH$_2$(C$_6$H$_5$) | 3 | CH$_2$(C$_6$H$_5$) |
| 1 | CH$_2$(2-FC$_6$H$_4$) | 3 | CH$_2$(2-FC$_6$H$_4$) |

TABLE 3-continued

| | | | |
|---|---|---|---|
| 1 | $CH_2(2,6-F_2C_6H_3)$ | 3 | $CH_2(2,6-F_2C_6H_3)$ |
| 1 | $CH_2(2-ClC_6H_4)$ | 3 | $CH_2(2-ClC_6H_4)$ |
| 1 | $CH_2(2,6-Cl_2C_6H_3)$ | 3 | $CH_2(2,6-Cl_2C_6H_3)$ |
| 1 | $CH_2(2-Cl,6-FC_6H_3)$ | 3 | $CH_2(2-Cl,6-FC_6H_3)$ |
| 1 | $CH_2(2-BrC_6H_4)$ | 3 | $CH_2(2-BrC_6H_4)$ |
| 1 | $CH_2(2-(CH_3)C_6H_4)$ | 3 | $CH_2(2-(CH_3)C_6H_4)$ |
| 1 | $CH_2$(2-tetrahydrofuranyl) | 3 | $CH_2$(2-tetrahydrofuranyl) |
| 1 | $CH_2$(2-tetrahydropyranyl) | 3 | $CH_2$(2-tetrahydropyranyl) |
| 1 | $CH_2(2,4-F_2C_6H_3)$ | 3 | $CH_2(2,4-F_2C_6H_3)$ |
| 1 | $CH_2(2-(CH=CH_2)C_6H_4)$ | 3 | $CH_2(2-(CH=CH_2)C_6H_4)$ |
| 1 | Q-1 | 3 | Q-1 |
| 2 | $CH_2(C_6H_5)$ | 4 | $CH_2(C_6H_5)$ |
| 2 | $CH_2(2-FC_6H_4)$ | 4 | $CH_2(2-FC_6H_4)$ |
| 2 | $CH_2(2,6-F_2C_6H_3)$ | 4 | $CH_2(2,6-F_2C_6H_3)$ |
| 2 | $CH_2(2-ClC_6H_4)$ | 4 | $CH_2(2-ClC_6H_4)$ |
| 2 | $CH_2(2,6-Cl_2C_6H_3)$ | 4 | $CH_2(2,6-Cl_2C_6H_3)$ |
| 2 | $CH_2(2-Cl,6-FC_6H_3)$ | 4 | $CH_2(2-Cl,6-FC_6H_3)$ |
| 2 | $CH_2(2-BrC_6H_4)$ | 4 | $CH_2(2-BrC_6H_4)$ |
| 2 | $CH_2(2-(CH_3)C_6H_4)$ | 4 | $CH_2(2-(CH_3)C_6H_4)$ |
| 2 | $CH_2$(2-tetrahydrofuranyl) | 4 | $CH_2$(2-tetrahydrofuranyl) |
| 2 | $CH_2$(2-tetrahydropyranyl) | 4 | $CH_2$(2-tetrahydropyranyl) |
| 2 | $CH_2(2,4-F_2C_6H_3)$ | 4 | $CH_2(2,4-F_2C_6H_3)$ |
| 2 | $CH_2(2-(CH=CH_2)C_6H_4)$ | 4 | $CH_2(2-(CH=CH_2)C_6H_4)$ |

TABLE 4

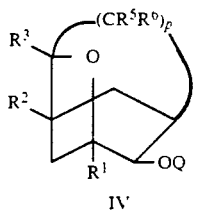

IV

| P | Q | P | Q |
|---|---|---|---|
| | $R^1=CH_3$, $R^2=R^3=R^5=R^6=H$ | | |
| 1 | $CH_2(C_6H_5)$ | 2 | $CH_2(C_6H_5)$ |
| 1 | $CH_2(2-FC_6H_4)$ | 2 | $CH_2(2-FC_6H_4)$ |
| 1 | $CH_2(2,6-F_2C_6H_3)$ | 2 | $CH_2(2,6-F_2C_6H_3)$ |
| 1 | $CH_2(2-ClC_6H_4)$ | 2 | $CH_2(2-ClC_6H_4)$ |
| 1 | $CH_2(2,6-Cl_2C_6H_3)$ | 2 | $CH_2(2,6-Cl_2C_6H_3)$ |
| 1 | $CH_2(2-Cl,6-FC_6H_3)$ | 2 | $CH_2(2-Cl,6-FC_6H_3)$ |
| 1 | $CH_2(2-BrC_6H_4)$ | 2 | $CH_2(2-BrC_6H_4)$ |
| 1 | $CH_2(2,6-BrC_6H_3)$ | 2 | $CH_2(2,6-BrC_6H_3)$ |
| 1 | $CH_2(2-(CH_3)C_6H_4)$ | 2 | $CH_2(2-(CH_3)C_6H_4)$ |
| 1 | $CH_2$(2-pyridyl) | 2 | $CH_2$(2-pyridyl) |
| 1 | $CH_2$(2-thienyl) | 2 | $CH_2$(2-thienyl) |
| 1 | $CH_2$(2-furanyl) | 2 | $CH_2$(2-furanyl) |
| 1 | $CH_2$(2-tetrahydrofuranyl) | 2 | $CH_2$(2-tetrahydrofuranyl) |
| 1 | $CH_2$(2-tetrahydropyranyl) | 2 | $CH_2$(2-tetrahydropyranyl) |
| 1 | Q-1 | 2 | Q-1 |
| 1 | Q-3 | 2 | Q-3 |
| 1 | Q-4 | 2 | Q-4 |
| 1 | Q-6 | 2 | Q-6 |
| 1 | Q-7 | 2 | Q-7 |
| 1 | Q-8 | 2 | Q-8 |
| 1 | Q-15 | 2 | Q-15 |
| 1 | $CH_2(2-(OCH_3)C_6H_4)$ | 2 | $CH_2(2-(OCH_3)C_6H_4)$ |
| 1 | $CH_2(2,4-F_2C_6H_3)$ | 2 | $CH_2(2,4-F_2C_6H_3)$ |
| 1 | $CH_2(2-(CN)C_6H_4)$ | 2 | $CH_2(2-(CN)C_6H_4)$ |
| 1 | $CH_2(2-(CF_3)C_6H_4)$ | 2 | $CH_2(2-(CF_3)C_6H_4)$ |
| 1 | $CH_2(2-(CH=CH_2)C_6H_4$ | 2 | $CH_2(2-(CH=CH_2)C_6H_4$ |
| | $R^1=CH_2CH_3$, $R^2=R^3=R^5=R^6=H$ | | |
| 1 | $CH_2(C_6H_5)$ | 2 | $CH_2(C_6H_5)$ |

TABLE 4-continued

| | | | | |
|---|---|---|---|---|
| 1 | $CH_2(2\text{-}FC_6H_4)$ | | 2 | $CH_2(2\text{-}FC_6H_4)$ |
| 1 | $CH_2(2,6\text{-}F_2C_6H_3)$ | | 2 | $CH_2(2,6\text{-}F_2C_6H_3)$ |
| 1 | $CH_2(2\text{-}ClC_6H_4)$ | | 2 | $CH_2(2\text{-}ClC_6H_4)$ |
| 1 | $CH_2(2,6\text{-}Cl_2C_6H_3)$ | | 2 | $CH_2(2,6\text{-}Cl_2C_6H_3)$ |
| 1 | $CH_2(2\text{-}Cl,6\text{-}FC_6H_3)$ | | 2 | $CH_2(2\text{-}Cl,6\text{-}FC_6H_3)$ |
| 1 | $CH_2(2\text{-}BrC_6H_4)$ | | 2 | $CH_2(2\text{-}BrC_6H_4)$ |
| 1 | $CH_2(2,6\text{-}BrC_6H_3)$ | | 2 | $CH_2(2,6\text{-}BrC_6H_3)$ |
| 1 | $CH_2(2\text{-}(CH_3)C_6H_4)$ | | 2 | $CH_2(2\text{-}(CH_3)C_6H_4)$ |
| 1 | $CH_2(2\text{-pyridyl})$ | | 2 | $CH_2(2\text{-pyridyl})$ |
| 1 | $CH_2(2\text{-thienyl})$ | | 2 | $CH_2(2\text{-thienyl})$ |
| 1 | $CH_2(2\text{-furanyl})$ | | 2 | $CH_2(2\text{-furanyl})$ |
| 1 | $CH_2(2\text{-tetrahydrofuranyl})$ | | 2 | $CH_2(2\text{-tetrahydrofuranyl})$ |
| 1 | $CH_2(2\text{-tetrahydropyranyl})$ | | 2 | $CH_2(2\text{-tetrahydropyranyl})$ |
| 1 | Q-1 | | 2 | Q-1 |
| 1 | Q-3 | | 2 | Q-3 |
| 1 | Q-4 | | 2 | Q-4 |
| 1 | Q-6 | | 2 | Q-6 |
| 1 | Q-7 | | 2 | Q-7 |
| 1 | Q-8 | | 2 | Q-8 |
| 1 | Q-15 | | 2 | Q-15 |
| 1 | $CH_2(2\text{-}(OCH_3)C_6H_4)$ | | 2 | $CH_2(2\text{-}(OCH_3)C_6H_4)$ |
| 1 | $CH_2(2,4\text{-}F_2C_6H_3)$ | | 2 | $CH_2(2,4\text{-}F_2C_6H_3)$ |
| 1 | $CH_2(2\text{-}(CN)C_6H_4)$ | | 2 | $CH_2(2\text{-}(CN)C_6H_4)$ |
| 1 | $CH_2(2\text{-}(CF_3)C_6H_4)$ | | 2 | $CH_2(2\text{-}(CF_3)C_6H_4)$ |
| 1 | $CH_2(2\text{-}(CH{=}CH_2)C_6H_4$ | | 2 | $CH_2(2\text{-}(CH{=}CH_2)C_6H_4$ |

| | $R^3 = R^5 = R^6 = H, R^1 = R^2 = CH_3$ | | | $R^1 = R^3 = CH_3, R^2 = R^5 = R^6 = H$ |
|---|---|---|---|---|
| 1 | $CH_2(C_6H_5)$ | | 1 | $CH_2(C_6H_5)$ |
| 1 | $CH_2(2\text{-}FC_6H_4)$ | | 1 | $CH_2(2\text{-}FC_6H_4)$ |
| 1 | $CH_2(2,6\text{-}F_2C_6H_3)$ | | 1 | $CH_2(2,6\text{-}F_2C_6H_3)$ |
| 1 | $CH_2(2\text{-}ClC_6H_4)$ | | 1 | $CH_2(2\text{-}ClC_6H_4)$ |
| 1 | $CH_2(2,6\text{-}Cl_2C_6H_3)$ | | 1 | $CH_2(2,6\text{-}Cl_2C_6H_3)$ |
| 1 | $CH_2(2\text{-}Cl,6\text{-}FC_6H_3)$ | | 1 | $CH_2(2\text{-}Cl,6\text{-}FC_6H_3)$ |
| 1 | $CH_2(2\text{-}BrC_6H_4)$ | | 1 | $CH_2(2\text{-}BrC_6H_4)$ |
| 1 | $CH_2(2\text{-}(CH_3)C_6H_4)$ | | 1 | $CH_2(2\text{-}(CH_3)C_6H_4)$ |
| 1 | $CH_2(2\text{-tetrahydrofuranyl})$ | | 1 | $CH_2(2\text{-tetrahydrofuranyl})$ |
| 1 | $CH_2(2\text{-tetrahydropyranyl})$ | | 1 | $CH_2(2\text{-tetrahydropyranyl})$ |
| 1 | $CH_2(2,4\text{-}F_2C_6H_3)$ | | 1 | $CH_2(2,4\text{-}F_2C_6H_3)$ |
| 1 | $CH_2(2\text{-}(CH{=}CH_2)C_6H_4)$ | | 1 | $CH_2(2\text{-}(CH{=}CH_2)C_6H_4)$ |
| 1 | Q-1 | | 1 | Q-1 |
| 2 | $CH_2(C_6H_5)$ | | 2 | $CH_2(C_6H_5)$ |
| 2 | $CH_2(2\text{-}FC_6H_4)$ | | 2 | $CH_2(2\text{-}FC_6H_4)$ |
| 2 | $CH_2(2,6\text{-}F_2C_6H_3)$ | | 2 | $CH_2(2,6\text{-}F_2C_6H_3)$ |
| 2 | $CH_2(2\text{-}ClC_6H_4)$ | | 2 | $CH_2(2\text{-}ClC_6H_4)$ |
| 2 | $CH_2(2,6\text{-}Cl_2C_6H_3)$ | | 2 | $CH_2(2,6\text{-}Cl_2C_6H_3)$ |
| 2 | $CH_2(2\text{-}Cl,6\text{-}FC_6H_3)$ | | 2 | $CH_2(2\text{-}Cl,6\text{-}FC_6H_3)$ |
| 2 | $CH_2(2\text{-}BrC_6H_4)$ | | 2 | $CH_2(2\text{-}BrC_6H_4)$ |
| 2 | $CH_2(2\text{-}(CH_3)C_6H_4)$ | | 2 | $CH_2(2\text{-}(CH_3)C_6H_4)$ |
| 2 | $CH_2(2\text{-tetrahydrofuranyl})$ | | 2 | $CH_2(2\text{-tetrahydrofuranyl})$ |
| 2 | $CH_2(2\text{-tetrahydropyranyl})$ | | 2 | $CH_2(2\text{-tetrahydropyranyl})$ |
| 2 | $CH_2(2,4\text{-}F_2C_6H_3)$ | | 2 | $CH_2(2,4\text{-}F_2C_6H_3)$ |
| 2 | $CH_2(2\text{-}(CH{=}CH_2)C_6H_4)$ | | 2 | $CH_2(2\text{-}(CH{=}CH_2)C_6H_4)$ |

| | $R^5 = R^1 = CH_3, R^2 = R^3 = R^6 = H$ | | | $R^1 = R^5 = CH_3, R^2 = R^3 = H, R^6 = OCH_3$ |
|---|---|---|---|---|
| 1 | $CH_2(C_6H_5)$ | | 1 | $CH_2(C_6H_5)$ |
| 1 | $CH_2(2\text{-}FC_6H_4)$ | | 1 | $CH_2(2\text{-}FC_6H_4)$ |
| 1 | $CH_2(2,6\text{-}F_2C_6H_3)$ | | 1 | $CH_2(2,6\text{-}F_2C_6H_3)$ |
| 1 | $CH_2(2\text{-}ClC_6H_4)$ | | 1 | $CH_2(2\text{-}ClC_6H_4)$ |
| 1 | $CH_2(2,6\text{-}Cl_2C_6H_3)$ | | 1 | $CH_2(2,6\text{-}Cl_2C_6H_3)$ |
| 1 | $CH_2(2\text{-}Cl,6\text{-}FC_6H_3)$ | | 1 | $CH_2(2\text{-}Cl,6\text{-}FC_6H_3)$ |
| 1 | $CH_2(2\text{-}BrC_6H_4)$ | | 1 | $CH_2(2\text{-}BrC_6H_4)$ |
| 1 | $CH_2(2\text{-}(CH_3)C_6H_4)$ | | 1 | $CH_2(2\text{-}(CH_3)C_6H_4)$ |
| 1 | $CH_2(2\text{-tetrahydrofuranyl})$ | | 1 | $CH_2(2\text{-tetrahydrofuranyl})$ |
| 1 | $CH_2(2\text{-tetrahydropyranyl})$ | | 1 | $CH_2(2\text{-tetrahydropyranyl})$ |
| 1 | $CH_2(2,4\text{-}F_2C_6H_3)$ | | 1 | $CH_2(2,4\text{-}F_2C_6H_3)$ |
| 1 | $CH_2(2\text{-}(CH{=}CH_2)C_6H_4)$ | | 1 | $CH_2(2\text{-}(CH{=}CH_2)C_6H_4)$ |
| 1 | Q-1 | | 1 | Q-1 |
| 2 | $CH_2(C_6H_5)$ | | 2 | $CH_2(C_6H_5)$ |
| 2 | $CH_2(2\text{-}FC_6H_4)$ | | 2 | $CH_2(2\text{-}FC_6H_4)$ |
| 2 | $CH_2(2,6\text{-}F_2C_6H_3)$ | | 2 | $CH_2(2,6\text{-}F_2C_6H_3)$ |
| 2 | $CH_2(2\text{-}ClC_6H_4)$ | | 2 | $CH_2(2\text{-}ClC_6H_4)$ |
| 2 | $CH_2(2,6\text{-}Cl_2C_6H_3)$ | | 2 | $CH_2(2,6\text{-}Cl_2C_6H_3)$ |
| 2 | $CH_2(2\text{-}Cl,6\text{-}FC_6H_3)$ | | 2 | $CH_2(2\text{-}Cl,6\text{-}FC_6H_3)$ |
| 2 | $CH_2(2\text{-}BrC_6H_4)$ | | 2 | $CH_2(2\text{-}BrC_6H_4)$ |
| 2 | $CH_2(2\text{-}(CH_3)C_6H_4)$ | | 2 | $CH_2(2\text{-}(CH_3)C_6H_4)$ |
| 2 | $CH_2(2\text{-tetrahydrofuranyl})$ | | 2 | $CH_2(2\text{-tetrahydrofuranyl})$ |

TABLE 4-continued

| | | | |
|---|---|---|---|
| 2 | CH$_2$(2-tetrahydropyranyl) | 2 | CH$_2$(2-tetrahydropyranyl) |
| 2 | CH$_2$(2,4-F$_2$C$_6$H$_3$) | 2 | CH$_2$(2,4-F$_2$C$_6$H$_3$) |
| 2 | CH$_2$(2-(CH=CH$_2$)C$_6$H$_4$) | 2 | CH$_2$(2-(CH=CH$_2$)C$_6$H$_4$) |

| | R$^1$=CH$_3$, R$^2$=R$^3$=R$^5$=H, R$^6$=OCH$_3$ | | R$^1$=CH$_3$, R$^2$=R$^3$=R$^5$=H, R$^6$=OCH$_3$ |
|---|---|---|---|
| 1 | CH$_2$(C$_6$H$_5$) | 2 | CH$_2$(C$_6$H$_5$) |
| 1 | CH$_2$(2-FC$_6$H$_4$) | 2 | CH$_2$(2-FC$_6$H$_4$) |
| 1 | CH$_2$(2,6-F$_2$C$_6$H$_3$) | 2 | CH$_2$(2,6-F$_2$C$_6$H$_3$) |
| 1 | CH$_2$(2-ClC$_6$H$_4$) | 2 | CH$_2$(2-ClC$_6$H$_4$) |
| 1 | CH$_2$(2,6-Cl$_2$C$_6$H$_3$) | 2 | CH$_2$(2,6-Cl$_2$C$_6$H$_3$) |
| 1 | CH$_2$(2-Cl,6-FC$_6$H$_3$) | 2 | CH$_2$(2-Cl,6-FC$_6$H$_3$) |
| 1 | CH$_2$(2-BrC$_6$H$_4$) | 2 | CH$_2$(2-BrC$_6$H$_4$) |
| 1 | CH$_2$(2-(CH$_3$)C$_6$H$_4$) | 2 | CH$_2$(2-(CH$_3$)C$_6$H$_4$) |
| 1 | CH$_2$(2-tetrahydrofuranyl) | 2 | CH$_2$(2-tetrahydrofuranyl) |
| 1 | CH$_2$(2-tetrahydropyranyl) | 2 | CH$_2$(2-tetrahydropyranyl) |
| 1 | CH$_2$(2,4-F$_2$C$_6$H$_3$) | 2 | CH$_2$(2,4-F$_2$C$_6$H$_3$) |
| 1 | CH$_2$(2-(CH=CH$_2$)C$_6$H$_4$) | 2 | CH$_2$(2-(CH=CH$_2$)C$_6$H$_4$) |

TABLE 5

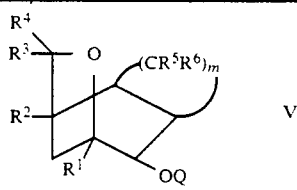

V

| m | Q | m | Q |
|---|---|---|---|
| | R$^1$ = CH$_3$, R$^3$ = R$^4$ = H, R$^5$ = R$^6$ = H | | R$^1$ = CH$_3$, R$^3$ = R$^4$ = H, R$^5$ = R$^6$ = H |
| 1 | CH$_2$(C$_6$H$_5$) | 2 | CH$_2$(CH$_6$H$_5$) |
| 1 | CH$_2$(2-FC$_6$H$_4$) | 2 | CH$_2$(2-FC$_6$H$_4$) |
| 1 | CH$_2$(2,6-F$_2$C$_6$H$_3$) | 2 | CH$_2$(2,6-F$_2$C$_6$H$_3$) |
| 1 | CH$_2$(2-ClC$_6$H$_4$) | 2 | CH$_2$(2-ClC$_6$H$_4$) |
| 1 | CH$_2$(2,6-Cl$_2$C$_6$H$_3$) | 2 | CH$_2$(2,6-Cl$_2$C$_6$H$_3$) |
| 1 | CH$_2$(2-Cl, 6-FC$_6$H$_3$) | 2 | CH$_2$(2-Cl, 6-FC$_6$H$_3$) |
| 1 | CH$_2$(2-BrC$_6$H$_4$) | 2 | CH$_2$(2-BrC$_6$H$_4$) |
| 1 | CH$_2$(2,6-Br$_2$C$_6$H$_3$) | 2 | CH$_2$(2,6-Br$_2$C$_6$H$_3$) |
| 1 | CH$_2$(2-(CH$_3$)C$_6$H$_4$) | 2 | CH$_2$(2-(CH$_3$)C$_6$H$_4$) |
| 1 | CH$_2$(2-pyridyl) | 2 | CH$_2$(2-pyridyl) |
| 1 | CH$_2$(2-thienyl) | 2 | CH$_2$(2-thienyl) |
| 1 | CH$_2$(2-furanyl) | 2 | CH$_2$(2-furanyl) |
| 1 | CH$_2$(2-tetrahydrofuranyl) | 2 | CH$_2$(2-tetrahydrofuranyl) |
| 1 | CH$_2$(2-tetrahydropyranyl) | 2 | CH$_2$(2-tetrahydropyranyl) |
| 1 | Q-1 | 2 | Q-1 |
| 1 | Q-3 | 2 | Q-3 |
| 1 | Q-4 | 2 | Q-4 |
| 1 | Q-6 | 2 | Q-6 |
| 1 | Q-7 | 2 | Q-7 |
| 1 | Q-8 | 2 | Q-8 |
| 1 | Q-15 | 2 | Q-15 |
| 1 | CH$_2$(2-(OCH$_3$)C$_6$H$_4$) | 2 | CH$_2$(2-(OCH$_3$)C$_6$H$_4$) |
| 1 | CH$_2$(2,4-F$_2$C$_6$H$_3$) | 2 | CH$_2$(2,4-F$_2$C$_6$H$_3$) |
| 1 | CH$_2$(2-(CN)C$_6$H$_4$) | 2 | CH$_2$(2-(CN)C$_6$H$_4$) |
| 1 | CH$_2$(2-(CF$_3$)C$_6$H$_4$) | 2 | CH$_2$(2-(CF$_3$)C$_6$H$_4$) |
| 1 | CH$_2$(2-(CH=CH$_2$)C$_6$H$_4$) | 2 | CH$_2$(2-(CH=CH$_2$)C$_6$H$_4$) |
| 3 | CH$_2$(C$_6$H$_5$) | 4 | CH$_2$(C$_6$H$_5$) |
| 3 | CH$_2$(2-FC$_6$H$_4$) | 4 | CH$_2$(2-FC$_6$H$_4$) |
| 3 | CH$_2$(2,6-F$_2$C$_6$H$_3$) | 4 | CH$_2$(2,6-F$_2$C$_6$H$_3$) |
| 3 | CH$_2$(2-ClC$_6$H$_4$) | 4 | CH$_2$(2-ClC$_6$H$_4$) |
| 3 | CH$_2$(2,6-Cl$_2$C$_6$H$_3$) | 4 | CH$_2$(2,6-Cl$_2$C$_6$H$_3$) |
| 3 | CH$_2$(2-Cl, 6-FC$_6$H$_3$) | 4 | CH$_2$(2-Cl, 6-FC$_6$H$_3$) |
| 3 | CH$_2$(2-BrC$_6$H$_4$) | 4 | CH$_2$(2-BrC$_6$H$_4$) |
| 3 | CH$_2$(2,6-Br$_2$C$_6$H$_3$) | 4 | CH$_2$(2,6-Br$_2$C$_6$H$_3$) |
| 3 | CH$_2$(2-(CH$_3$)C$_6$H$_4$) | 4 | CH$_2$(2-(CH$_3$)C$_6$H$_4$) |

TABLE 5-continued

| | | | |
|---|---|---|---|
| 3 | CH$_2$(2-pyridyl) | 4 | CH$_2$(2-pyridyl) |
| 3 | CH$_2$(2-thienyl) | 4 | CH$_2$(2-thienyl) |
| 3 | CH$_2$(2-furanyl) | 4 | CH$_2$(2-furanyl) |
| 3 | CH$_2$(2-tetrahydrofuranyl) | 4 | CH$_2$(2-tetrahydrofuranyl) |
| 3 | CH$_2$(2-tetrahydropyranyl) | 4 | CH$_2$(2-tetrahydropyranyl) |
| 3 | Q-1 | 4 | Q-1 |
| 3 | Q-3 | 4 | Q-3 |
| 3 | Q-4 | 4 | Q-4 |
| 3 | Q-6 | 4 | Q-6 |
| 3 | Q-7 | 4 | Q-7 |
| 3 | Q-8 | 4 | Q-8 |
| 3 | Q-15 | 4 | Q-15 |
| 3 | CH$_2$(2-(OCH$_3$)C$_6$H$_4$) | 4 | CH$_2$(2-(OCH$_3$)C$_6$H$_4$) |
| 3 | CH$_2$(2,4-F$_2$C$_6$H$_3$) | 4 | CH$_2$(2,4-F$_2$C$_6$H$_3$) |
| 3 | CH$_2$(2-(CN)C$_6$H$_4$) | 4 | CH$_2$(2-(CN)C$_6$H$_4$) |
| 3 | CH$_2$(2-(CF$_3$)C$_6$H$_4$) | 4 | CH$_2$(2-(CF$_3$)C$_6$H$_4$) |
| 3 | CH$_2$(2-(CH=CH$_2$)C$_6$H$_4$ | 4 | CH$_2$(2-(CH=CH$_2$)C$_6$H$_4$ |
| | $R^1$ = CH$_2$CH$_3$, $R^3$ = $R^4$ = $R^5$ = $R^6$ = H | | $R^1$ = CH$_2$CH$_3$, $R^3$ = $R^4$ = $R^5$ = $R^6$ = H |
| 1 | CH$_2$(C$_6$H$_5$) | 2 | CH$_2$(C$_6$H$_5$) |
| 1 | CH$_2$(2-FC$_6$H$_4$) | 2 | CH$_2$(2-FC$_6$H$_4$) |
| 1 | CH$_2$(2,6-F$_2$C$_6$H$_3$) | 2 | CH$_2$(2,6-F$_2$C$_6$H$_3$) |
| 1 | CH$_2$(2-ClC$_6$H$_4$) | 2 | CH$_2$(2-ClC$_6$H$_4$) |
| 1 | CH$_2$(2,6-Cl$_2$C$_6$H$_3$) | 2 | CH$_2$(2,6-Cl$_2$C$_6$H$_3$) |
| 1 | CH$_2$(2-Cl, 6-FC$_6$H$_3$) | 2 | CH$_2$(2-Cl, 6-FC$_6$H$_3$) |
| 1 | CH$_2$(2-BrC$_6$H$_4$) | 2 | CH$_2$(2-BrC$_6$H$_4$) |
| 1 | CH$_2$(2,6-Br$_2$C$_6$H$_3$) | 2 | CH$_2$(2,6-Br$_2$C$_6$H$_3$) |
| 1 | CH$_2$(2-(CH$_3$)C$_6$H$_4$) | 2 | CH$_2$(2-(CH$_3$)C$_6$H$_4$) |
| 1 | CH$_2$(2-pyridyl) | 2 | CH$_2$(2-pyridyl) |
| 1 | CH$_2$(2-thienyl) | 2 | CH$_2$(2-thienyl) |
| 1 | CH$_2$(2-furanyl) | 2 | CH$_2$(2-furanyl) |
| 1 | CH$_2$(2-tetrahydrofuranyl) | 2 | CH$_2$(2-tetrahydrofuranyl) |
| 1 | CH$_2$(2-tetrahydropyranyl) | 2 | CH$_2$(2-tetrahydropyranyl) |
| 1 | Q-1 | 2 | Q-1 |
| 1 | Q-3 | 2 | Q-3 |
| 1 | Q-4 | 2 | Q-4 |
| 1 | Q-6 | 2 | Q-6 |
| 1 | Q-7 | 2 | Q-7 |
| 1 | Q-8 | 2 | Q-8 |
| 1 | Q-15 | 2 | Q-15 |
| 1 | CH$_2$(2-(OCH$_3$)C$_6$H$_4$) | 2 | CH$_2$(2-(OCH$_3$)C$_6$H$_4$) |
| 1 | CH$_2$(2,4-F$_2$C$_6$H$_3$) | 2 | CH$_2$(2,4-F$_2$C$_6$H$_3$) |
| 1 | CH$_2$(2-(CN)C$_6$H$_4$) | 2 | CH$_2$(2-(CN)C$_6$H$_4$) |
| 1 | CH$_2$(2-(CF$_3$)C$_6$H$_4$) | 2 | CH$_2$(2-(CF$_3$)C$_6$H$_4$) |
| 1 | CH$_2$(2-(CH=CH$_2$)C$_6$H$_4$ | 2 | CH$_2$(2-(CH=CH$_2$)C$_6$H$_4$ |
| 3 | CH$_2$(C$_6$H$_5$) | 4 | CH$_2$(C$_6$H$_5$) |
| 3 | CH$_2$(2-FC$_6$H$_4$) | 4 | CH$_2$(2-FC$_6$H$_4$) |
| 3 | CH$_2$(2,6-F$_2$C$_6$H$_3$) | 4 | CH$_2$(2,6-F$_2$C$_6$H$_3$) |
| 3 | CH$_2$(2-ClC$_6$H$_4$) | 4 | CH$_2$(2-ClC$_6$H$_4$) |
| 3 | CH$_2$(2,6-Cl$_2$C$_6$H$_3$) | 4 | CH$_2$(2,6-Cl$_2$C$_6$H$_3$) |
| 3 | CH$_2$(2-Cl, 6-FC$_6$H$_3$) | 4 | CH$_2$(2-Cl, 6-FC$_6$H$_3$) |
| 3 | CH$_2$(2-BrC$_6$H$_4$) | 4 | CH$_2$(2-BrC$_6$H$_4$) |
| 3 | CH$_2$(2,6-Br$_2$C$_6$H$_3$) | 4 | CH$_2$(2,6-Br$_2$C$_6$H$_3$) |
| 3 | CH$_2$(2-(CH$_3$)C$_6$H$_4$) | 4 | CH$_2$(2-(CH$_3$)C$_6$H$_4$) |
| 3 | CH$_2$(2-pyridyl) | 4 | CH$_2$(2-pyridyl) |
| 3 | CH$_2$(2-thienyl) | 4 | CH$_2$(2-thienyl) |
| 3 | CH$_2$(2-furanyl) | 4 | CH$_2$(2-furanyl) |
| 3 | CH$_2$(2-tetrahydrofuranyl) | 4 | CH$_2$(2-tetrahydrofuranyl) |
| 3 | CH$_2$(2-tetrahydropyranyl) | 4 | CH$_2$(2-tetrahydropyranyl) |
| 3 | Q-1 | 4 | Q-1 |
| 3 | Q-3 | 4 | Q-3 |
| 3 | Q-4 | 4 | Q-4 |
| 3 | Q-6 | 4 | Q-6 |
| 3 | Q-7 | 4 | Q-7 |
| 3 | Q-8 | 4 | Q-8 |
| 3 | Q-15 | 4 | Q-15 |
| 3 | CH$_2$(2-(OCH$_3$)C$_6$H$_4$) | 4 | CH$_2$(2-(OCH$_3$)C$_6$H$_4$) |
| 3 | CH$_2$(2,4-F$_2$C$_6$H$_3$) | 4 | CH$_2$(2,4-F$_2$C$_6$H$_3$) |
| 3 | CH$_2$(2-(CN)C$_6$H$_4$) | 4 | CH$_2$(2-(CN)C$_6$H$_4$) |
| 3 | CH$_2$(2-(CF$_3$)C$_6$H$_4$) | 4 | CH$_2$(2-(CF$_3$)C$_6$H$_4$) |
| 3 | CH$_2$(2-(CH=CH$_2$)C$_6$H$_4$ | 4 | CH$_2$(2-(CH=CH$_2$)C$_6$H$_4$ |
| | $R^1$ = $R^5$ = $R^6$ = CH$_3$ $R^3$ = $R^4$ = H | | $R^1$ = $R^5$ = $R^6$ = CH$_3$ $R^3$ = $R^4$ = H |
| 1 | CH$_2$(C$_6$H$_5$) | 3 | CH$_2$(C$_6$H$_5$) |

TABLE 5-continued

| | | | |
|---|---|---|---|
| 1 | CH₂(2-FC₆H₄) | 3 | CH₂(2-FC₆H₄) |
| 1 | CH₂(2,6-F₂C₆H₃) | 3 | CH₂(2,6-F₂C₆H₃) |
| 1 | CH₂(2-ClC₆H₄) | 3 | CH₂(2-ClC₆H₄) |
| 1 | CH₂(2,6-Cl₂C₆H₃) | 3 | CH₂(2,6-Cl₂C₆H₃) |
| 1 | CH₂(2-Cl, 6-FC₆H₃) | 3 | CH₂(2-Cl, 6-FC₆H₃) |
| 1 | CH₂(2-BrC₆H₄) | 3 | CH₂(2-BrC₆H₄) |
| 1 | CH₂(2-(CH₃(C₆H₄) | 3 | CH₂(2-(CH₃(C₆H₄) |
| 1 | CH₂(2-tetrahydrofuranyl) | 3 | CH₂(2-tetrahydrofuranyl) |
| 1 | CH₂(2-tetrahydropyranyl) | 3 | CH₂(2-tetrahydropyranyl) |
| 1 | CH₂(2,4-F₂C₆H₃) | 3 | CH₂(2,4-F₂C₆H₃) |
| 1 | CH₂(2-(CH=CH₂(C₆H₄) | 3 | CH₂(2-(CH=CH₂(C₆H₄) |
| 1 | Q-1 | 3 | Q-1 |
| 2 | CH₂(C₆H₅) | 4 | CH₂(C₆H₅) |
| 2 | CH₂(2-FC₆H₄) | 4 | CH₂(2-FC₆H₄) |
| 2 | CH₂(2,6-F₂C₆H₃) | 4 | CH₂(2,6-F₂C₆H₃) |
| 2 | CH₂(2-ClC₆H₄) | 4 | CH₂(2-ClC₆H₄) |
| 2 | CH₂(2,6-Cl₂C₆H₃) | 4 | CH₂(2,6-Cl₂C₆H₃) |
| 2 | CH₂(2-Cl, 6-FC₆H₃) | 4 | CH₂(2-Cl, 6-FC₆H₃) |
| 2 | CH₂(2-BrC₆H₄) | 4 | CH₂(2-BrC₆H₄) |
| 2 | CH₂(2-(CH₃(C₆H₄) | 4 | CH₂(2-(CH₃(C₆H₄) |
| 2 | CH₂(2-tetrahydrofuranyl) | 4 | CH₂(2-tetrahydrofuranyl) |
| 2 | CH₂(2-tetrahydropyranyl) | 4 | CH₂(2-tetrahydropyranyl) |
| 2 | CH₂(2,4-F₂C₆H₃) | 4 | CH₂(2,4-F₂C₆H₃) |
| 2 | CH₂(2-(CH=CH₂(C₆H₄) | 4 | CH₂(2-(CH=CH₂(C₆H₄) |

| | $R^1 = R^2 = CH_3$, $R^3 = R^4 = R^5 = R^6 = H$ | | $R^1 = R^2 = CH_3$, $R^3 = R^4 = R^5 = R^6 = H$ |
|---|---|---|---|
| 1 | CH₂(C₆H₅) | 3 | CH₂(C₆H₅) |
| 1 | CH₂(2-FC₆H₄) | 3 | CH₂(2-FC₆H₄) |
| 1 | CH₂(2,6-F₂C₆H₃) | 3 | CH₂(2,6-F₂C₆H₃) |
| 1 | CH₂(2-ClC₆H₄) | 3 | CH₂(2-ClC₆H₄) |
| 1 | CH₂(2,6-Cl₂C₆H₃) | 3 | CH₂(2,6-Cl₂C₆H₃) |
| 1 | CH₂(2-Cl, 6-FC₆H₃) | 3 | CH₂(2-Cl, 6-FC₆H₃) |
| 1 | CH₂(2-BrC₆H₄) | 3 | CH₂(2-BrC₆H₄) |
| 1 | CH₂(2-(CH₃(C₆H₄) | 3 | CH₂(2-(CH₃(C₆H₄) |
| 1 | CH₂(2-tetrahydrofuranyl) | 3 | CH₂(2-tetrahydrofuranyl) |
| 1 | CH₂(2-tetrahydropyranyl) | 3 | CH₂(2-tetrahydropyranyl) |
| 1 | CH₂(2,4-F₂C₆H₃) | 3 | CH₂(2,4-F₂C₆H₃) |
| 1 | CH₂(2-(CH=CH₂(C₆H₄) | 3 | CH₂(2-(CH=CH₂(C₆H₄) |
| 1 | Q-1 | 3 | Q-1 |
| 2 | CH₂(C₆H₅) | 4 | CH₂(C₆H₅) |
| 2 | CH₂(2-FC₆H₄) | 4 | CH₂(2-FC₆H₄) |
| 2 | CH₂(2,6-F₂C₆H₃) | 4 | CH₂(2,6-F₂C₆H₃) |
| 2 | CH₂(2-ClC₆H₄) | 4 | CH₂(2-ClC₆H₄) |
| 2 | CH₂(2,6-Cl₂C₆H₃) | 4 | CH₂(2,6-Cl₂C₆H₃) |
| 2 | CH₂(2-Cl, 6-FC₆H₃) | 4 | CH₂(2-Cl, 6-FC₆H₃) |
| 2 | CH₂(2-BrC₆H₄) | 4 | CH₂(2-BrC₆H₄) |
| 2 | CH₂(2-(CH₃(C₆H₄) | 4 | CH₂(2-(CH₃(C₆H₄) |
| 2 | CH₂(2-tetrahydrofuranyl) | 4 | CH₂(2-tetrahydrofuranyl) |
| 2 | CH₂(2-tetrahydropyranyl) | 4 | CH₂(2-tetrahydropyranyl) |
| 2 | CH₂(2,4-F₂C₆H₃) | 4 | CH₂(2,4-F₂C₆H₃) |
| 2 | CH₂(2-(CH=CH₂(C₆H₄) | 4 | CH₂(2-(CH=CH₂(C₆H₄) |

| | $R^1 = R^5 = CH_3$, $R^3 = R^4 = R^6 = H$ | | $R^1 = R^5 = CH_3$, $R^3 = R^4 = R^6 = H$ |
|---|---|---|---|
| 1 | CH₂(C₆H₅) | 3 | CH₂(C₆H₅) |
| 1 | CH₂(2-FC₆H₄) | 3 | CH₂(2-FC₆H₄) |
| 1 | CH₂(2,6-F₂C₆H₃) | 3 | CH₂(2,6-F₂C₆H₃) |
| 1 | CH₂(2-ClC₆H₄) | 3 | CH₂(2-ClC₆H₄) |
| 1 | CH₂(2,6-Cl₂C₆H₃) | 3 | CH₂(2,6-Cl₂C₆H₃) |
| 1 | CH₂(2-Cl, 6-FC₆H₃) | 3 | CH₂(2-Cl, 6-FC₆H₃) |
| 1 | CH₂(2-BrC₆H₄) | 3 | CH₂(2-BrC₆H₄) |
| 1 | CH₂(2-(CH₃(C₆H₄) | 3 | CH₂(2-(CH₃(C₆H₄) |
| 1 | CH₂(2-tetrahydrofuranyl) | 3 | CH₂(2-tetrahydrofuranyl) |
| 1 | CH₂(2-tetrahydropyranyl) | 3 | CH₂(2-tetrahydropyranyl) |
| 1 | CH₂(2,4-F₂C₆H₃) | 3 | CH₂(2,4-F₂C₆H₃) |
| 1 | CH₂(2-(CH=CH₂(C₆H₄) | 3 | CH₂(2-(CH=CH₂(C₆H₄) |
| 1 | Q-1 | 3 | Q-1 |
| 2 | CH₂(C₆H₅) | 4 | CH₂(C₆H₅) |
| 2 | CH₂(2-FC₆H₄) | 4 | CH₂(2-FC₆H₄) |
| 2 | CH₂(2,6-F₂C₆H₃) | 4 | CH₂(2,6-F₂C₆H₃) |
| 2 | CH₂(2-ClC₆H₄) | 4 | CH₂(2-ClC₆H₄) |
| 2 | CH₂(2,6-Cl₂C₆H₃) | 4 | CH₂(2,6-Cl₂C₆H₃) |
| 2 | CH₂(2-Cl, 6-FC₆H₃) | 4 | CH₂(2-Cl, 6-FC₆H₃) |
| 2 | CH₂(2-BrC₆H₄) | 4 | CH₂(2-BrC₆H₄) |
| 2 | CH₂(2-(CH₃(C₆H₄) | 4 | CH₂(2-(CH₃(C₆H₄) |

TABLE 5-continued

| | | | | |
|---|---|---|---|---|
| 2 | CH$_2$(2-tetrhydrofuranyl) | | 4 | CH$_2$(2-tetrhydrofuranyl) |
| 2 | CH$_2$(2-tetrahydropyranyl) | | 4 | CH$_2$(2-tetrahydropyranyl) |
| 2 | CH$_2$(2,4-F$_2$C$_6$H$_3$) | | 4 | CH$_2$(2,4-F$_2$C$_6$H$_3$) |
| 2 | CH$_2$(2-(CH=CH$_2$(C$_6$H$_4$) | | 4 | CH$_2$(2-(CH=CH$_2$(C$_6$H$_4$) |
| | R$^1$ = CH$_3$, R$^2$ = OCH$_3$, R$^3$ = R$^4$ = R$^6$ = H | | | R$^1$ = CH$_3$, R$^5$ = OCH$_3$, R$^3$ = R$^4$ = R$^6$ = H |
| 1 | CH$_2$(C$_6$H$_5$) | | 3 | CH$_2$(C$_6$H$_5$) |
| 1 | CH$_2$(2-FC$_6$H$_4$) | | 3 | CH$_2$(2-FC$_6$H$_4$) |
| 1 | CH$_2$(2,6-F$_2$C$_6$H$_3$) | | 3 | CH$_2$(2,6-F$_2$C$_6$H$_3$) |
| 1 | CH$_2$(2-ClC$_6$H$_4$) | | 3 | CH$_2$(2-ClC$_6$H$_4$) |
| 1 | CH$_2$(2,6-Cl$_2$C$_6$H$_3$) | | 3 | CH$_2$(2,6-Cl$_2$C$_6$H$_3$) |
| 1 | CH$_2$(2-Cl, 6-FC$_6$H$_3$) | | 3 | CH$_2$(2-Cl, 6-FC$_6$H$_3$) |
| 1 | CH$_2$(2-BrC$_6$H$_4$) | | 3 | CH$_2$(2-BrC$_6$H$_4$) |
| 1 | CH$_2$(2-(CH$_3$(C$_6$H$_4$) | | 3 | CH$_2$(2-(CH$_3$(C$_6$H$_4$) |
| 1 | CH$_2$(2-tetrahydrofuranyl) | | 3 | CH$_2$(2-tetrahydrofuranyl) |
| 1 | CH$_2$(2-tetrahydropyranyl) | | 3 | CH$_2$(2-tetrahydropyranyl) |
| 1 | CH$_2$(2,4-F$_2$C$_6$H$_3$) | | 3 | CH$_2$(2,4-F$_2$C$_6$H$_3$) |
| 1 | CH$_2$(2-(CH=CH$_2$(C$_6$H$_4$) | | 3 | CH$_2$(2-(CH=CH$_2$(C$_6$H$_4$) |
| 1 | Q-1 | | 3 | Q-1 |
| 2 | CH$_2$(C$_6$H$_5$) | | 4 | CH$_2$(C$_6$H$_5$) |
| 2 | CH$_2$(2-FC$_6$H$_4$) | | 4 | CH$_2$(2-FC$_6$H$_4$) |
| 2 | CH$_2$(2,6-F$_2$C$_6$H$_3$) | | 4 | CH$_2$(2,6-F$_2$C$_6$H$_3$) |
| 2 | CH$_2$(2-ClC$_6$H$_4$) | | 4 | CH$_2$(2-ClC$_6$H$_4$) |
| 2 | CH$_2$(2,6-Cl$_2$C$_6$H$_3$) | | 4 | CH$_2$(2,6-Cl$_2$C$_6$H$_3$) |
| 2 | CH$_2$(2-Cl, 6-FC$_6$H$_3$) | | 4 | CH$_2$(2-Cl, 6-FC$_6$H$_3$) |
| 2 | CH$_2$(2-BrC$_6$H$_4$) | | 4 | CH$_2$(2-BrC$_6$H$_4$) |
| 2 | CH$_2$(2-(CH$_3$(C$_6$H$_4$) | | 4 | CH$_2$(2-(CH$_3$(C$_6$H$_4$) |
| 2 | CH$_2$(2-tetrhydrofuranyl) | | 4 | CH$_2$(2-tetrhydrofuranyl) |
| 2 | CH$_2$(2-tetrahydropyranyl) | | 4 | CH$_2$(2-tetrahydropyranyl) |
| 2 | CH$_2$(2,4-F$_2$C$_6$H$_3$) | | 4 | CH$_2$(2,4-F$_2$C$_6$H$_3$) |
| 2 | CH$_2$(2-(CH=CH$_2$(C$_6$H$_4$) | | 4 | CH$_2$(2-(CH=CH$_2$(C$_6$H$_4$) |
| | R$^1$ = R$^6$ = CH$_3$, R$^5$ = OCH$_3$, R$^3$ = R$^4$ = H | | | R$^1$ = R$^6$ = CH$_3$, R$^5$ = OCH$_3$, R$^3$ = R$^4$ = H |
| 1 | CH$_2$(C$_6$H$_5$) | | 3 | CH$_2$(C$_6$H$_5$) |
| 1 | CH$_2$(2-FC$_6$H$_4$) | | 3 | CH$_2$(2-FC$_6$H$_4$) |
| 1 | CH$_2$(2,6-F$_2$C$_6$H$_3$) | | 3 | CH$_2$(2,6-F$_2$C$_6$H$_3$) |
| 1 | CH$_2$(2-ClC$_6$H$_4$) | | 3 | CH$_2$(2-ClC$_6$H$_4$) |
| 1 | CH$_2$(2,6-Cl$_2$C$_6$H$_3$) | | 3 | CH$_2$(2,6-Cl$_2$C$_6$H$_3$) |
| 1 | CH$_2$(2-Cl, 6-FC$_6$H$_3$) | | 3 | CH$_2$(2-Cl, 6-FC$_6$H$_3$) |
| 1 | CH$_2$(2-BrC$_6$H$_4$) | | 3 | CH$_2$(2-BrC$_6$H$_4$) |
| 1 | CH$_2$(2-(CH$_3$(C$_6$H$_4$) | | 3 | CH$_2$(2-(CH$_3$(C$_6$H$_4$) |
| 1 | CH$_2$(2-tetrahydrofuranyl) | | 3 | CH$_2$(2-tetrahydrofuranyl) |
| 1 | CH$_2$(2-tetrahydropyranyl) | | 3 | CH$_2$(2-tetrahydropyranyl) |
| 1 | CH$_2$(2,4-F$_2$C$_6$H$_3$) | | 3 | CH$_2$(2,4-F$_2$C$_6$H$_3$) |
| 1 | CH$_2$(2-(CH=CH$_2$(C$_6$H$_4$) | | 3 | CH$_2$(2-(CH=CH$_2$(C$_6$H$_4$) |
| 1 | Q-1 | | 3 | Q-1 |
| 2 | CH$_2$(C$_6$H$_5$) | | 4 | CH$_2$(C$_6$H$_5$) |
| 2 | CH$_2$(2-FC$_6$H$_4$) | | 4 | CH$_2$(2-FC$_6$H$_4$) |
| 2 | CH$_2$(2,6-F$_2$C$_6$H$_3$) | | 4 | CH$_2$(2,6-F$_2$C$_6$H$_3$) |
| 2 | CH$_2$(2-ClC$_6$H$_4$) | | 4 | CH$_2$(2-ClC$_6$H$_4$) |
| 2 | CH$_2$(2,6-Cl$_2$C$_6$H$_3$) | | 4 | CH$_2$(2,6-Cl$_2$C$_6$H$_3$) |
| 2 | CH$_2$(2-Cl, 6-FC$_6$H$_3$) | | 4 | CH$_2$(2-Cl, 6-FC$_6$H$_3$) |
| 2 | CH$_2$(2-BrC$_6$H$_4$) | | 4 | CH$_2$(2-BrC$_6$H$_4$) |
| 2 | CH$_2$(2-(CH$_3$(C$_6$H$_4$) | | 4 | CH$_2$(2-(CH$_3$(C$_6$H$_4$) |
| 2 | CH$_2$(2-tetrahydrofuranyl) | | 4 | CH$_2$(2-tetrahydrofuranyl) |
| 2 | CH$_2$(2-tetrahydropyranyl) | | 4 | CH$_2$(2-tetrahydropyranyl) |
| 2 | CH$_2$(2,4-F$_2$C$_6$H$_3$) | | 4 | CH$_2$(2,4-F$_2$C$_6$H$_3$) |
| 2 | CH$_2$(2-(CH=CH$_2$(C$_6$H$_4$) | | 4 | CH$_2$(2-(CH=CH$_2$(C$_6$H$_4$) |
| | R$^1$ = R$^3$ = R$^4$ = CH$_3$, R$^5$ = R$^6$ = H | | | R$^1$ = R$^3$ = R$^4$ = CH$_3$, R$^5$ = R$^6$ = H |
| 1 | CH$_2$(C$_6$H$_5$) | | 3 | CH$_2$(C$_6$H$_5$) |
| 1 | CH$_2$(2-FC$_6$H$_4$) | | 3 | CH$_2$(2-FC$_6$H$_4$) |
| 1 | CH$_2$(2,6-F$_2$C$_6$H$_3$) | | 3 | CH$_2$(2,6-F$_2$C$_6$H$_3$) |
| 1 | CH$_2$(2-ClC$_6$H$_4$) | | 3 | CH$_2$(2-ClC$_6$H$_4$) |
| 1 | CH$_2$(2,6-Cl$_2$C$_6$H$_3$) | | 3 | CH$_2$(2,6-Cl$_2$C$_6$H$_3$) |
| 1 | CH$_2$(2-Cl, 6-FC$_6$H$_3$) | | 3 | CH$_2$(2-Cl, 6-FC$_6$H$_3$) |
| 1 | CH$_2$(2-BrC$_6$H$_4$) | | 3 | CH$_2$(2-BrC$_6$H$_4$) |
| 1 | CH$_2$(2-(CH$_3$(C$_6$H$_4$) | | 3 | CH$_2$(2-(CH$_3$(C$_6$H$_4$) |
| 1 | CH$_2$(2-tetrahydrofuranyl) | | 3 | CH$_2$(2-tetrahydrofuranyl) |
| 1 | CH$_2$(2-tetrahydropyranyl) | | 3 | CH$_2$(2-tetrahydropyranyl) |

TABLE 5-continued

| | | | |
|---|---|---|---|
| 1 | $CH_2(2,4-F_2C_6H_3)$ | 3 | $CH_2(2,4-F_2C_6H_3)$ |
| 1 | $CH_2(2-(CH=CH_2(C_6H_4))$ | 3 | $CH_2(2-(CH=CH_2(C_6H_4))$ |
| 1 | Q-1 | 3 | Q-1 |
| 2 | $CH_2(C_6H_5)$ | 4 | $CH_2(C_6H_5)$ |
| 2 | $CH_2(2-FC_6H_4)$ | 4 | $CH_2(2-FC_6H_4)$ |
| 2 | $CH_2(2,6-F_2C_6H_3)$ | 4 | $CH_2(2,6-F_2C_6H_3)$ |
| 2 | $CH_2(2-ClC_6H_4)$ | 4 | $CH_2(2-ClC_6H_4)$ |
| 2 | $CH_2(2,6-Cl_2C_6H_3)$ | 4 | $CH_2(2,6-Cl_2C_6H_3)$ |
| 2 | $CH_2(2-Cl, 6-FC_6H_3)$ | 4 | $CH_2(2-Cl, 6-FC_6H_3)$ |
| 2 | $CH_2(2-BrC_6H_4)$ | 4 | $CH_2(2-BrC_6H_4)$ |
| 2 | $CH_2(2-(CH_3(C_6H_4))$ | 4 | $CH_2(2-(CH_3(C_6H_4))$ |
| 2 | $CH_2(2$-tetrahydrofuranyl) | 4 | $CH_2(2$-tetrahydrofuranyl) |
| 2 | $CH_2(2$-tetrahydropyranyl) | 4 | $CH_2(2$-tetrahydropyranyl) |
| 2 | $CH_2(2,4-F_2C_6H_3)$ | 4 | $CH_2(2,4-F_2C_6H_3)$ |
| 2 | $CH_2(2-(CH=CH_2(C_6H_4))$ | 4 | $CH_2(2-(CH=CH_2(C_6H_4))$ |

TABLE 6

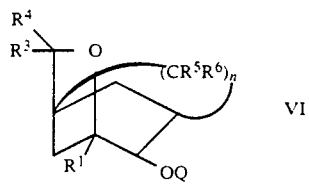

VI

| n | Q | n | Q |
|---|---|---|---|
| | $R^1 = CH_3$, $R^3 = R^4 = R^5 = R^6 = H$ | | $R^1 = CH_3$, $R^3 = R^4 = R^5 = R^6 = H$ |
| 2 | $CH_2(C_6H_5)$ | 3 | $CH_2(C_6H_5)$ |
| 2 | $CH_2(2-FC_6H_4)$ | 3 | $CH_2(2-FC_6H_4)$ |
| 2 | $CH_2(2,6-F_2C_6H_3)$ | 3 | $CH_2(2,6-F_2C_6H_3)$ |
| 2 | $CH_2(2-ClC_6H_4)$ | 3 | $CH_2(2-ClC_6H_4)$ |
| 2 | $CH_2(2,6-Cl_2C_6H_3)$ | 3 | $CH_2(2,6-Cl_2C_6H_3)$ |
| 2 | $CH_2(2-Cl, 6-FC_6H_3)$ | 3 | $CH_2(2-Cl, 6-FC_6H_3)$ |
| 2 | $CH_2(2-BrC_6H_4)$ | 3 | $CH_2(2-BrC_6H_4)$ |
| 2 | $CH_2(2,6-Br_2C_6H_3)$ | 3 | $CH_2(2,6-Br_2C_6H_3)$ |
| 2 | $CH_2(2-(CH_3)C_6H_4)$ | 3 | $CH_2(2-(CH_3)C_6H_4)$ |
| 2 | $CH_2(2$-pyridyl) | 3 | $CH_2(2$-pyridyl) |
| 2 | $CH_2(2$-thienyl) | 3 | $CH_2(2$-thienyl) |
| 2 | $CH_2(2$-furanyl) | 3 | $CH_2(2$-furanyl) |
| 2 | $CH_2(2$-tetrahydrofuranyl) | 3 | $CH_2(2$-tetrahydrofuranyl) |
| 2 | $CH_2(2$-tetrahydropyranyl) | 3 | $CH_2(2$-tetrahydropyranyl) |
| 2 | Q-1 | 3 | Q-1 |
| 2 | Q-3 | 3 | Q-3 |
| 2 | Q-4 | 3 | Q-4 |
| 2 | Q-6 | 3 | Q-6 |
| 2 | Q-7 | 3 | Q-7 |
| 2 | Q-8 | 3 | Q-8 |
| 2 | Q-15 | 3 | Q-15 |
| | $R^1 = CH_3$, $R^3 = R^4 = R^5 = R^6 = H$ | | $R^1 = CH_3$, $R^3 = R^4 = R^5 = R^6 = H$ |
| 2 | $CH_2(2-(OCH_3)C_6H_4)$ | 3 | $CH_2(2-(OCH_3)C_6H_4)$ |
| 2 | $CH_2(2,4-F_2C_6H_3)$ | 3 | $CH_2(2,4-F_2C_6H_3)$ |
| 2 | $CH_2(2-(CN)C_6H_4)$ | 3 | $CH_2(2-(CN)C_6H_4)$ |
| 2 | $CH_2(2-(CF_3)C_6H_4)$ | 3 | $CH_2(2-(CF_3)C_6H_4)$ |
| 2 | $CH_2(2-(CH=CH_2)C_6H_4$ | 3 | $CH_2(2-(CH=CH_2)C_6H_4$ |
| | $R^1 = CH_2CH_3$, $R^3 = R^4 = R^5 = R^6 = H$ | | $R^1 = CH_2CH_3$, $R^3 = R^4 = R^5 = R^6 = H$ |
| 4 | $CH_2(C_6H_5)$ | 2 | $CH_2(C_6H_5)$ |
| 4 | $CH_2(2-FC_6H_4)$ | 2 | $CH_2(2-FC_6H_4)$ |

TABLE 6-continued

| | | | |
|---|---|---|---|
| 4 | CH$_2$(2,6-F$_2$C$_6$H$_3$) | 2 | CH$_2$(2,6-F$_2$C$_6$H$_3$) |
| 4 | CH$_2$(2-ClC$_6$H$_4$) | 2 | CH$_2$(2-ClC$_6$H$_4$) |
| 4 | CH$_2$(2,6-Cl$_2$C$_6$H$_3$) | 2 | CH$_2$(2,6-Cl$_2$C$_6$H$_3$) |
| 4 | CH$_2$(2-Cl, 6-FC$_6$H$_3$) | 2 | CH$_2$(2-Cl, 6-FC$_6$H$_3$) |
| 4 | CH$_2$(2-BrC$_6$H$_4$) | 2 | CH$_2$(2-BrC$_6$H$_4$) |
| 4 | CH$_2$(2,6-Br$_2$C$_6$H$_3$) | 2 | CH$_2$(2,6-Br$_2$C$_6$H$_3$) |
| 4 | CH$_2$(2-(CH$_3$)C$_6$H$_4$) | 2 | CH$_2$(2-(CH$_3$)C$_6$H$_4$) |
| 4 | CH$_2$(2-pyridyl) | 2 | CH$_2$(2-pyridyl) |
| 4 | CH$_2$(2-thienyl) | 2 | CH$_2$(2-thienyl) |
| 4 | CH$_2$(2-furanyl) | 2 | CH$_2$(2-furanyl) |
| 4 | CH$_2$(2-tetrahydrofuranyl) | 2 | CH$_2$(2-tetrahydrofuranyl) |
| 4 | CH$_2$(2-tetrahydropyranyl) | 2 | CH$_2$(2-tetrahydropyranyl) |
| 4 | Q-1 | 2 | Q-1 |
| 4 | Q-3 | 2 | Q-3 |
| 4 | Q-4 | 2 | Q-4 |
| 4 | Q-6 | 2 | Q-6 |
| 4 | Q-7 | 2 | Q-7 |
| 4 | Q-8 | 2 | Q-8 |
| 4 | Q-15 | 2 | Q-15 |
| 4 | CH$_2$(2-(OCH$_3$)C$_6$H$_4$) | 2 | CH$_2$(2-(OCH$_3$)C$_6$H$_4$) |
| 4 | CH$_2$(2,4-F$_2$C$_6$H$_3$) | 2 | CH$_2$(2,4-F$_2$C$_6$H$_3$) |
| 4 | CH$_2$(2-(CN)C$_6$H$_4$) | 2 | CH$_2$(2-(CN)C$_6$H$_4$) |
| 4 | CH$_2$(2-(CF$_3$)C$_6$H$_4$) | 2 | CH$_2$(2-(CF$_3$)C$_6$H$_4$) |
| 4 | CH$_2$(2-(CH=CH$_2$)C$_6$H$_4$ | 2 | CH$_2$(2-(CH=CH$_2$)C$_6$H$_4$ |
| 3 | CH$_2$(C$_6$H$_5$) | 4 | CH$_2$(C$_6$H$_5$) |
| 3 | CH$_2$(2-FC$_6$H$_4$) | 4 | CH$_2$(2-FC$_6$H$_4$) |
| 3 | CH$_2$(2,6-F$_2$C$_6$H$_3$) | 4 | CH$_2$(2,6-F$_2$C$_6$H$_3$) |
| 3 | CH$_2$(2-ClC$_6$H$_4$) | 4 | CH$_2$(2-ClC$_6$H$_4$) |
| 3 | CH$_2$(2,6-Cl$_2$C$_6$H$_3$) | 4 | CH$_2$(2,6-Cl$_2$C$_6$H$_3$) |
| 3 | CH$_2$(2-Cl, 6-FC$_6$H$_3$) | 4 | CH$_2$(2-Cl, 6-FC$_6$H$_3$) |
| 3 | CH$_2$(2-BrC$_6$H$_4$) | 4 | CH$_2$(2-BrC$_6$H$_4$) |
| 3 | CH$_2$(2,6-Br$_2$C$_6$H$_3$) | 4 | CH$_2$(2,6-Br$_2$C$_6$H$_3$) |
| 3 | CH$_2$(2-(CH$_3$)C$_6$H$_4$) | 4 | CH$_2$(2-(CH$_3$)C$_6$H$_4$) |
| 3 | CH$_2$(2-pyridyl) | 4 | CH$_2$(2-pyridyl) |
| 3 | CH$_2$(2-thienyl) | 4 | CH$_2$(2-thienyl) |
| 3 | CH$_2$(2-furanyl) | 4 | CH$_2$(2-furanyl) |
| 3 | CH$_2$(2-tetrahydrofuranyl) | 4 | CH$_2$(2-tetrahydrofuranyl) |
| 3 | CH$_2$(2-tetrahydropyranyl) | 4 | CH$_2$(2-tetrahydropyranyl) |
| 3 | Q-1 | 4 | Q-1 |
| 3 | Q-3 | 4 | Q-3 |
| 3 | Q-4 | 4 | Q-4 |
| 3 | Q-6 | 4 | Q-6 |
| 3 | Q-7 | 4 | Q-7 |
| 3 | Q-8 | 4 | Q-8 |
| 3 | Q-15 | 4 | Q-15 |
| 3 | CH$_2$(2-(OCH$_3$)C$_6$H$_4$) | 4 | CH$_2$(2-(OCH$_3$)C$_6$H$_4$) |
| 3 | CH$_2$(2,4-F$_2$C$_6$H$_3$) | 4 | CH$_2$(2,4-F$_2$C$_6$H$_3$) |
| 3 | CH$_2$(2-(CN)C$_6$H$_4$) | 4 | CH$_2$(2-(CN)C$_6$H$_4$) |
| 3 | CH$_2$(2-(CF$_3$)C$_6$H$_4$) | 4 | CH$_2$(2-(CF$_3$)C$_6$H$_4$) |
| 3 | CH$_2$(2-(CH=CH$_2$)C$_6$H$_4$ | 4 | CH$_2$(2-(CH=CH$_2$)C$_6$H$_4$ |

| | $R^3 = R^4 = R^1 = CH_3$, $R^5 = R^6 = H$ | | $R^3 = R^4 = R^1 = CH_3$, $R^5 = R^6 = H$ |
|---|---|---|---|
| 2 | CH$_2$(C$_6$H$_5$) | 4 | CH$_2$(C$_6$H$_5$) |
| 2 | CH$_2$(2-FC$_6$H$_4$) | 4 | CH$_2$(2-FC$_6$H$_4$) |
| 2 | CH$_2$(2,6-F$_2$C$_6$H$_3$) | 4 | CH$_2$(2,6-F$_2$C$_6$H$_3$) |
| 2 | CH$_2$(2-ClC$_6$H$_4$) | 4 | CH$_2$(2-ClC$_6$H$_4$) |
| 2 | CH$_2$(2,6-Cl$_2$C$_6$H$_3$) | 4 | CH$_2$(2,6-Cl$_2$C$_6$H$_3$) |
| 2 | CH$_2$(2-Cl, 6-FC$_6$H$_3$) | 4 | CH$_2$(2-Cl, 6-FC$_6$H$_3$) |
| 2 | CH$_2$(2-BrC$_6$H$_4$) | 4 | CH$_2$(2-BrC6H$_4$) |
| 2 | CH$_2$(2-(CH$_3$)C$_6$H$_4$) | 4 | CH$_2$(2-(CH$_3$)C$_6$H$_4$) |
| 2 | CH$_2$(2-tetrahydrofuranyl | 4 | CH$_2$(2-tetrahydrofuranyl |
| 2 | CH$_2$(2-tetrahydropyranyl) | 4 | CH$_2$(2-tetrahydropyranyl) |
| 2 | CH$_2$(2,4-F$_2$C$_6$H$_3$) | 4 | CH$_2$(2,4-F$_2$C$_6$H$_3$) |
| 2 | CH$_2$(2-(CH=CH$_2$)C$_6$H$_4$) | 4 | CH$_2$(2-(CH=CH$_2$)C$_6$H$_4$) |
| 2 | Q-1 | 4 | Q-1 |
| 3 | CH$_2$(C$_6$H$_5$) | 3 | CH$_2$(2-BrC$_6$H$_4$) |
| 3 | CH$_2$(2-FC$_6$H$_4$) | 3 | CH$_2$(2-(CH$_3$)C$_6$H$_4$) |
| 3 | CH$_2$(2,6-F$_2$C$_6$H$_3$) | 3 | CH$_2$(2-tetrahydrofuranyl) |
| 3 | CH$_2$(2-ClC$_6$H$_4$) | 3 | CH$_2$(2-tetrahydropyranyl) |
| 3 | CH$_2$(2,6-Cl$_2$C$_6$H$_3$) | 3 | CH$_2$(2,6-F$_2$C$_6$H$_3$) |
| 3 | CH$_2$(2-Cl, 6-FC$_6$H$_3$) | 3 | CH$_2$(2-(CH=CH$_2$)C$_6$H$_4$) |

| | $R^1 = R^5 = CH_3$, $R^3 = R^4 = H$, $R^6 = H$ | | $R^1 = R^5 = CH_3$, $R^3 = R^4 = H$, $R^6 = OCH_3$ |
|---|---|---|---|
| 2 | CH$_2$(CH$_6$H$_5$) | 4 | CH$_2$(CH$_6$H$_5$) |

TABLE 6-continued

| | | | |
|---|---|---|---|
| 2 | CH$_2$(2-FC$_6$H$_4$) | 4 | CH$_2$(2-FC$_6$H$_4$) |
| 2 | CH$_2$(2,6-F$_2$C$_6$H$_3$) | 4 | CH$_2$(2,6-F$_2$C$_6$H$_3$) |
| 2 | CH$_2$(2-ClC$_6$H$_4$) | 4 | CH$_2$(2-ClC$_6$H$_4$) |
| 2 | CH$_2$(2,6-Cl$_2$C$_6$H$_3$) | 4 | CH$_2$(2,6-Cl$_2$C$_6$H$_3$) |
| 2 | CH$_2$(2-Cl, 6-FC$_6$H$_3$) | 4 | CH$_2$(2-Cl, 6-FC$_6$H$_3$) |
| 2 | CH$_2$(2-BrC6H$_4$) | 4 | CH$_2$(2-BrC6H$_4$) |
| 2 | CH$_2$(2-(CH$_3$)C$_6$H$_4$) | 4 | CH$_2$(2-(CH$_3$)C$_6$H$_4$) |
| 2 | CH$_2$(2-tetrahydrofuranyl | 4 | CH$_2$(2-tetrahydrofuranyl |
| 2 | CH$_2$(2-tetrahydropyranyl) | 4 | CH$_2$(2-tetrahydropyranyl) |
| 2 | CH$_2$(2,4-F$_2$C$_6$H$_3$) | 4 | CH$_2$(2,4-F$_2$C$_6$H$_3$) |
| 2 | CH$_2$(2-(CH=CH$_2$)C$_6$H$_4$) | 4 | CH$_2$(2-(CH=CH$_2$)C$_6$H$_4$) |
| 2 | Q-1 | 4 | Q-1 |
| 3 | CH$_2$(C$_6$H$_5$) | 3 | CH$_2$(2-BrC$_6$H$_4$) |
| 3 | CH$_2$(2-FC$_6$H$_4$) | 3 | CH$_2$(2-(CH$_3$)C$_6$H$_4$) |
| 3 | CH$_2$(2,6-F$_2$C$_6$H$_3$) | 3 | CH$_2$(2-tetrahydrofuranyl |
| 3 | CH$_2$(2-ClC$_6$H$_4$) | 3 | CH$_2$(2-tetrahydropyranyl) |
| 3 | CH$_2$(2,6-Cl$_2$C$_6$H$_3$) | 3 | CH$_2$(2,4-F$_2$C$_6$H$_3$) |
| 3 | CH$_2$(2-Cl, 6-FC$_6$H$_3$) | 3 | CH$_2$(2-(CH=CH$_2$)C$_6$H$_4$) |

| | | | |
|---|---|---|---|
| | R$^1$ = CH$_3$, | | R$^1$ = CH$_3$, |
| | R$^3$ = R$^4$ = R$^5$ = H, | | R$^3$ = R$^4$ = R$^5$ = H, |
| | R$^6$ = OCH$_3$ | | R$^6$ = OCH$_3$ |
| 2 | CH$_2$(C$_6$H$_5$) | 4 | CH$_2$(C$_6$H$_5$) |
| 2 | CH$_2$(2-FC$_6$H$_4$) | 4 | CH$_2$(2-FC$_6$H$_4$) |
| 2 | CH$_2$(2,6-F$_2$C$_6$H$_3$) | 4 | CH$_2$(2,6-F$_2$C$_6$H$_3$) |
| 2 | CH$_2$(2-ClC$_6$H$_4$) | 4 | CH$_2$(2-ClC$_6$H$_4$) |
| 2 | CH$_2$(2,6-Cl$_2$C$_6$H$_3$) | 4 | CH$_2$(2,6-Cl$_2$C$_6$H$_3$) |
| 2 | CH$_2$(2-Cl, 6-FC$_6$H$_3$) | 4 | CH$_2$(2-Cl, 6-FC$_6$H$_3$) |
| 2 | CH$_2$(2-BrC6H$_4$) | 4 | CH$_2$(2-BrC6H$_4$) |
| 2 | CH$_2$(2-(CH$_3$)C$_6$H$_4$) | 4 | CH$_2$(2-(CH$_3$)C$_6$H$_4$) |
| 2 | CH$_2$(2-tetrahydrofuranyl | 4 | CH$_2$(2-tetrahydrofuranyl |
| 2 | CH$_2$(2-tetrahydropyranyl) | 4 | CH$_2$(2-tetrahydropyranyl) |
| 2 | CH$_2$(2,4-F$_2$C$_6$H$_3$) | 4 | CH$_2$(2,4-F$_2$C$_6$H$_3$) |
| 2 | CH$_2$(2-(CH=CH$_2$)C$_6$H$_4$) | 4 | CH$_2$(2-(CH=CH$_2$)C$_6$H$_4$) |
| 2 | Q-1 | n | Q-1 |
| 3 | CH$_2$(C$_6$H$_5$) | 3 | CH$_2$(BrC$_6$H$_4$) |
| 3 | CH$_2$(2-FC$_6$H$_4$) | 3 | CH$_2$(2-(CH$_3$)C$_6$H$_4$) |
| 3 | CH$_2$(2,6-F$_2$C$_6$H$_3$) | 3 | CH$_2$(2-tetrahydrofuranyl) |
| 3 | CH$_2$(2-ClC$_6$H$_4$) | 3 | CH$_2$(2-tetrahydropropanol) |
| 3 | CH$_2$(2,6-Cl$_2$C$_6$H$_3$) | 3 | CH$_2$(2,4-F$_2$C$_6$H$_3$) |
| 3 | CH$_2$(2-Cl, 6-FC$_6$H$_3$) | 3 | CH$_2$(2-(CH=CH$_2$)C$_6$H$_4$) |

| | | | |
|---|---|---|---|
| | R$^4$ = R$^1$ = CH$_3$, | | R$^4$ = R$^1$ = CH$_3$, |
| | R$^3$ = R$^5$ = R$^6$ = H | | R$^3$ = R$^5$ = R$^6$ = H |
| 2 | CH$_2$(C$_6$H$_5$) | 4 | CH$_2$(C$_6$H$_5$) |
| 2 | CH$_2$(2-FC$_6$H$_4$) | 4 | CH$_2$(2-FC$_6$H$_4$) |
| 2 | CH$_2$(2,6-F$_2$C$_6$H$_3$) | 4 | CH$_2$(2,6-F$_2$C$_6$H$_3$) |
| 2 | CH$_2$(2-ClC$_6$H$_4$) | 4 | CH$_2$(2-ClC$_6$H$_4$) |
| 2 | CH$_2$(2,6-Cl$_2$C$_6$H$_3$) | 4 | CH$_2$(2,6-Cl$_2$C$_6$H$_3$) |
| 2 | CH$_2$(2-Cl, 6-FC$_6$H$_3$) | 4 | CH$_2$(2-Cl, 6-FC$_6$H$_3$) |
| 2 | CH$_2$(2-BrC6H$_4$) | 4 | CH$_2$(2-BrC6H$_4$) |
| 2 | CH$_2$(2-(CH$_3$)C$_6$H$_4$) | 4 | CH$_2$(2-(CH$_3$)C$_6$H$_4$) |
| 2 | CH$_2$(2-tetrahydrofuranyl | 4 | CH$_2$(2-tetrahydrofuranyl |
| 2 | CH$_2$(2-tetrahydropyranyl) | 4 | CH$_2$(2-tetrahydropyranyl) |
| 2 | CH$_2$(2,4-F$_2$C$_6$H$_3$) | 4 | CH$_2$(2,4-F$_2$C$_6$H$_3$) |
| 2 | CH$_2$(2-(CH=CH$_2$)C$_6$H$_4$) | 4 | CH$_2$(2-(CH=CH$_2$)C$_6$H$_4$) |
| 2 | Q-1 | 4 | Q-1 |
| 3 | CH$_2$(C$_6$H$_5$) | 3 | CH$_2$(2-BrC$_6$H$_4$) |
| 3 | CH$_2$(2-FC$_6$H$_4$) | 3 | CH$_2$(2-(CH$_3$)C$_6$H$_4$) |
| 3 | CH$_2$(2,6-F$_2$C$_6$H$_3$) | 3 | CH$_2$(2-tetrahydrofuranyl |
| 3 | CH$_2$(2-ClC$_6$H$_4$) | 3 | CH$_2$(2-tetrahydropyranyl) |
| 3 | CH$_2$(2,6-Cl$_2$C$_6$H$_3$) | 3 | CH$_2$(2,4-F$_2$C$_6$H$_3$) |
| 3 | CH$_2$(2-Cl, 6-FC$_6$H$_3$) | 3 | CH$_2$(2-(CH=CH$_2$)C$_6$H$_4$) |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

|  | Weight Percent* | | |
|---|---|---|---|
|  | Active Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredients plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carries or by agglomeration techniques. See J. E. Browning, "Agglomeration", *Chemical Engineering*, Dec. 4, 1967, pp. 147ff and "Perry's Chemical Engineer's Handbook", 5th Ed., McGraw-Hill, New York, 1973, pp. 8-59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52 53, 58, 132, 138-140, 162-164, 166, 167 and 169-182;

H. Gysin and E. Knusli, U.S. Pat. No. 2,891,855, Jun. 23, 1959, Col. 3, line 66 through Col. 5, line 17 and Examples 1-4;

G. G. Klingman, "Weed Control as a Science", John Wiley & Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE A

| | |
|---|---|
| $(1\alpha,2\alpha,4\alpha,5\beta,6\alpha)$-(+/−)-5-[(2-chloro-6-fluorophenyl)methoxy]-6-methyl-7-oxatricyclo-$[4.2.1.0^{2,4}]$nonane | 60% |
| sodium alkylnaphthalenesulfonate | 2% |
| sodium ligninsulfonate | 2% |
| synthetic amorphous silica | 36% |

The active ingredient is first sprayed onto the amorphous silica, then the ingredients are blended, hammer-milled until all the solids are essentially under 50 microns, reblended, and packaged.

EXAMPLE B

Wettable Powder

| | |
|---|---|
| $(1\alpha,2\alpha,4\alpha,5\beta,6\alpha)$-(+/−)-5-[(2-chloro-6-fluorophenyl)methoxy]-6-methyl-7-oxatricyclo-$[4.2.1.0^{2,4}]$nonane | 50% |
| sodium alkylnaphthalenesulfonate | 2% |
| low viscosity methyl cellulose | 2% |
| diatomaceous earth | 46% |

The active ingredient is first sprayed onto the diatomaceous earth, then the ingredients are blended, coarsely hammer-milled and then air-milled to produce particles essentially all below 10 microns in diameter. The product is reblended before packaging.

EXAMPLE C

Granule

| | |
|---|---|
| Wettable Powder of Example B | 5% |
| attapulgite granules | 95% |

A slurry of wettable powder containing 25% solids is sprayed on the surface of attapulgite granules in a double-cone blender. The granules are dried and packaged.

EXAMPLE D

Emulsifiable Concentrate

| | |
|---|---|
| (1α,2α,4α,5β,6α)-(+/−)-5-[(2-chloro-6-fluorophenyl)methoxy]-6-methyl-7-oxatricyclo-[4.2.1.0$^{2,4}$]nonane | 40% |
| Atlox 3404F | 3% |
| Atlox 3404F | 3% |
| xylene | 54% |

The active ingredient and Atlox emulsifiers are dissolved in the solvent, filtered and packaged. Atlox 3403F and 3404F are blends of anionic and ionic emulsifiers from ICI Americas, Inc.

EXAMPLE E

Low Strength Granule

| | |
|---|---|
| (1α,2α,4α,5β,6α)-(−/−)-5-[(2-chloro-6-fluorophenyl)methoxy]-6-methyl-7-oxatricyclo-[4.2.1.0$^{2,4}$]nonane | 5% |
| attapulgite granules (U.S.S. 20–40 mesh) | 95% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE F

Low Strength Granule

| | |
|---|---|
| (1α,2α,4α,5β,6α)-(+/−)-5-[(2-chloro-6-fluorophenyl)methoxy]-6-methyl-7-oxatricyclo-[4.2.1.0$^{2,4}$]nonane | 50% |
| wetting agent | 1% |
| crude ligninsulfonate salt (containing 5–20% of the natural sugars) | 10% |
| attapulgite clay | 39% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE G

Concentrated Emulsion

| | |
|---|---|
| (1α,2α,4α,5β,6α)-(+/−)-5-[(2-chloro-6-fluorophenyl)methoxy]-6-methyl-7-oxatricyclo-[4.2.1.0$^{2,4}$]nonane | 25% |
| xylene | 25% |
| Atlox 3404F | 5% |
| G1284 | 5% |
| ethylene glycol | 8% |
| water | 32% |

The active ingredient, solvent and emulsifiers are blended together. This solution is added to a mixture of the ethylene glycol and water with stirring.

EXAMPLE H

Solution

| | |
|---|---|
| (1α,2α,4α,5β,6α)-(+/−)-5-[(2-chloro-6-fluorophenyl)methoxy]-6-methyl-7-oxatricyclo-[4.2.1.0$^{2,4}$]nonane | 5% |
| water | 95% |

The compound is added directly to the water with stirring to produce the solution, which may then be packaged for use.

EXAMPLE I

Dust

| | |
|---|---|
| (1α,2α,4α,5β,6α)-(+/−)-5-[(2-chloro-6-fluorophenyl)methoxy]-6-methyl-7-oxatricyclo-[4.2.1.0$^{2,4}$]nonane | 10% |
| attapulgite | 10% |
| Pyrophyllite | 80% |

The active ingredient is sprayed onto the attapulgite and then passed through a hammer-mill to produce particles substantially all below 200 microns. The ground concentrate is then blended with powdered pyrophyllite until homogeneous.

UTILITY

Test results indicate compounds of this invention are active postemergence and, in particular, preemergence herbicides. Many compounds in this invention are useful for the control of selected grass and broadleaf weeds with tolerance to important agronomic crops such as barley (*Hordeum vulgare*), corn (*Zea mays*), cotton (*Gossypium hirsutum*), rape (*Brassica napus*), rice (*Oryza sativa*), sorghum (*Sorghum bicolor*), soybean (*Glycine max*), sugar beet (*Beta vulgaris*), wheat (*Triticum aestivum*), and to vegetable crops. Grass and broadleaf weed species controlled include, but are not limited to, barnyardgrass (*Echinochloa crus-galli*), blackgrass (*Alopecurus myosuroides*), crabgrass (Digitaria spp.), duck salad (*Heteranthera limosa*), foxtail (Setaria spp.), velvetleaf (*Afutilon theophrasti*), lambsquarters (Chenopodium spp.), and umbrella sedge (*Cyperus difformis*). Several compounds in this invention are particularly useful for the control of barnyardgrass and selected broadleaf weeds such as duck salad and umbrella sedge in upland and paddy rice. Compound 3 in Table C demonstrates outstanding control of barnyardgrass, duck salad and umbrella sedge with no injury to rice.

Effective rates of application for compounds of this invention are determined by a number of factors. These factors include: formulation selected, method of application, amount and type of vegetation present, growing conditions, etc. In general, the effective rates of application for compounds of this invention are rates from 0.01 to 20 kg/ha with a preferred rate range of 0.03 to 1 kg/ha. One skilled in the art can easily determine effective application rates necessary for desired level of weed control.

Compounds of this invention may be used alone or in combination with other commercial herbicides, insecticides, or fungicides. The following list exemplifies some of the herbicides suitable for use in mixtures. A combination of a compound from this invention with one or more of the following herbicides may be particularly useful for weed control.

| Common Name | Chemical Name |
|---|---|
| acetochlor | 2-chloro-N-(ethoxymethyl)-N-(2-ethyl-6-methylphenyl)acetamide |
| acifluorfen | 5-[2-chloro-4-(trifluoromethyl)phenoxy]-2-nitrobenzoic acid |
| aclonifen | 2-chloro-6-nitro-3-phenoxybenzenamine |
| acrolein | 2-propenal |
| alachlor | 2-chloro-N-(2,6-diethylphenyl)-N-(methoxymethyl)acetamide |
| alloxydim | methyl 2,2-dimethyl-4,6-dioxo-5-[1-[(2-propenyloxy)amino]butylidene] cyclohexanecarboxylate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| anilofos | S-[2-[(4-chlorophenyl)(1-methylethyl)amino]-2-oxoethyl] O,O-dimethyl phosphorodithioate |
| asulam | methyl [(4-aminophenyl)sulfonyl]carbamate |
| atrazine | 6-chloro-N-ethyl-N'-(1-methylethyl)-1,3,5-triazine-2,4-diamine |
| aziprotryne | 4-azido-N-(1-methylethyl)-6-methylthio-1,3,5-triazin-2-amine |
| azoluron | N-(1-ethyl-1H-pyrazol-5-yl)-N'-phenylurea |
| barban | 4-chloro-2-butynyl 3-chlorocarbamate |
| benazolin | 4-chloro-2-oxo-3(2H)-benzothiazoleacetic acid |
| benfluralin | N-butyl-N-ethyl-2,6-dinitro-4-(trifluoromethyl)benzenamine |
| bensulfuron | 2-[[[[[(4,6-dimethoxy-2-pyrimidinyl)amino]methylcarbonyl]aino]sulfonyl]methyl]benzoic acid, methyl ester |
| bensulide | O,O-bis(1-methylethyl) S-[2-[(phenylsulfonyl)amino]ethyl]phosphorodithioate |
| bentazon | 3-(1-methylethyl)-(1H)-2,1,3-benzo- |

-continued

| Common Name | Chemical Name |
|---|---|
| | thiadiazin-4(3H)-one, 2,2-dioxide |
| benzofluor | N-[4-(ethylthio)-2-(trifluoromethyl)-phenyl]methanesulfonamide |
| benzoylprop | N-benzoyl-N-(3,4-dichlorophenyl)-DL-alanine |
| benzthiazuron | N-2-benzothiazolyl-N'-methylurea |
| bialaphos | 4-(hydroxymethylphosphinyl)-L-2-aminobutanoyl-L-alanyl-L-alanine |
| bifenox | methyl 5-(2,4-dichlorophenoxy)-2-nitrobenzoate |
| bromacil | 5-bromo-6-methyl-3-(1-methylpropyl)-2,4-(1H,3H)pyrimidinedione |
| bromobutide | (+)2-bromo-3,3-dimethyl-N-(1-methyl-1-phenylethyl)butanamide |
| bromofenoxim | 3,5-dibromo-4-hydroxybenzaldhyde O-(2,4-dinitrophenyl)oxime |
| bromoxynil | 3,5-dibromo-4-hydroxybenzonitrile |
| bromuron | N'-(4-bromophenyl)-N,N-dimethylurea |
| buminafos | dibutyl [1-(butylamino)cyclohexyl]-phosphonate |
| butachlor | N-(butoxymethyl)-2-chloro-N-(2,6-diethylphenyl)acetamide |
| butamifos | O-ethyl O-(5-methyl-2-nitrophenyl)-(1methylpropyl)phosphoramidothioate |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)carbamothioate |
| cacodylic acid | dimethyl arsinic oxide |
| carbetamide | (R)-N-ethyl-2-[[(phenylamino)carbonyl]-oxy]propanamide |
| CDAA | 2-chloro-N,N-di-2-propenylacetamide |
| CDEC | 2-chloroallyl diethyldithiocarbamate |
| chlomethoxyfen | 4-(2,4-dichlorophenoxy)-2-methoxy-1-nitrobenzene |
| chloramben | 3-amino-2,5-dichlorobenzoic acid |
| chlorbromuron | 3-(4-bromo-3-chlorophenyl)-1-methoxy-1-methylurea |
| chlorbufam | 1-methyl-2-propynl(3-chlorophenyl)-carbamate |
| chlorfenac | 2,3,6-trichlorobenzeneacetic acid |
| chlorflurecol-methyl | methyl 2-chloro-9-hydroxy-9H-fluorene-methyl 9-carboxylate |
| chloridazon | 5-amino-4-chloro-2-phenyl-3(2H)-pyridazinone |
| chlorimuron | 2-[[[[(4-chloro-6-methoxy-2-pyrimidinyl)ethylamino]carbonyl]amino]sulfonyl]benzoic acid, ethyl ester |
| chlornitrofen | 1,3,5-trichloro-2-(4-nitrophenoxy)-benzene |
| chloropicrin | trichloronitromethane |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]-benzenesulfonamide |
| chlorthal-dimethyl | dimethyl 2,3,5,6-tetrachloro-1,4-benzenedicarboxylate |
| chlorthiamid | 2,6-dichlorobenzene carbothioamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo-[2.2.1]heptane |
| clethodim | (E,E)-(±)-2-[1-[[(3-chloro-2-propenyl)-oxy]imino]propyl]-5-[2-(ethylthio)-propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy)-imino]butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methylpropanenitrile |

-continued

| Common Name | Chemical Name |
|---|---|
| cycloate | S-ethyl cyclohexylethylcarbamothioate |
| cycloxydim | 2-[1-ethoxyimino)butyl]-3-hydroxy-5-(tetrahydro-2H-thiopyran-3-yl)-2-cyclohexene-1-one |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmedipham | ethyl [3-[[(phenylamino)carbonyl]oxy]phenyl]carbamate |
| desmetryn | 2-(isopropylamino)-4-(methylamino)-6-(methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | ($\pm$)-2-(2,4-dichlorophenoxy)propanoic acid |
| diclofop-methyl | ($\pm$)-2-[4-(2,4-dichlorophenoxy)phenoxy]-propanoic acid, methyl ester |
| diethatyl | N-(chloroacetyl)-N-(2,6-diethylphenyl)-glycine |
| difenoxuron | N'-[4-(4-methoxyphenoxy)phenyl]-N,N-dimethylurea |
| difenzoquat | 1,2-dimethyl-3,5-diphenyl-1H-pyrazolium ion |
| diflufenican | N-(2,4-difluorophenyl)-2-(3-trifluoromethylphenoxy)pyridine-3-carboxamide |
| dimefuron | N'-[3-chloro-4-[5-(1,1-dimethylethyl)-2-oxo-1,3,4-oxadiazol-3(2H)-yl]phenyl]-N,N-dimethylurea |
| dimethachlor | 2-chloro-N-(2,6-dimethylphenyl)-N-(2-methoxyethyl)acetamide |
| dimethametryn | N-(1,2-dimethylpropyl)-N'-ethyl-6-(methylthio)-1,3,5-triazine-2,4-diamine |
| dimethipin | 2,3-dihydro-5,6-dimethyl-1,4-dithiin 1,1,4,4-tetraoxide |
| dimethylarsinic | dimethylarsinic acid |
| dinitramine | $N^3,N^3$-*diethyl-2,4-dinitro-6-(trifluoromethyl)*-1,3-benzenediamine |
| dinoseb | 2-(1-methylpropyl)-4,6-dinitrophenol |
| dinoterb | 2-(1,1-dimethylethyl)-4,6-dinitrophenol |
| diphenamid | N,N-dimethyl-α-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]-pyrazinediium ion |
| diuron | N'-(3,4-dichlorophenyl)-N,N-dimethylurea |
| DNOC | 2-methyl-4,6-dinitrophenol |
| DPX-V9360 | 2-[[(4,6-dimethoxypyrimidin-2-yl)aminocarbonyl]aminosulfonyl]-N,N-dimethyl 3-pyridinecarboxamide |
| DSMA | disodium salt of MAA |
| dymron | N-(4-methylphenyl)-N'-(1-methyl-1-phenylethyl)urea |
| eglinazine-ethyl | N-[4-chloro-6-(ethylamino)-1,3,5-triazin-2-yl]glycine ethyl ester |
| endothall | 7-oxabicyclo[2.2.1]heptane-2,3-dicarboxylic acid |
| EPTC | S-ethyl dipropylcarbamothioate |
| ethalfluralin | N-ethyl-N-(2-methyl-2-propenyl)-2,6-dinitro-4-(trifluoromethyl)benzenamine |
| ethidimuron | N-[5-(ethylsulfonyl)-1,3,4-thiadiazol-2-yl]-N,N'-dimethylurea |
| ethofumesate | ($\pm$)-2-ethoxy-2,3-dihydro-3,3-dimethyl-5-benzofuranyl methanesulfonate |
| fenac | 2,3,6-trichlorobenzeneacetic acid |
| fenoprop | ($\pm$)-2-(2,4,5-trichlorophenoxy)propanoic acid |
| fenoxaprop | ($\pm$)-2-[4-[(6-chloro-2-benzoxazolyl)oxy]- |

-continued

| Common Name | Chemical Name |
|---|---|
| | phenoxy]propanoic acid |
| fenuron | N,N-dimethyl-N'-phenylurea |
| fenuron TCA | Salt of fenuron and TCA |
| flamprop-M-isopropyl | 1-methylethyl N-benzoyl-N-(3-chloro-4-fluorophenyl)-D-alanine |
| flamprop-methyl | methyl N-benzoyl-N-(3-chloro-4-fluorophenyl)-DL-alaninate |
| fluazifop | (±)-2-[4-[[5-(trifloromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-(trifluoromethyl)-phenyl]urea |
| fluralin | N-butyl-N-ethyl-2,6-dinitro-4-(trifluoromethyl)benzenamine |
| fluorodifen | p-nitrophenyl α,α,α-trifluoro-2-nitro-p-tolyl ether |
| fluoroglycofen | carboxymethyl 5-[2-chloro-4-(trifluoromethyl)phenoxy]-2-nitrobenzoate |
| flurecol-butyl | butyl 9-hydroxy-9H-fluorene-9-carboxylate |
| fluridone | 1-methyl-3-phenyl-5-[3-(trifluoromethyl)phenyl]-4(1H)-pyridinone |
| flurochloridone | 3-chloro-4-(chloromethyl)-1-[3-(trifluoromethyl)phenyl]-2-pyrrolidinone |
| fluroxypyr | [(4-amino-3,5-dichloro-6-fluoro-2-pyridinyl)oxy]acetic acid |
| fomesafen | 5-[2-chloro-4-(trifluoromethyl)phenoxy]-N-(methylsulfonyl)-2-nitrobenzamide |
| fosamine-ammonium | ethyl hydrogen (aminocarbonyl)-phosphonate ammonium ethyl |
| glufosinate-ammonium | ammonium 2-amino-4-(hydroxymethylphosphinyl)butanoate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (±)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isocarbamid | N-(2-methylpropyl)-2-oxo-1-imidazolidine-carboxamide |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]-phenyl-(1,1-dimethylethyl)carbamate |
| lactofen | (±)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPA-thioethyl | S-ethyl (4-chloro-2-methylphenoxy)-ethanethioate |
| MCPB | 4-(4-chloro-2-methylphenoxy)butanoic |

-continued

| Common Name | Chemical Name |
|---|---|
| mecoprop | (±)-2-(4-chloro-2-methylphenoxy)-propanoic acid |
| mefenacet | 2-(2-benzothiazolyloxy)-N-methyl-N-phenyl acetamide |
| mefluidide | N-[2,4-dimethyl-5-[[(trifluoromethyl)-sulfonyl]amino]phenyl]acetamide |
| metamitron | 4-amino-3-methyl-6-phenyl-1,2,4-triazin-5(4H)-one |
| metazachlor | 2-chloro-N-(2,6-dimethylphenyl)-N-(1(H)-pyrazol-1-ylmethyl)acetamide |
| methabenzthiazuron | 1,3-dimethyl-3-(2-benzothiazolyl)urea |
| methalpropalin | N-(2-methyl-2-propenyl)-2,6-dinitro-N-propyl-4-(trifluoromethyl)benzenamide |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| methoxyphenone | (4-methoxy-3-methylphenyl)(3-methyl-phenyl)methanone |
| methyldymron | N-methyl-N'-(1-methyl-1-phenylethyl)-N-phenylurea |
| metobromuron | N'-(4-bromophenyl)-N-methoxy-N-methylurea |
| metolachlor | 2-chloro-N-(2-ethyl-6-methylphenyl)-N-(2-methoxy-1-methylethyl)acetamide |
| metoxuron | N'-(3-chloro-4-methoxyphenyl)-N,N-dimethylurea |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]amino]-sulfonyl]benzoic acid, methyl ester |
| MH | 1,2-dihydro-3,6-pyridazinedione |
| molinate | S-ethyl hexahydro-1H-azepine-1-carbothioate |
| monalide | N-(4-chlorophenyl)-2,2-dimethyl-pentanamide |
| monolinuron | 3-(p-chlorophenyl)-1-methoxy-1-methylurea |
| monuron | N'-(4-chlorophenyl)-N,N-dimethylurea |
| MSM | monosodium salt of MAA |
| naproanilide | 2-(2-naphthalenyloxy)-N-phenyl-propanamide |
| napropamide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorophenyl)-1-methylurea |
| nitralin | 4-methylsulfonyl-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aα,4α,5α,7α,7aα-isomer |
| norflurazon | 4-chloro-5-(methylamino)-2-[3-(tri-fluoromethyl)phenyl]-3(2H)-pyridazinone |
| orbencarb | S-[2-(chlorophenyl)methyl]diethyl-carbamothioate |
| oryzalin | 4-(dipropylamino)-3,5-dinitro-benzenesulfonamide |
| oxadiazon | 3-[2,4-dichloro-5-(1-methylethoxy)-phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methane-sulfonamide |
| phenisopham | 3-[[(1-methylethoxy)carbonyl]amino]-phenyl ethylphenylcarbamate |

-continued

| Common Name | Chemical Name |
|---|---|
| phenmedipham | 3-[(methoxycarbonyl)amino]phenyl (3-methylphenyl)carbamate |
| picloram | 4-amino-3,5,6-trichloro-2-pyridine-carboxylic acid |
| piperophos | S-[2-(2-methyl-1-piperidinyl)-2-oxoethyl]O,O-dipropyl phosphorodithioate |
| pretilachlor | 2-chloro-N-(2,6-diethylphenyl)-N-(2-propoxyethyl)acetamide |
| procyazine | 2-[[4-chloro-6-(cyclopropylamino)-1,3,5-triazine-2-yl]amino]-2-methylpropane-nitrile |
| prodiamine | 2,4-dinitro-N3,N3-dipropyl-6-(trifluoromethyl)-1,3-benzenediamine |
| profluralin | N-(cyclopropylmethyl)-2,6-dinitro-N-propyl-4-(trifluoromethyl)benzenamine |
| proglinazine-ethyl | N-[4-chloro-6-[(1-methylethyl)amino]-1,3,5-triazin-2-yl]glycine ethyl ester |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenyl-acetamide |
| propanil | N-(3,4-dichlorophenyl)propanamide |
| propaquizafop | 2-[[(1-methylethylidene)amino]oxy]ethyl 2-[4-[(6-chloro-2-quinoxalinyl)oxy]-phenoxy]propanoate |
| propazine | 6-chloro-N,N'-bis(1-methylethyl)-1,3,5-triazine-2,4-diamine |
| propham | 1-methylethyl phenylcarbamate |
| propyzamide | 3,5-dichloro-N-(1,1-dimethyl-2-propynl)-benzamide |
| prosulfalin | N-[[4-(dipropylamino)-3,5-dinitro-phenyl]sulfonyl]-S,S-dimethyl-sulfilimine |
| prosulfocarb | S-benzyldipropylthiocarbamate |
| prynachlor | 2-chloro-N-(1-methyl-2-propynyl)-acetanilide |
| pyrazon | 5-amino-4-chloro-2-phenyl-3(2H)-pyridazinone |
| pyrazosulfuron-ethyl | ethyl 5-[[[[(4,6-dimethoxy-2-pyrimidinyl)amino]carbonyl]amino]-sulfonyl]-1-methyl-1H-pyrazole-4-carboxylate |
| pyrazoxyfen | 2-[[4-(2,4-dichlorobenzoyl)-1,3-dimethyl-1H-pyrazol-5-yl]oxy]-1-phenylethanone |
| pyridate | O-(6-chloro-3-phenyl-4-pyridazinyl) S-octyl carbonothioate |
| quizalofop ethyl | (±)-2-[4-[(6-chloro-2-quinoxalinyl)-oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethyl-thio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| simetryn | N,N'-diethyl-6-(methylthio)-1,3,5-triazine-2,4-diamine |
| sodium chlorate | sodium chlorate |
| sodium mono-chloroacetate | chloroacetic acid, sodium salt |
| sulfometuron methyl | 2-[[[[(4,6-dimethyl-2-pyrimidinyl)-amino]carbonyl]amino]sulfonyl]-benzoic acid, methyl ester |
| 2,4,5-T | (2,4,5-trichlorophenoxy)acetic acid |
| 2,3,6-TBA | 2,3,6-trichlorobenzoic acid |
| TCA | trichloroacetic acid |
| tebutam | 2,2-dimethyl-N-(1-methylethyl)-N-(phenylmethyl)propanamide |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]- |

| Common Name | Chemical Name |
|---|---|
| | acetamide |
| terbumeton | N-(1,1-dimethylethyl)-N40-ethyl-6-methoxy-1,3,5-triazine-2,4-diamine |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thifensulfuron | 3-[[[[(4-methoxy-6-methyl-1,3,5,triazin-2-yl)amino]carbonyl]amino]sulfonyl]-2-thiophenecarboxylic acid, methyl ester |
| thiameturon-methyl | methyl 3-[[[[(4-methoxy-6-methyl-1,3,5-triazin-2-yl)amino]carbonyl]amino]-sulfonyl]2-thiophenecarboxylate |
| thiazafluron | N,N'-dimethyl-N-[5-(trifluoromethyl)-1,3,4-thiadiazol-2-yl]urea |
| thiobencarb | S-[(4-chlorophenyl)methyl]diethylcarbamothioate |
| tiocarbazil | S-(phenylmethyl) bis(1-methylpropyl)-carbamothioate |
| tralkoxydim | 2-[1-(ethoxyimino)propyl]-3-hydroxy-5-(2,4,6-trimethylphenyl)-2-cyclohexen-1-one |
| triallate | S-(2,3,3-trichloro-2-propenyl) bis(1-methylethyl)carbamothioate |
| triasulfuron | 2-(2-chloroethoxy)-N-[[(4-methoxy-6-methyl-1,3,5-triazin-2-yl)amino]-carbonyl]benzenesulfonamide |
| tribenuron methyl | 2-[[[[N-(4-methoxy-6-methyl-1,3,5-triazine-2-yl)-N-methylamino]-carbonyl]amino]-sulfonyl]benzoic acid, methyl ester |
| triclopyr | [(3,5,6-trichloro-2-pyridinyl)oxy]-acetic acid |
| tridiphane | (+)2-(3,5-dichlorophenyl)-2-(2,2,2-trichloroethyl)oxirane |
| trietazine | 6-chloro-N,N,N'-triethyl-1,3,5-triazine-2,4-diamine |
| trifluralin | 2,6-dinitro-N,N-dipropyl-4-(trifluoromethyl)benzenamine |
| trimeturon | 1-(p-chlorophenyl)-2,3,3-trimethyl-pseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

Herbicidal properties of the subject compounds were discovered in a number of greenhouse tests. Test procedures and results follow.

COMPOUND TABLE

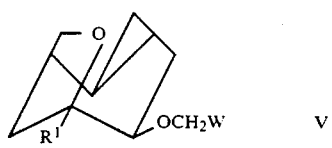

V

| Compound | R¹ | W | Physiochemical/Spectral Data (δ in CDCl₃) |
|---|---|---|---|
| 1 | CH₃ | 2-Cl, 6-FPh | m.p. 69-71° C. |
| 2 | CH₃ | 2,4-F₂Ph | NMR: 7.48 (m, 1H), 6.95(m, 1H), 6.79(m, 1H), 4.79(d, 1H), 4.62 (d, 1H), 3.6(dd, 1H), 3.53 (m, 2H), 2.60(m, 1H), 1.6 (m, 1H), 1.50(dd, 2H), 1.31 s, 3H), 1.1(m, 1H), 0.9(m, 1H), 0.58(m, 1H). |

COMPOUND TABLE-continued

| | | | |
|---|---|---|---|
| 3 | $CH_3$ | 2-ClPh | NMR: 7.6(d, 1H), 7.31(D, 1H), 7.11(m, 2H), 4.88(d, 1H), 4.70 (d, 1H), 3.61(m, 2H), 3.55 (d, 1H), 2.60(m, 1H), 1.6 (m, 1H), 1.5(dd, 2H), 1.39 (s, 3H), 1.16(m, 1H), 0.91 (m, 1H), 0.59(m, 1H). |
| 4 | $CH_3$ | 2-F-Ph | NMR: 7.55(dd, 1H), 7.22 (m, 1H), 7.10(dd, 1H), 7.01 (dd, 1H), 4.82(d, 1H), 4.71 (d, 1H), 3.55(m, 3H), 2.60 (m, 1H), 1.60(m, 1H), 1.49 (m, 2H), 1.32(s, 3H), 1.1 (m, 1H), 0.9(m, 1H), 0.59 (m, 1H). |
| 5 | $CH_3$ | Ph | NMR: 7.3(m, 5H), 4.82(d, 1H), 4.61(d, 1H), 3.60(m, 1H), 3.52 (m, 2H), 2.59(m, 1H), 1.6 (m, 1H), 1.49(m, 2H), 1.34 (s, 3H), 1.01(m, 1H), 0.90 (m, 1H), 0.59(m, 1H). |
| 6 | $CH_2CH_3$ | Ph | NMR: 7.2(m, 5H), 4.78(d, 1H), 4.61(d, 1H), 3.55(m, 3H), 2.59 (m, 1H), 1.7(m, 2H), 1.6–1.2 (m, 3H), 1.00(m, 1H), 0.92 (m, 1H), 0.72(t, 3H), 0.60 (m, 1H). |
| 7 | $CH_2CH_3$ | 2-FPh | NMR: 7.5(m, 1H), 7.3–6.92 (m, 3H), 4.80(d, 1H), 4.67 (d, 1H), 3.6(d, 1H), 3.55 (m, 2H), 2.59(m, 1H), 1.8–1.5 (m, 4H), 1.20(d, 1H), 1.1 (m, 1H), 0.9(m, 1H), 0.72 (t, 3H), 0.59(m, 1H). |
| 8 | $CH_2CH_3$ | 2,6-$F_2$Ph | m.p. 51–53° C. |
| 9 | $CH_2CH_3$ | 2-Cl, 6-FPh | m.p. 73–75° C. |
| 10 | $CH_2CH_3$ | 2-ClPh | NMR: 7.60(m, 1H), 7.2(m, 3H), 4.85(d, 1H), 4.70(d, 1H), 3.64 (d, 1H), 3.58(m, 2H), 2.60 (m, 1H), 1.8–1.4(m, 4H), 1.30 (d, 1H), 1.19(m, 1H), 0.94 (m, 1H), 0.76(t, 3H), 0.60 (m, 1H). |
| 11 | $CH_2CH_3$ | 2-$CH_3$Ph | NMR: 7.35(m, 1H), 7.18(m, 3H), 4.829d, 1H), 4.58(d, 1H), 3.55 (m, 3H), 2.59(m, 1H), 2.40 (s, 3H), 1.6(m, 4H), 1.5(d, 1H), 1.10(m, 1H), 0.92(m, 1H), 0.70 (t, 3H), 0.60(m, 1H). |
| 12 | $CH_3$ | 2,6-$F_2$Ph | NMR: 7.22(m, 1H), 6.85(t, 2H), 4.89(d, 1H), 4.67(d, 1H), 3.5 (m, 3H), 2.59(m, 1H), 1.65–1.1 (m, 4H), 1.23(s, 3H), 0.89 (m, 1H), 0.60(m, 1H). |
| 13 | $CH_3$ | 2-$CH_3$Ph | NMR: 7.4–7.1(m, 4H), 4.82 (d, 1H), 4.59(d, 1H), 3.5 (m, 3H), 2.59(m, 1H), 2.40 (s, 3H), 1.31(s, 3H), 1.6–1.2 (m, 3H), 1.01(m, 1H), 0.91 (m, 1H), 0.6(m, 1H). |

TEST A

Seeds of barley (*Hordeum vulgare*), barnyardgrass (*Echinochloa crus-galli*), bedstraw (*Galium aparine*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (Digitaria spp.), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aeastivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response means no test result.

TABLE A

| Rate (200 g/ha) | COMPOUND | | | | |
|---|---|---|---|---|---|
| | 1 | 2 | 3 | 4 | 5 |
| POSTEMERGENCE | | | | | |
| Barley | 0 | 0 | 0 | 0 | 3 |
| Barnyardgrass | 9 | 4 | 9 | 9 | 9 |
| Bedstraw | 2 | 0 | 0 | 0 | 0 |
| Blackgrass | 0 | 0 | 0 | 6 | 2 |
| Cheatgrass | 0 | 0 | 0 | 2 | 2 |
| Chickweed | 2 | 0 | 0 | 0 | 0 |
| Cocklebur | 0 | 0 | 0 | 0 | 0 |
| Corn | 2 | 0 | 0 | 0 | 2 |
| Cotton | 0 | 0 | 0 | 0 | 0 |
| Crabgrass | 3 | 0 | 2 | 2 | 7 |
| Giant foxtail | 1 | 0 | 1 | 6 | 5 |
| Lambsquarters | 5 | 0 | 0 | 0 | 0 |
| Morningglory | 0 | 0 | 0 | 0 | 0 |
| Nutsedge | 0 | 0 | 5 | 0 | 0 |
| Rape | 0 | 0 | 0 | 0 | 0 |
| Rice | 0 | 2 | 1 | 2 | 7 |
| Sorghum | 0 | 0 | 0 | 0 | 0 |
| Soybean | 0 | 0 | 0 | 0 | 2 |
| Sugar beet | 0 | 0 | 0 | 0 | 2 |
| Velvetleaf | 4 | 3 | 5 | 7 | 3 |
| Wheat | 0 | 0 | 0 | 3 | 5 |
| Wild oat | 0 | 0 | 0 | 0 | 0 |

| Rate (50 g/ha) | COMPOUND | | | | |
|---|---|---|---|---|---|
| | 1 | 2 | 3 | 4 | 5 |
| POSTEMERGENCE | | | | | |
| Barley | 0 | 0 | 0 | 0 | 0 |
| Barnyardgrass | 5 | 2 | 7 | 8 | 6 |
| Bedstraw | 0 | 0 | 0 | 0 | 0 |
| Blackgrass | 0 | 0 | 0 | 0 | 0 |
| Cheatgrass | 0 | 0 | 0 | 0 | 0 |
| Chickweed | 0 | 0 | 0 | 0 | 0 |
| Cocklebur | 0 | 0 | 0 | 0 | 0 |
| Corn | 0 | 0 | 0 | 0 | 0 |
| Cotton | 0 | 0 | 0 | 0 | 0 |
| Crabgrass | 1 | 0 | 0 | 1 | 0 |
| Giant foxtail | 0 | 0 | 0 | 0 | 2 |
| Lambsquarters | 0 | 0 | 0 | 0 | 0 |
| Morningglory | 0 | 0 | 0 | 0 | 0 |
| Nutsedge | 0 | 0 | 0 | 0 | 0 |
| Rape | 0 | 0 | 0 | 0 | 0 |
| Rice | 0 | 0 | 2 | 1 | 2 |
| Sorghum | 0 | 0 | 0 | 0 | 0 |
| Soybean | 0 | 0 | 0 | 0 | 0 |
| Sugar beet | 0 | 0 | 0 | 0 | 0 |
| Velvetleaf | 3 | 0 | 3 | 3 | 3 |
| Wheat | 0 | 0 | 0 | 2 | 2 |
| Wild oat | 0 | 0 | 0 | 0 | 0 |

| Rate (200 g/ha) | COMPOUND | | | | |
|---|---|---|---|---|---|
| | 1 | 2 | 3 | 4 | 5 |
| PREEMERGENCE | | | | | |
| Barley | 2 | 0 | 0 | 0 | 0 |
| Barnyardgrass | 10 | 9 | 10 | 10 | 10 |
| Bedstraw | 6 | 0 | 6 | 3 | 6 |
| Blackgrass | 9 | 2 | 3 | 9 | 10 |
| Cheatgrass | 8 | 3 | 8 | 10 | 9 |
| Chickweed | 6 | 6 | 3 | 6 | 6 |
| Cocklebur | 7 | 0 | 0 | 0 | 0 |
| Corn | 5 | 7 | 5 | 7 | 4 |
| Cotton | 2 | 2 | 0 | 0 | 0 |
| Crabgrass | 8 | 7 | 9 | 9 | 10 |
| Giant foxtail | 10 | 9 | 10 | 9 | 10 |

TABLE A-continued

| Lambsquarters | 8 | 10 | 8 | 7 | 9 |
|---|---|---|---|---|---|
| Morningglory | 0 | 0 | 0 | 0 | 0 |
| Nutsedge | 0 | 0 | 0 | 0 | 9 |
| Rape | 2 | 0 | 7 | 3 | 4 |
| Rice | 2 | 2 | 0 | 0 | 0 |
| Sorghum | 2 | 0 | 0 | 0 | 0 |
| Soybean | 0 | 0 | 0 | 1 | 0 |
| Sugar beet | 6 | — | 3 | 3 | 2 |
| Velvetleaf | 3 | 4 | 4 | 5 | 6 |
| Wheat | 0 | 0 | 0 | 3 | 2 |
| Wild oat | 6 | 4 | 6 | 6 | 4 |

| Rate (50 g/ha) | COMPOUND | | | | |
|---|---|---|---|---|---|
| | 1 | 2 | 3 | 4 | 5 |
| PREEMERGENCE | | | | | |
| Barley | 0 | 0 | 0 | 0 | 0 |
| Barnyardgrass | 10 | 9 | 10 | 10 | 10 |
| Bedstraw | 2 | 0 | 2 | 2 | 5 |
| Blackgrass | 6 | 2 | 3 | 6 | 7 |
| Cheatgrass | 0 | 0 | 0 | 3 | 2 |
| Chickweed | 0 | 0 | 4 | 5 | 5 |
| Cocklebur | 3 | 0 | 0 | 0 | 0 |
| Corn | 2 | 2 | 1 | 0 | 0 |
| Cotton | 2 | 2 | 0 | 0 | 0 |
| Crabgrass | 9 | 3 | 6 | 3 | 6 |
| Giant foxtail | 10 | 8 | 10 | 9 | 9 |
| Lambsquarters | 7 | 0 | 4 | 5 | 2 |
| Morningglory | 0 | 0 | 0 | 0 | 0 |
| Nutsedge | 0 | 0 | 0 | 0 | 0 |
| Rape | 0 | 0 | 0 | 0 | 0 |
| Rice | 0 | 2 | 2 | 0 | 0 |
| Sorghum | 0 | 0 | 0 | 0 | 0 |
| Soybean | 1 | 0 | 0 | 0 | 0 |
| Sugar beet | 0 | 0 | 0 | 2 | 0 |
| Velvetleaf | 5 | 3 | 2 | 3 | 2 |
| Wheat | 0 | 0 | 0 | 0 | 0 |
| Wild oat | 0 | 0 | 0 | 0 | 0 |

TEST B

The compounds evaluated in this test were formulated in a non-phytoxic solvent and applied to the soil surface before plant seedlings emerged (preemergence application), to water that covered the soil surface (paddy application), and to plants that were in the one-to-four leaf stage (postemergence application). A sandy loam soil was used for the preemergence and postemergence tests, while a silt loam soil was used in the paddy test. Water depth was approximately 2.5 cm for the paddy test and was maintained at this level for the duration of the test.

Plant species in the preemergence and postemergence tests consisted of barley (Hordeum vulgare), bedstraw (*Galium aparine*), blackgrass (*Alopecurus myosuroides*), chickweed (*Stillaria media*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), pigweed (Amaranthusretroflexus), rape (*Brassica napus*), ryegrass (*Lolium multiflorum*), sorghum (*Sorghum bicolor*), soybean (*Glycine max*), speedwell (*Veronica persica*), sugar beet (*Beta vulgaris*), velvetleaf (*abutilon theophrasti*), wheat (*Triticum aeasivum*), wild buckwheat (*Polygonum convolvul-*

*vus*), and wild oat (*Avena fatua*). All plant species were planted one day before application of the compound for the preemergence portion of this test. Plantings of these species were adjusted to produce plants of appropriate size for the postemergence portion of the test. Plant species in the paddy test consisted of barnyardgrass (*Echinochloa crus-galli*), rice (*Oryza sativa*), umbrella sedge (*Cyperus difformis*) and duck salad (*Heteranthera limosa*).

All plant species were grown using normal greenhouse practices. Visual evaluations of injury expressed on treated plants, when compared to untreated controls, were recorded approximately fourteen to twenty-one days after application of the test compound. Plant response ratings, summarized in Table B, were recorded on a 0 to 10 scale where 0 is no effect and 10 is complete control. A dash (-) response means no test result.

TABLE B

| Rate (250 g/ha) | COMPOUND | | | |
|---|---|---|---|---|
| | 1 | 3 | 4 | 5 |
| POSTEMERGENCE | | | | |
| Barley Igri | 0 | 0 | 2 | 3 |
| Bedstraw | 0 | 0 | 0 | 0 |
| Blackgrass | 0 | 0 | 9 | 10 |
| Chickweed | 0 | 0 | 0 | — |
| Corn | 2 | 0 | 6 | 5 |
| Cotton | 3 | 0 | 0 | 0 |
| Crabgrass | 3 | 0 | 2 | 2 |
| Downy brome | 0 | 0 | 0 | 0 |
| Duck salad | 5 | 8 | 9 | 9 |
| Giant foxtail | 3 | 5 | 2 | 3 |
| Lambsquarters | 0 | 0 | — | — |
| Morningglory | 0 | 0 | 0 | 3 |
| Pigweed | 0 | 0 | 0 | 4 |
| Rape | 0 | 0 | 0 | 0 |
| Ryegrass | 9 | 3 | 9 | 5 |
| Sorghum | 0 | 2 | 0 | 2 |
| Soybean | 2 | 0 | 0 | 4 |
| Speedwell | 0 | 0 | 0 | — |
| Sugar beet | 0 | 0 | 0 | 0 |
| Velvetleaf | 0 | 3 | 0 | 5 |
| Wheat | 0 | 0 | 7 | 3 |
| Wild buckwheat | 0 | 0 | 0 | 0 |
| Wild oat | 0 | 0 | 3 | 2 |
| Barnyardgrass | 10 | 10 | 10 | 10 |
| Rice Japonica | 7 | 7 | 10 | 9 |
| Umbrella sedge | 9 | 9 | 10 | 9 |

| Rate (125 g/ha) | COMPOUND | | | |
|---|---|---|---|---|
| | 1 | 3 | 4 | 5 |
| POSTEMERGENCE | | | | |
| Barley Igri | 0 | 0 | 0 | 2 |
| Bedstraw | 0 | 0 | 0 | 0 |
| Blackgrass | 0 | 0 | 9 | 10 |
| Chickweed | 0 | 0 | 0 | 0 |
| Corn | 0 | 0 | 2 | 5 |
| Cotton | 0 | 0 | 0 | 0 |
| Crabgrass | 0 | 0 | 0 | 0 |
| Downy brome | 0 | 0 | 0 | 0 |
| Duck salad | 1 | 7 | 9 | 8 |
| Giant foxtail | 2 | 2 | 0 | 0 |
| Lambsquarters | — | 0 | 0 | 0 |
| Morningglory | 0 | 0 | 0 | 0 |
| Pigweed | 0 | 0 | 0 | 2 |
| Rape | 0 | 0 | 0 | 0 |
| Ryegrass | 3 | 0 | 7 | 3 |
| Sorghum | 0 | 0 | 0 | 0 |
| Soybean | 0 | 0 | 0 | 1 |
| Speedwell | 0 | 0 | 0 | 0 |
| Sugar beet | 0 | 0 | — | 0 |
| Velvetleaf | 0 | 2 | 0 | 3 |
| Wheat | 0 | 0 | 3 | 0 |
| Wild buckwheat | 0 | 0 | 0 | 0 |
| Wild oat | 0 | 0 | 0 | 0 |
| Barnyardgrass | 10 | 10 | 10 | 10 |
| Rice Japonica | 6 | 7 | 9 | 9 |
| Umbrella sedge | 9 | 9 | 9 | 9 |

TABLE B-continued

| Rate (62 g/ha) | COMPOUND | | | |
|---|---|---|---|---|
| | 1 | 3 | 4 | 5 |
| POSTEMERGENCE | | | | |
| Barley Igri | 0 | 0 | 0 | 0 |
| Bedstraw | 0 | 0 | 0 | 0 |
| Blackgrass | 0 | 0 | 3 | 2 |
| Chickweed | 0 | 0 | 0 | 0 |
| Corn | 0 | 0 | 0 | 3 |
| Cotton | 0 | 0 | 0 | 0 |
| Crabgrass | 0 | 0 | 0 | 0 |
| Downy brome | 0 | 0 | 0 | 0 |
| Duck salad | 0 | 0 | 7 | 8 |
| Giant foxtail | 0 | 0 | 0 | 0 |
| Lambsquarters | — | 0 | 0 | 0 |
| Morningglory | 0 | 0 | 0 | 0 |
| Pigweed | 0 | 0 | 0 | 0 |
| Rape | 0 | 0 | 0 | 0 |
| Ryegrass | 2 | 0 | 4 | 0 |
| Sorghum | 0 | 0 | 0 | 0 |
| Soybean | 0 | 0 | 0 | 0 |
| Speedwell | 0 | 0 | 0 | — |
| Sugar beet | 0 | 0 | 0 | 0 |
| Velvetleaf | 0 | 0 | 0 | 0 |
| Wheat | 0 | 0 | 0 | 0 |
| Wild buckwheat | 0 | 0 | 0 | — |
| Wild oat | 0 | 0 | 0 | 0 |
| Barnyardgrass | 10 | 10 | 10 | 9 |
| Rice Japonica | 5 | 2 | 8 | 8 |
| Umbrella sedge | 8 | 8 | 9 | 9 |

| Rate (31 g/ha) | COMPOUND | | | |
|---|---|---|---|---|
| | 1 | 3 | 4 | 5 |
| POSTEMERGENCE | | | | |
| Barley Igri | 0 | 0 | 0 | 0 |
| Bedstraw | 0 | 0 | 0 | 0 |
| Blackgrass | 0 | 0 | 0 | 0 |
| Chickweed | 0 | 0 | 0 | — |
| Corn | 0 | 0 | 0 | 0 |
| Cotton | 0 | 0 | 0 | 0 |
| Crabgrass | 0 | 0 | 0 | 0 |
| Downy brome | 0 | 0 | 0 | 0 |
| Duck salad | 0 | 0 | 2 | 6 |
| Giant foxtail | 0 | 0 | 0 | 0 |
| Lambsquarters | 0 | 0 | 0 | 0 |
| Morningglory | 0 | 0 | 0 | 0 |
| Pigweed | 0 | 0 | 0 | 0 |
| Rape | 0 | 0 | 0 | 0 |
| Ryegrass | 0 | 0 | 0 | 0 |
| Sorghum | 0 | 0 | 0 | 0 |
| Soybean | 0 | 0 | 0 | 0 |
| Speedwell | 0 | 0 | 0 | 0 |
| Sugar beet | 0 | 0 | 0 | 0 |
| Velvetleaf | 0 | 0 | 0 | 0 |
| Wheat | 0 | 0 | 0 | 0 |
| Wild buckwheat | 0 | 0 | 0 | — |
| Wild oat | 0 | 0 | 0 | 0 |
| Barnyardgrass | 10 | 10 | 10 | 9 |
| Rice Japonica | 1 | 0 | 4 | 6 |
| Umbrella sedge | 8 | 7 | 8 | 9 |

| Rate (16 g/ha) | COMPOUND | | | |
|---|---|---|---|---|
| | 1 | 3 | 4 | 5 |
| POSTEMERGENCE | | | | |
| Barley Igri | 0 | 0 | 0 | 0 |
| Bedstraw | 0 | 0 | 0 | — |
| Blackgrass | 0 | 0 | 0 | 0 |
| Chickweed | 0 | 0 | 0 | 0 |
| Corn | 0 | 0 | 0 | 0 |
| Cotton | 0 | 0 | 0 | 0 |
| Crabgrass | 0 | 0 | 0 | 0 |
| Downy brome | 0 | 0 | 0 | 0 |
| Duck salad | 0 | 0 | 0 | 0 |
| Giant foxtail | 0 | 0 | 0 | 0 |
| Lambsquarters | 0 | 0 | 0 | 0 |
| Morningglory | 0 | 0 | 0 | 0 |
| Pigweed | 0 | 0 | 0 | 0 |
| Rape | 0 | 0 | 0 | 0 |
| Ryegrass | 0 | 0 | 0 | 0 |
| Sorghum | 0 | 0 | 0 | 0 |
| Soybean | 0 | 0 | 0 | 0 |

TABLE B-continued

| | 0 | 0 | 0 | 0 |
|---|---|---|---|---|
| Speedwell | 0 | 0 | 0 | 0 |
| Sugar beet | 0 | 0 | 0 | 0 |
| Velvetleaf | 0 | 0 | 0 | 0 |
| Wheat | 0 | 0 | 0 | 0 |
| Wild buckwheat | 0 | 0 | 0 | — |
| Wild oat | 0 | 0 | 0 | 0 |
| Barnyardgrass | 9 | 10 | 9 | 6 |
| Rice Japonica | 0 | 0 | 3 | 2 |
| Umbrella sedge | 5 | 5 | 8 | 8 |

| | COMPOUND | | | |
|---|---|---|---|---|
| Rate (250 g/ha) | 1 | 3 | 4 | 5 |
| PREEMERGENCE | | | | |
| Barley Igri | 4 | 0 | 0 | — |
| Bedstraw | 0 | 8 | 8 | 0 |
| Blackgrass | 10 | 8 | 10 | 10 |
| Chickweed | 9 | 9 | 9 | 9 |
| Corn | 4 | 2 | 6 | 7 |
| Cotton | 0 | 1 | 0 | 0 |
| Crabgrass | 9 | 9 | 10 | 10 |
| Downy brome | 8 | 3 | 8 | — |
| Duck salad | — | — | — | — |
| Giant foxtail | 10 | 10 | 10 | 10 |
| Lambsquarters | 9 | 8 | 10 | 10 |
| Morningglory | 0 | 2 | 3 | 0 |
| Pigweed | 8 | 7 | 8 | 8 |
| Rape | 0 | 0 | 7 | — |
| Ryegrass | 10 | — | 10 | 10 |
| Sorghum | 4 | 2 | 4 | 2 |
| Soybean | 0 | 0 | 3 | 0 |
| Speedwell | 8 | 6 | 10 | 9 |
| Sugar beet | 5 | 0 | 3 | 0 |
| Velvetleaf | 8 | 8 | 9 | 8 |
| Wheat | 3 | 0 | 0 | — |
| Wild buckwheat | 4 | 6 | 6 | 7 |
| Wild oat | 4 | 5 | 8 | 9 |
| Barnyardgrass | — | — | — | — |
| Rice Japonica | — | — | — | — |
| Umbrella sedge | — | — | — | — |

| | COMPOUND | | | |
|---|---|---|---|---|
| Rate (125 g/ha) | 1 | 3 | 4 | 5 |
| PREEMERGENCE | | | | |
| Barley Igri | 0 | 0 | 0 | 5 |
| Bedstraw | 0 | 3 | 8 | — |
| Blackgrass | 7 | 0 | 7 | 9 |
| Chickweed | 9 | 0 | 8 | 9 |
| Corn | 3 | 0 | 4 | 2 |
| Cotton | 0 | 0 | 0 | 0 |
| Crabgrass | 9 | 9 | 10 | 10 |
| Downy brome | 5 | 3 | 3 | 6 |
| Duck salad | — | — | — | — |
| Giant foxtail | 10 | 9 | 10 | 9 |
| Lambsquarters | 9 | 4 | 9 | 9 |
| Morningglory | 0 | 0 | 2 | 0 |
| Pigweed | 7 | 7 | 8 | 8 |
| Rape | 0 | 0 | 0 | 4 |
| Ryegrass | 8 | 5 | 9 | 8 |
| Sorghum | 2 | 0 | 3 | 0 |
| Soybean | 0 | 0 | 0 | 0 |
| Speedwell | 5 | 6 | 9 | 9 |
| Sugar beet | 5 | 0 | 0 | — |
| Velvetleaf | 7 | 8 | 8 | 7 |
| Wheat | 0 | 0 | 0 | 4 |
| Wild buckwheat | — | 6 | 0 | 0 |
| Wild oat | 2 | 0 | 3 | 7 |
| Barnyardgrass | — | — | — | — |
| Rice Japonica | — | — | — | — |
| Umbrella sedge | — | — | — | — |

| | COMPOUND | | | |
|---|---|---|---|---|
| Rate (62 g/ha) | 1 | 3 | 4 | 5 |
| PREEMERGENCE | | | | |
| Barley Igri | 0 | 0 | 0 | 0 |
| Bedstraw | 0 | 2 | — | 0 |
| Blackgrass | 5 | 0 | 0 | 5 |
| Chickweed | 8 | 0 | 8 | 5 |
| Corn | 0 | 0 | 0 | 0 |
| Cotton | 0 | 0 | 0 | 0 |
| Crabgrass | 9 | 8 | 10 | 9 |
| Downy brome | 3 | 2 | 0 | 0 |
| Duck salad | — | — | — | — |
| Giant foxtail | 10 | 9 | 9 | 8 |
| Lambsquarters | 4 | 3 | 9 | 8 |
| Morningglory | 0 | 0 | 0 | 0 |
| Pigweed | 6 | 2 | 7 | 7 |
| Rape | 0 | — | 0 | 3 |
| Ryegrass | 2 | 0 | 8 | 6 |
| Sorghum | 1 | 0 | 2 | 0 |
| Soybean | 0 | 0 | 0 | 0 |
| Speedwell | 0 | 5 | 9 | 6 |
| Sugar beet | 0 | 0 | 0 | 0 |
| Velvetleaf | 6 | 6 | 8 | 7 |
| Wheat | 0 | 0 | 0 | 3 |
| Wild buckwheat | 4 | 0 | — | 0 |
| Wild oat | — | 0 | 3 | 0 |
| Barnyardgrass | — | — | — | — |
| Rice Japonica | — | — | — | — |
| Umbrella sedge | — | — | — | — |

| | COMPOUND | | | |
|---|---|---|---|---|
| Rate (31 g/ha) | 1 | 3 | 4 | 5 |
| PREEMERGENCE | | | | |
| Barley Igri | 0 | 0 | 0 | 0 |
| Bedstraw | 0 | 0 | 0 | 0 |
| Blackgrass | 0 | 0 | 0 | 5 |
| Chickweed | 0 | 0 | 8 | 5 |
| Corn | 0 | 0 | 0 | 0 |
| Cotton | 0 | 0 | 0 | 0 |
| Crabgrass | 7 | 7 | 8 | 8 |
| Downy brome | 0 | 0 | — | 0 |
| Duck salad | — | — | — | — |
| Giant foxtail | 7 | 7 | 9 | 6 |
| Lambsquarters | 4 | 0 | 0 | 8 |
| Morningglory | 0 | 0 | 0 | 0 |
| Pigweed | 4 | 0 | 5 | 5 |
| Rape | — | 0 | 0 | 0 |
| Ryegrass | 0 | 0 | 3 | 0 |
| Sorghum | 1 | 0 | 0 | 0 |
| Soybean | 0 | 0 | 0 | 0 |
| Speedwell | 0 | 0 | — | 6 |
| Sugar beet | 0 | 0 | — | 0 |
| Velvetleaf | 5 | 5 | 6 | 5 |
| Wheat | 0 | 0 | 0 | 2 |
| Wild buckwheat | 4 | 0 | — | 0 |
| Wild oat | 0 | 0 | 0 | 0 |
| Barnyardgrass | — | — | — | — |
| Rice Japonica | — | — | — | — |
| Umbrella sedge | — | — | — | — |

| | COMPOUND | | | |
|---|---|---|---|---|
| Rate (16 g/ha) | 1 | 3 | 4 | 5 |
| PREEMERGENCE | | | | |
| Barley Igri | 0 | 0 | 0 | 0 |
| Bedstraw | 0 | 0 | 0 | 0 |
| Blackgrass | 0 | 0 | 0 | 4 |
| Chickweed | 0 | 0 | 6 | 5 |
| Corn | 0 | 0 | 0 | 0 |
| Cotton | 0 | 0 | 0 | 0 |
| Crabgrass | 6 | 5 | 5 | 4 |
| Downy brome | 0 | 0 | 0 | 0 |
| Duck salad | — | — | — | — |
| Giant foxtail | 3 | 7 | 5 | 5 |
| Lambsquarters | 0 | 0 | 0 | 0 |
| Morningglory | 0 | 0 | 0 | 0 |
| Pigweed | 0 | 0 | 0 | 2 |
| Rape | 0 | 0 | 0 | 0 |
| Ryegrass | 0 | 0 | — | 0 |
| Sorghum | 0 | 0 | 0 | 0 |
| Soybean | 0 | 0 | 0 | 0 |
| Speedwell | 0 | 0 | 5 | 0 |
| Sugar beet | 0 | 0 | 0 | 0 |
| Velvetleaf | 3 | 2 | 5 | 3 |
| Wheat | 0 | 0 | 0 | 0 |
| Wild buckwheat | — | 0 | — | 0 |
| Wild oat | 0 | 0 | 0 | 0 |
| Barnyardgrass | — | — | — | — |
| Rice Japonica | — | — | — | — |
| Umbrella sedge | — | — | — | — |

TABLE B-continued

TABLE C-continued

| | | | |
|---|---|---|---|
| Barnyardgrass | 3 | 3 | 0 |
| Duck salad | 0 | 0 | 0 |
| Japonica rice | 0 | 0 | 0 |
| Umbrella sedge | 6 | 0 | 5 |
| Waterchestnut | 0 | 0 | 0 |

TEST C

Plastic pots were partially filled with silt loam soil. The soil was then saturated with water. Japonica rice (*Oryza sativa*) seedlings at the 2.0 to 2.5 leaf stage, seeds selected from barnyardgrass (*Echinochloa crus-galli*) duck salad (*Heteranthera limosa*), umbrella sedge (*Cyperus difformis*), and tubers selected from arrowhead (*Sagittaria* spp.), waterchestnut (*Eleocharis* spp.), were planted into this soil. After planting, water levels were raised to 3 cm above the soil surface and maintained at this level throughout the test. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table C, are reported on a 0 to 10 scale where 0 is no effect and 10 is complete control. A dash (-) response means no test result.

TABLE C

| | COMPOUND | | |
|---|---|---|---|
| Rate (125 g/ha) | 1 | 3 | 4 |
| PADDY | | | |
| Arrowhead | 0 | — | 3 |
| Barnyardgrass | 10 | 10 | 10 |
| Duck salad | 10 | 10 | 10 |
| Japonica rice | 1 | 0 | 2 |
| Umbrella sedge | 9 | 9 | 10 |
| Waterchestnut | 3 | 5 | 5 |

| | COMPOUND | | |
|---|---|---|---|
| Rate (64 g/ha) | 1 | 3 | 4 |
| PADDY | | | |
| Arrowhead | 0 | — | 3 |
| Barnyardgrass | 8 | 10 | 9 |
| Duck salad | 10 | 10 | 10 |
| Japonica rice | 1 | 0 | 1 |
| Umbrella sedge | 9 | 9 | 9 |
| Waterchestnut | 3 | 4 | 3 |

| | COMPOUND | | |
|---|---|---|---|
| Rate (32 g/ha) | 1 | 3 | 4 |
| PADDY | | | |
| Arrowhead | 0 | — | 3 |
| Barnyardgrass | 10 | 7 | 9 |
| Duck salad | 10 | 10 | 10 |
| Japonica rice | 0 | 0 | 0 |
| Umbrella sedge | 9 | 9 | 9 |
| Waterchestnut | 1 | 0 | 3 |

| | COMPOUND | | |
|---|---|---|---|
| Rate (16 g/ha) | 1 | 3 | 4 |
| PADDY | | | |
| Arrowhead | — | — | 0 |
| Barnyardgrass | 7 | 5 | 7 |
| Duck salad | 9 | 10 | 10 |
| Japonica rice | 0 | 0 | 0 |
| Umbrella sedge | 9 | 9 | 9 |
| Waterchestnut | 0 | 0 | 2 |

| | COMPOUND | | |
|---|---|---|---|
| Rate (8 g/ha) | 1 | 3 | 4 |
| PADDY | | | |
| Arrowhead | 3 | — | 0 |

TEST D

Plastic pots were partially filled with silt loam soil. The soil was then flooded with water, Japonica rice (*Oryza sativa*) sprouted seeds and 1.5 leaf transplants were planted in the soil. Seeds of barnyardgrass (*Echinochloa crus-galli*) were planted in saturated soil and plants grown to the 2 and 3 leaf stages for testing. At testing, the water level for all plantings was raised to 2 cm above the soil surface. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table D are reported on a to 10 scale where 0 is no effect and 10 is complete control. A dash (-) response means no test result.

TABLE D

| | COMPOUND |
|---|---|
| Rate (250 g/ha) | 1 |
| PADDY | |
| 2-LF B.Y. Grass | 10 |
| 3-lf B.Y. Grass | 10 |
| Jap Direct Seed | 10 |
| Jap Rice Eff | 6 |

| | COMPOUND | | |
|---|---|---|---|
| Rate (125 g/ha) | 1 | 3 | 4 |
| PADDY | | | |
| 2-LF B.Y. Grass | 10 | 9 | 10 |
| 3-lb B.Y. Grass | 10 | 10 | 9 |
| Jap Direct Seed | 10 | 9 | 10 |
| Jap Rice Eff | 3 | 0 | 2 |

| | COMPOUND | | |
|---|---|---|---|
| Rate (64 g/ha) | 1 | 3 | 4 |
| PADDY | | | |
| 2-LF B.Y. Grass | 10 | 10 | 9 |
| 3-lb B.Y. Grass | 9 | 8 | 9 |
| Jap Direct Seed | 8 | 9 | 10 |
| Jap Rice Eff | 3 | 0 | 1 |

| | COMPOUND | | |
|---|---|---|---|
| Rate (32 g/ha) | 1 | 3 | 4 |
| PADDY | | | |
| 2-LF B.Y. Grass | 10 | 8 | 9 |
| 3-lb B.Y. Grass | 7 | 6 | 6 |
| Jap Direct Seed | 7 | 5 | 9 |
| Jap Rice Eff | 1 | 0 | 1 |

| | COMPOUND | | |
|---|---|---|---|
| Rate (16 g/ha) | 1 | 3 | 4 |
| PADDY | | | |
| 2-LF B.Y. Grass | 8 | 6 | 6 |
| 3-lb B.Y. Grass | 6 | 2 | 3 |
| Jap Direct Seed | 5 | 3 | 2 |

TABLE D-continued

| | Jap Rice Eff | 1 | 0 | .0 |
|---|---|---|---|---|
| | | COMPOUND | | |
| Rate (8 g/ha) | | 1 | 3 | 4 |
| PADDY | | | | |
| 2-LF B.Y. Grass | | 5 | 3 | 2 |
| 3-lb B.Y. Grass | | 0 | 0 | 2 |
| Jap Direct Seed | | 1 | 0 | 2 |
| Jap Rice Eff | | 1 | 0 | 0 |

What is claimed is:

1. A compound and stereoisomers of the following formula

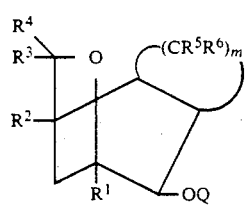

wherein
m is 1,
$R^1$ is straight chain $C_1$-$C_3$ alkyl;
$R^2$ is H,
$R^3$ and $R^4$ are H,
$R^5$ and $R^6$ are H,
Q is $CH_2W$ or

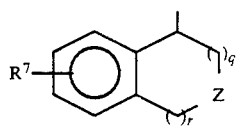

q and r are independently 0, 1 or 2;
$R^7$ is H, halogen, $C_1$-$C_3$ alkyl, $OR^8$, $SR^8$ or CN;
$R^8$ is $C_1$-$C_3$ alkyl or $C_1$-$C_3$ haloalkyl;
Z is $CH_2$, $NR^9$, O, S or may be CH and taken to form a double bond with an adjacent carbon;
$R^9$ is H or $C_1$-$C_3$ alkyl;
W is phenyl optionally substituted with 1-3 substituents selected from halogen, $C_1$-$C_3$ alkyl, $C_1$-$C_3$ alkoxy, OH, CN, $C_1$-$C_3$ haloalkyl, $C_1$-$C_3$ haloalkoxy, $C_1$-$C_3$ alkylthio, $C_2$-$C_4$ alkenyl and $C_2$-$C_4$ alkynyl; or W is selected from the group consisting of tetrahydropyran, furan, tetrahydrofuran, thiophene and pyridine, said heterocyclic ring optionally substituted with 1-2 substituents selected from the group consisting of halogen, $CH_3$ and $OCH_3$;
provided that
1) the sum of q and r is 0-2; and
2) if the sum of q and r is 0 then Z is $CH_2$.

2. The compounds of claim 1 wherein:
Q is $CH_2W$ or

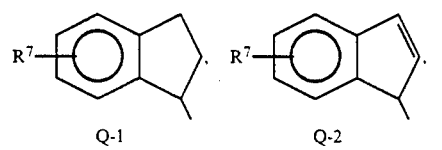

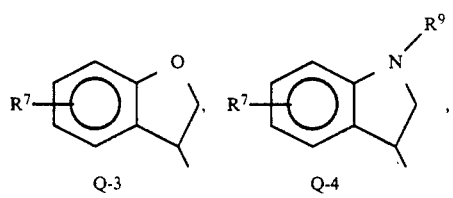

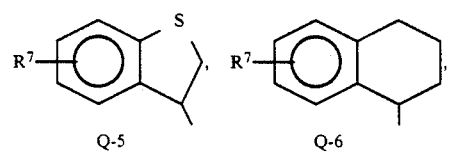

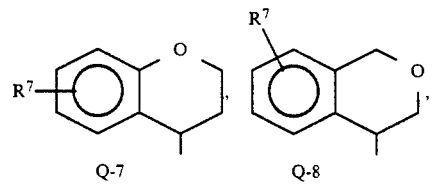

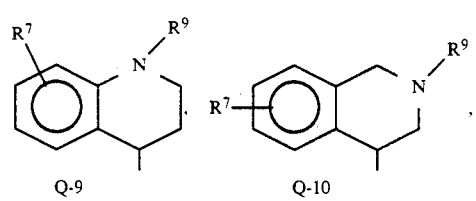

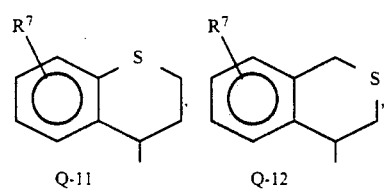

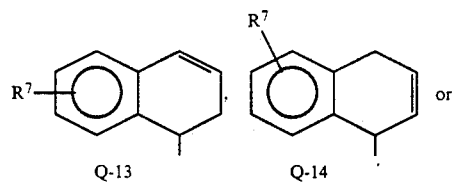

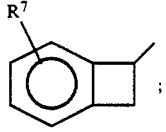

W is phenyl optionally substituted with 1-2 substituents selected from F, Cl, Br, $CH_3$ and $OCH_3$; or W is tetrahydroyran, tetrahdrofuran, thiophene, pyridine or each ring optionally substituted with 1-2 substituents selected from F, Cl, Br, $CH_3$ and $OCH_3$.

3. The compounds of claim 2 wherein:

Q is CH$_2$W, Q-1, Q-3, Q-4, Q-6, Q-7, Q-8 or Q-15;
W is phenyl optionally substituted with 1-2 substituents selected from F, Cl, Br and CH$_3$; tetrahydrofuran; thiophene optionally substituted with Cl or Br; or pyridine.

4. The compounds of claim 3 wherein:
R$^1$ is CH$_3$ or CH$_2$CH$_3$;
Q is CH$_2$W.

5. The compound of claim 3 which is (1α,2α,4α,5β,6α)-(+/−)-5-[(2-fluorophenyl)-methoxy]-6-methyl-7-oxatricyclo[4.2.1.0$^{2,4}$]-nonane.

6. An agriculturally suitable composition for controlling the growth of undesired vegetation comprising an effective amount of a compound of any one of claims 1-5 and at least one of the following: surfactant, solid or liquid diluent.

* * * * *

UNITED STATES PATENT AND TRADEMARK OFFICE
CERTIFICATE OF CORRECTION

PATENT NO. : 5,175,314

DATED : December 29, 1992

INVENTOR(S) : Wendy S. Taylor

It is certified that error appears in the above-identified patent and that said Letters Patent is hereby corrected as shown below:

Col. 2, lines 25-34, delete formula IV and substitute therefore the following:

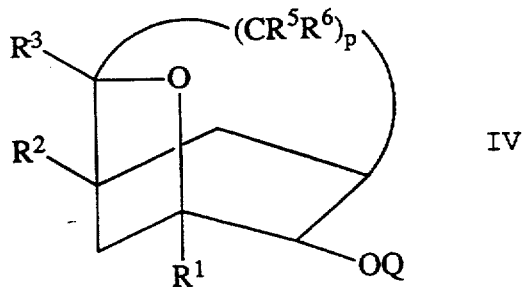

IV

Col. 2, lines 41-48, delete formula VI and substitute therefore the following:

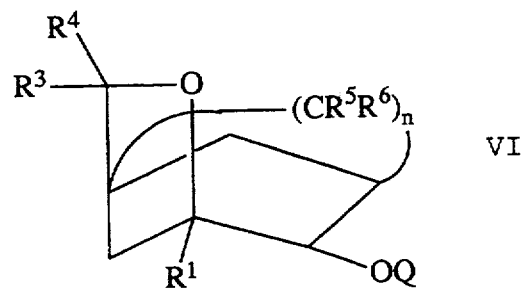

VI

UNITED STATES PATENT AND TRADEMARK OFFICE
CERTIFICATE OF CORRECTION

PATENT NO.  : 5,175,314
DATED       : December 29, 1992
INVENTOR(S) : Wendy S. Taylor It is certified that error appears in the above-identified patent and that said Letters Patent is hereby corrected as shown below:

Col. 4, line 60, delete "Ch3" and insert -- $CH_3$ --.

Col. 8, line 22, before "175" insert -- 29 --.

Col. 9, in formulas (11), (12), (19) and (15) and in Col. 10, formula (19) all should have the oxygen atom connected with lines to carbons as shown below:

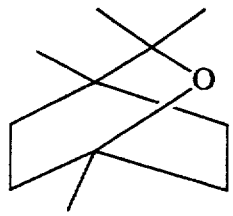

Col. 11, formulas (22) and (24) should have an $R^2$ in the location indicated below:

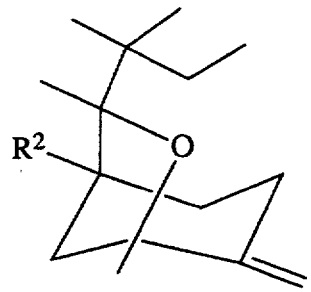

UNITED STATES PATENT AND TRADEMARK OFFICE
CERTIFICATE OF CORRECTION

PATENT NO. : 5,175,314

DATED : December 29, 1992

INVENTOR(S) : Wendy S. Taylor

It is certified that error appears in the above-identified patent and that said Letters Patent is hereby corrected as shown below:

Col. 12, formula (26) delete "$R^3$" and replace with -- $R^4$ -- and add the substituent "$R^2$" as indicated below:

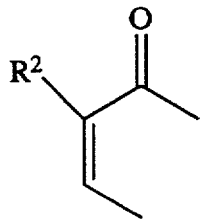

Col. 12, formula (27) delete "$R^3$" and replace with -- $R^4$ --, add substitutent "$R^2$" as indicated below and connect the lines to show the ring indicated below:

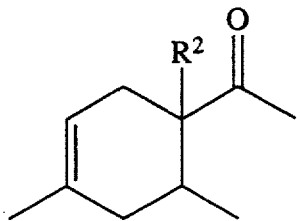

Col. 12, between formula (27) and Formula (28) delete "$R^4M$ and insert -- $R^3M$ --.

UNITED STATES PATENT AND TRADEMARK OFFICE
CERTIFICATE OF CORRECTION

PATENT NO. : 5,175,314

DATED : December 29, 1992

INVENTOR(S) : Wendy S. Taylor

It is certified that error appears in the above-identified patent and that said Letters Patent is hereby corrected as shown below:

Col. 12, Formula (28) add the substituent "$R^2$" at the location indicated below:

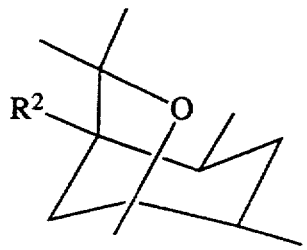

Col. 12, Scheme 11, the second reactant should have the structure:

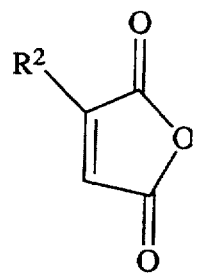

UNITED STATES PATENT AND TRADEMARK OFFICE
CERTIFICATE OF CORRECTION

PATENT NO. : 5,175,314

DATED : December 29, 1992

INVENTOR(S) : Wendy S. Taylor

It is certified that error appears in the above-identified patent and that said Letters Patent is hereby corrected as shown below:

Col. 12, formula (29) add the substituent "$R^2$" at the location indicated below:

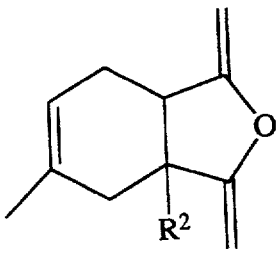

Col. 12, formula (30) add the substituent "$R^2$" at the location indicated below:

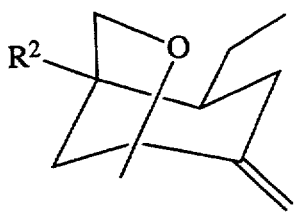

Col. 12, formula (31) and (32) delete "$R^3$" and substitute therefore -- $R^4$ --.

Col. 12, between formula (32) and (33) delete "$R^4M$" and substitute therefore -- $R^3M$ --.

UNITED STATES PATENT AND TRADEMARK OFFICE
CERTIFICATE OF CORRECTION

PATENT NO. : 5,175,314

DATED : December 29, 1992

INVENTOR(S) : Wendy S. Taylor

It is certified that error appears in the above-identified patent and that said Letters Patent is hereby corrected as shown below:

Col. 12, formula (33) the structural formula excluding the substituents should be as shown below:

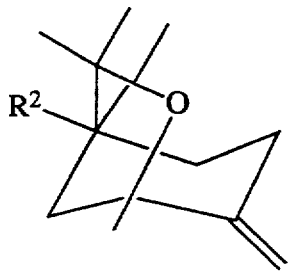

Col. 13, line 50 between "hydroxy" and "methy" delete "55" and substitute therefore -- -5 --.

Col. 14, line 64, delete "5one" and insert therefore -- 5-one --.

Col. 15, line 39, delete "1 16 g" and substitute therefore -- 1.16 g --.

Col. 16, line 1, delete "129 7" and substitute therefore -- 129.7 --; line 2, delete "163,57" and substitute therefore -- 163.57 --.

Col. 18, line 13, delete "I.78" and substitute therefore -- 1.78 --; line 19, delete "2.6Q" and substitute therefore -- 2.60 --; line 25, delete the superscript "4.2" and substitute therefore -- 2.4 --.

UNITED STATES PATENT AND TRADEMARK OFFICE
CERTIFICATE OF CORRECTION

PATENT NO. : 5,175,314

DATED : December 29, 1992

INVENTOR(S) : Wendy S. Taylor

It is certified that error appears in the above-identified patent and that said Letters Patent is hereby corrected as shown below:

Cols. 19 and 20 delete the 38th indicated compound from the top, namely, "$CH_2(2-Cl.6-FC_6H_3)$".

Cols. 20 and 22 delete "1 Q-1" three occurrences and substitute therefore -- 3 Q-1 --.

Col. 28, the 10th substituent from the top of the column, delete "2.6" and substitute therefore -- 2,6 --.

Col. 30, the 22,23,24,25,26 substituent under column "m" delete "1" and substitute therefore -- 2 --.

UNITED STATES PATENT AND TRADEMARK OFFICE
CERTIFICATE OF CORRECTION

PATENT NO. : 5,175,314

DATED : December 29, 1992

INVENTOR(S) : Wendy S. Taylor

It is certified that error appears in the above-identified patent and that said Letters Patent is hereby corrected as shown below:

Col. 48, after "3 Q-15" add the following:

-- 4    $CH_2(C_6H_5)$
   4    $CH_2(2-FC_6H_4)$
   4    $CH_2(2,6-F_2C_6H_3)$
   4    $CH_2(2-ClC_6H_4)$
   4    $CH_2(2,6-Cl_2C_6H_3)$
   4    $CH_2(2-Cl,6-FC_6H_3)$
   4    $CH_2(2-BrC_6H_4)$
   4    $CH_2(2,6-BrC_6H_3)$
   4    $CH_2(2-(CH_3)C_6H_4)$
   4    $CH_2(2-pyridyl)$
   4    $CH_2(2-thienyl)$
   4    $CH_2(2-furanyl)$
   4    $CH_2(2-tetrahydrofuranyl)$
   4    $CH_2(2-tetrahydropyranyl)$
   4    Q-1
   4    Q-3
   4    Q-4
   4    Q-6
   4    Q-7
   4    Q-8
   4    Q-15
   4    $CH_2(2-(OCH_3)C_6H_4)$
   4    $CH_2(2,4-F_2C_6H_3)$
   4    $CH_2(2-(CN)C_6H_4)$
   4    $CH_2(2-(CF_3)C_6H_4)$
   4    $CH_2(2-(CH=CH_2)C_6H_4)$ --.

UNITED STATES PATENT AND TRADEMARK OFFICE
CERTIFICATE OF CORRECTION

PATENT NO. : 5,175,314
DATED : December 29, 1992
INVENTOR(S) : Wendy S. Taylor

It is certified that error appears in the above-identified patent and that said Letters Patent is hereby corrected as shown below:

Col. 49, insert above "$R^1=R^5=CH_3$" the following:

-- $R^1=R^5=CH_3$, $R^3=R^4=R^6=H$

| n | Q |
|---|---|
| 2 | $CH_2(C_6H_5)$ |
| 2 | $CH_2(2-FC_6H_4)$ |
| 2 | $CH_2(2,6-F_2C_6H_3)$ |
| 2 | $CH_2(2-ClC_6H_4)$ |
| 2 | $CH_2(2,6-Cl_2C_6H_3)$ |
| 2 | $CH_2(2-Cl,6-FC_6H_3)$ |
| 2 | $CH_2(2-BrC_6H_4)$ |
| 2 | $CH_2(2-(CH_3)C_6H_4)$ |
| 2 | $CH_2(2-tetrahydrofuranyl)$ |
| 2 | $CH_2(2-tetrahydropyranyl)$ |
| 2 | $CH_2(2-,4-F_2C_6H_3)$ |
| 2 | $CH_2(2-(CH=CH_2)C_6H_4)$ |
| 2 | Q-1 |
| 3 | $CH_2(C_6H_5)$ |
| 3 | $CH_2(2-FC_6H_4)$ |
| 3 | $CH_2(2,6-F_2C_6H_3)$ |
| 3 | $CH_2(2-ClC_6H_4)$ |
| 3 | $CH_2(2,6-Cl_2C_6H_3)$ |
| 3 | $CH_2(2-Cl,6-FC_6H_3)$ |

--.

Col. 49, second line from bottom, delete "H" and substitute therefore -- $OCH_3$ --.

UNITED STATES PATENT AND TRADEMARK OFFICE
CERTIFICATE OF CORRECTION

PATENT NO. : 5,175,314

DATED : December 29, 1992

INVENTOR(S) : Wendy S. Taylor

It is certified that error appears in the above-identified patent and that said Letters Patent is hereby corrected as shown below:

Col. 50, delete the following which appears above "$R^3=R^4=R^1CH_3$":

| | |
|---|---|
| 4 | $CH_2(C_6H_5)$ |
| 4 | $CH_2(2-FC_6H_4)$ |
| 4 | $CH_2(2,6-F_2C_6H_3)$ |
| 4 | $CH_2(2-ClC_6H_4)$ |
| 4 | $CH_2(2,6-Cl_2C_6H_3)$ |
| 4 | $CH_2(2-Cl,6-FC_6H_3)$ |
| 4 | $CH_2(2-BrC_6H_4)$ |
| 4 | $CH_2(2,6-BrC_6H_3)$ |
| 4 | $CH_2(2-(CH_3)C_6H_4)$ |
| 4 | $CH_2(2-pyridyl)$ |
| 4 | $CH_2(2-thienyl)$ |
| 4 | $CH_2(2-furanyl)$ |
| 4 | $CH_2(2-tetrahydrofuranyl)$ |
| 4 | $CH_2(2-tetrahydropyranyl)$ |
| 4 | Q-1 |
| 4 | Q-3 |
| 4 | Q-4 |
| 4 | Q-6 |
| 4 | Q-7 |
| 4 | Q-8 |
| 4 | Q-15 |
| 4 | $CH_2(2-(OCH_3)C_6H_4)$ |
| 4 | $CH_2(2,4-F_2C_6H_3)$ |
| 4 | $CH_2(2-(CN)C_6H_4)$ |
| 4 | $CH_2(2-(CF_3)C_6H_4)$ |
| 4 | $CH_2(2-(CH=CH_2)C_6H_4)$ ". |

UNITED STATES PATENT AND TRADEMARK OFFICE
CERTIFICATE OF CORRECTION

PATENT NO. : 5,175,314

DATED : December 29, 1992

INVENTOR(S) : Wendy S. Taylor

It is certified that error appears in the above-identified patent and that said Letters Patent is hereby corrected as shown below:

Col. 50, above the "$R^1=R^5=CH_3$" add the following:

--         $R^1=R^5=CH_3$, $R^3=R^4=R^6=H$

| n | Q |
|---|---|
| 4 | $CH_2(C_6H_5)$ |
| 4 | $CH_2(2-FC_6H_4)$ |
| 4 | $CH_2(2,6-F_2C_6H_3)$ |
| 4 | $CH_2(2-ClC_6H_4)$ |
| 4 | $CH_2(2,6-Cl_2C_6H_3)$ |
| 4 | $CH_2(2-Cl,6-FC_6H_3)$ |
| 4 | $CH_2(2-BrC_6H_4)$ |
| 4 | $CH_2(2-(CH_3)C_6H_4)$ |
| 4 | $CH_2(2-tetrahydrofuranyl)$ |
| 4 | $CH_2(2-tetrahydropyranyl)$ |
| 4 | $CH_2(2,4-F_2C_6H_3)$ |
| 4 | $CH_2(2-(CH=CH_2)C_6H_4)$ |
| 4 | Q-1 |
| 4 | $CH_2(2-(CH_3)C_6H_4)$ |
| 4 | $CH_2(2-tetrahydrofuranyl)$ |
| 4 | $CH_2(2-tetrahydropyranyl)$ |
| 4 | $CH_2(2,4-F_2C_6H_3)$ |
| 4 | $CH_2(2-(CH=CH_2)C_6H_4)$   --. |

UNITED STATES PATENT AND TRADEMARK OFFICE
CERTIFICATE OF CORRECTION

PATENT NO. : 5,175,314

DATED : December 29, 1992

INVENTOR(S) : Wendy S. Taylor

It is certified that error appears in the above-identified patent and that said Letters Patent is hereby corrected as shown below:

Col. 70, delete the structural formula for "V" and substitute the following:

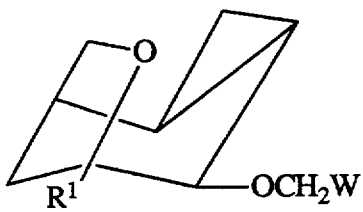

Col. 72, in the NMR values for compound 7 delete "1.20 (d,1H)" and substitute therefore -- 1.30 (d,1H) --.

Col. 72, in the NMR values for compound 11, delete "4.829 d,1H)" and insert therefore -- 4.82 (d,1H) --.

Signed and Sealed this

Twenty-ninth Day of November, 1994

Attest:

BRUCE LEHMAN

*Attesting Officer*    *Commissioner of Patents and Trademarks*